(12) United States Patent
Hoare et al.

(10) Patent No.: US 10,363,340 B2
(45) Date of Patent: Jul. 30, 2019

(54) POLY(OLIGOETHYLENE GLYCOL METHACRYLATE) HYDROGEL COMPOSITIONS, AND METHODS OF USE THEREOF

(71) Applicant: McMaster University, Hamilton (CA)

(72) Inventors: Todd Hoare, Ancaster (CA); Emilia Bakaic, Hamilton (CA); Niels M. B. Smeets, Courtice (CA); Xudong Deng, Hamilton (CA)

(73) Assignee: McMaster University, Hamilton, Ontario (CA)

(*) Notice: Subject to any disclaimer, the term of this patent is extended or adjusted under 35 U.S.C. 154(b) by 339 days.

(21) Appl. No.: 14/932,444

(22) Filed: Nov. 4, 2015

(65) Prior Publication Data

US 2016/0151535 A1  Jun. 2, 2016

Related U.S. Application Data

(60) Provisional application No. 62/074,868, filed on Nov. 4, 2014.

(51) Int. Cl.
| | | |
|---|---|---|
| A61L 26/00 | (2006.01) |
| A61M 5/19 | (2006.01) |
| A61L 27/26 | (2006.01) |
| A61L 27/52 | (2006.01) |
| A61L 24/00 | (2006.01) |
| A61L 24/04 | (2006.01) |

(52) U.S. Cl.
CPC ....... *A61L 26/0052* (2013.01); *A61L 24/0031* (2013.01); *A61L 24/043* (2013.01); *A61L 26/008* (2013.01); *A61L 27/26* (2013.01); *A61L 27/52* (2013.01); *A61M 5/19* (2013.01)

(58) Field of Classification Search
CPC ....................................................... C08L 33/10
See application file for complete search history.

(56) References Cited

U.S. PATENT DOCUMENTS

2012/0046407 A1* 2/2012 Clarke .................... B01J 13/14
524/458

OTHER PUBLICATIONS

X.-J. Ju, L.-Y. Chu, X.-L. Zhu, L. Hu, H. Song, W.-M. Chen, Effects of internal microstructures of poly( N-isopropylacrylamide) hydrogels on thermo-responsive volume phase-transition and controlled-release characteristics, Smart Mater. Struct. 15 (2006) 1767-1774. doi:10.1088/0964-1726/15/6/031.

K. Makino, J. Hiyoshi, H. Ohshima, Effects of thermosensitivity of poly (N-isopropylacrylamide) hydrogel upon the duration of a lag phase at the beginning of drug release from the hydrogel., Colloids Surf. B. Biointerfaces. 20 (2001) 341-346.

M.A. Cooperstein, H.E. Canavan, Biological cell detachment from poly(N-isopropyl acrylamide) and its applications., Langmuir. 26 (2010) 7695-7707. doi:10.1021/la902587p.

(Continued)

*Primary Examiner* — Peter F Godenschwager
(74) *Attorney, Agent, or Firm* — Bereskin & Parr LLP/S.E.N.C.R.L.; Michael Fenwick

(57) ABSTRACT

The present application relates to hydrogel compositions comprising first and second precursor polymers, wherein the precursor polymers are modified poly(oligoethylene glycol methacrylate) copolymers that are crosslinked through electrophile-nucleophile reactions.

19 Claims, 30 Drawing Sheets

(56) References Cited

OTHER PUBLICATIONS

R.M.P. da Silva, J.F. Mano, R.L. Reis, Smart thermoresponsive coatings and surfaces for tissue engineering: switching cell-material boundaries., Trends Biotechnol. 25 (2007) 577-583. doi:10.1016/j.tibtech.2007.08.014.

T. Okano, N. Yamada, M. Okuhara, H. Sakai, Y. Sakurai, Mechanism of cell detachment from temperature-modulated, hydrophilic-hydrophobic polymer surfaces, Biomaterials. 16 (1995) 297-303. doi:10.1016/0142-9612(95)93257-E.

H.G. Schild, Poly(N-isopropylacrylamide): experiment, theory and application, Prog. Polym. Sci. 17 (1992) 163-249. doi:10.1016/0079-6700(92)90023-R.

H. Vihola, A. Laukkanen, L. Valtola, H. Tenhu, J. Hirvonen, Cytotoxicity of thermosensitive polymers poly(N-isopropylacrylamide), poly(N-vinylcaprolactam) and amphiphilically modified poly(N-vinylcaprolactam)., Biomaterials. 26 (2005) 3055-3064. doi:10.1016/j.biomaterials.2004.09.008.

M.A. Cooperstein, H.E. Canavan, Assessment of cytotoxicity of (N-isopropyl acrylamide) and Poly(N-isopropyl acrylamide)-coated surfaces—Springer, Biointerphases. 8 (2013).

S. Sun, P. Wu, On the Thermally Reversible Dynamic Hydration Behavior of Oligo(ethylene glycol) Methacrylate-Based Polymers in Water, Macromolecules. 46 (2013) 236-246. doi:10.1021/ma3022376.

C.-C. Lin, K.S. Anseth, PEG hydrogels for the controlled release of biomolecules in regenerative medicine., Pharm. Res. 26 (2009) 631-43.

J.L. Drury, D.J. Mooney, Hydrogels for tissue engineering: scaffold design variables and applications, Biomaterials. 24 (2003) 4337-4351.

N. a. Peppas, J.Z. Hilt, a. Khademhosseini, R. Langer, Hydrogels in Biology and Medicine: From Molecular Principles to Bionanotechnology, Adv. Mater. 18 (2006) 1345-1360.

J. Jokerst, T. Lobovkina, R.N. Zare, S.S. Gambhir, Nanoparticle PEGylation for imaging and therapy, Nanomedicine. 6 (2011) 715-728.

C.R. Nuttelman, M. a Rice, A.E. Rydholm, C.N. Salinas, D.N. Shah, K.S. Anseth, Macromolecular Monomers for the Synthesis of Hydrogel Niches and Their Application in Cell Encapsulation and Tissue Engineering., Prog. Polym. Sci. 33 (2008) 167-179.

M. Malkoch, R. Vestberg, N. Gupta, L. Mespouille, P. Dubois, A.F. Mason, et al., Synthesis of well-defined hydrogel networks using Click chemistry, Chem. Commun. (2006) 2774.

J.D. McCall, K.S. Anseth, Thiol-ene photopolymerizations provide a facile method to encapsulate proteins and maintain their bioactivity., Biomacromolecules. 13 (2012) 2410-7.

A. a Aimetti, A.J. Machen, K.S. Anseth, Poly(ethylene glycol) hydrogels formed by thiol-ene photopolymerization for enzyme-responsive protein delivery., Biomaterials. 30 (2009) 6048-54.

Y. Fu, W.J. Kao, In situ forming poly(ethylene glycol)-based hydrogels via thiol-maleimide Michael-type addition., J. Biomed. Mater. Res. A. 98 (2011) 201-11.

M.P. Lutolf, J. a Hubbell, Synthesis and physicochemical characterization of end-linked poly(ethylene glycol)-co-peptide hydrogels formed by Michael-type addition., Biomacromolecules. 4 (2003) 713-22.

S.P. Zustiak, J.B. Leach, Hydrolytically degradable poly(ethylene glycol) hydrogel scaffolds with tunable degradation and mechanical properties., Biomacromolecules. 11 (2010) 1348-57.

B.D. Polizzotti, B.D. Fairbanks, K.S. Anseth, Three-dimensional biochemical patterning of click-based composite hydrogels via thiolene photopolymerization., Biomacromolecules. 9 (2008) 1084-7.

K.C. Koehler, K.S. Anseth, C.N. Bowman, Diels-Alder mediated controlled release from a poly(ethylene glycol) based hydrogel, Biomacromolecules. 14 (2013) 538-547.

G. N. Grover, J. Lam, T.H. Nguyen, T. Segura, H.D. Maynard, Biocompatible hydrogels by oxime Click chemistry., Biomacromolecules. 13 (2012) 3013-7.

H. Saito, a. S. Hoffman, H.I. Ogawa, Delivery of Doxorubicin from Biodegradable PEG Hydrogels Having Schiff Base Linkages, J. Bioact. Compat. Polym. 22 (2007) 589-601.

B. Farrugia, K. Kempe, U.S. Schubert, R. Hoogenboom, T.R. Dargaville, Poly(2-oxazoline) Hydrogels for Controlled Fibroblast Attachment, Biomacromolecules. (2013).

J.-F. Lutz, Polymerization of oligo(ethylene glycol) (meth)acrylates: Toward new generations of smart biocompatible materials, J. Polym. Sci. Part A Polym. Chem. 46 (2008) 3459-3470.

M. Luzon, C. Boyer, C. Peinado, T. Corrales, M. Whittaker, L.E.I. Tao, et al., Water-Soluble, Thermoresponsive, Hyperbranched Copolymers Based on PEG-Methacrylates: Synthesis, Characterization, and LCST Behavior, 48 (2010) 2783-2792.

A.H. Soeriyadi, G.-Z. Li, S. Slavin, M.W. Jones, C.M. Amos, C.R. Becer, et al., Synthesis and modification of thermoresponsive poly(oligo(ethylene glycol) methacrylate) via catalytic chain transfer polymerization and thiol-ene Michael addition, Polym. Chem. 2 (2011) 815-822.

J.K. Oh, K. Min, K. Matyjaszewski, Preparation of Poly(oligo(ethylene glycol) monomethyl ether methacrylate) by Homogeneous Aqueous AGET ATRP, Macromolecules. 39 (2006) 3161-3167.

J.-F. Lutz, A. Hoth, Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate, Macromolecules. 39 (2006) 893-896.

J.-F. Lutz, J. Andrieu, S. Üzgün, C. Rudolph, S. Agarwal, Biocompatible, Thermoresponsive, and Biodegradable: Simple Preparation of "All-in-One" Biorelevant Polymers, Macromolecules. 40 (2007) 8540-8543.

J. Lei, C. Mayer, V. Freger, M. Ulbricht, Synthesis and Characterization of Poly(ethylene glycol) Methacrylate Based Hydrogel Networks for Anti-Biofouling Applications, Macromol. Mater. Eng. (2012).

R. Paris, I. Quijada-Garrido, Swelling behaviour of thermosensitive hydrogels based on oligo(ethylene glycol) methacrylates, Eur. Polym. J. 45 (2009) 3418-3425.

J.A. Yoon, C. Gayathri, R.R. Gil, T. Kowalewski, K. Matyjaszewski, Comparison of the Thermoresponsive Deswelling Kinetics of Poly(2-(2-methoxyethoxy)ethyl methacrylate) Hydrogels Prepared by ATRP and FRP, Macromolecules. 43 (2010) 4791-4797.

J.A. Yoon, T. Kowalewski, K. Matyjaszewski, Comparison of Thermoresponsive Deswelling Kinetics of Poly ( oligo ( ethylene oxide ) methacrylate ) -Based Thermoresponsive Hydrogels Prepared by "Graft-from" ATRP, (2011) 2261-2268.

J.-F. Lutz, K. Weichenhan, Ö. Akdemir, A. Hoth, About the Phase Transitions in Aqueous Solutions of Thermoresponsive Copolymers and Hydrogels Based on 2-(2-methoxyethoxy)ethyl Methacrylate and Oligo(ethylene glycol) Methacrylate, Macromolecules. 40 (2007) 2503-2508.

N. Fechler, N. Badi, K. Schade, S. Pfeifer, J.-F. Lutz, Thermogelation of PEG-Based Macromolecules of Controlled Architecture, Macromolecules. 42 (2009) 33-36.

N. M.B. Smeets, E. Bakaic, M. Patenaude, T. Hoare, Injectable and tunable poly(ethylene glycol) analogue hydrogels based on poly(oligoethylene glycol methacrylate)., Chem. Commun. (Camb). 50 (2014) 3306-9.

G. Pasut, F.M. Veronese, Polymer-drug conjugation, recent achievements and general strategies, Prog. Polym. Sci. 32 (2007) 933-961.

N.M.B. Smeets, E. Bakaic, M. Patenaude, T. Hoare, Injectable poly(oligoethylene glycol methacrylate)-based hydrogels with tunable phase transition behaviours: Physicochemical and biological responses., Acta Biomater. (2014).

N.M.B. Smeets, M. Patenaude, D. Kinio, F.M. Yavitt, E. Bakaic, F.-C. Yang, et al., Injectable hydrogels with in situ-forming hydrophobic domains: oligo( d, l -lactide) modified poly(oligoethylene glycol methacrylate) hydrogels, Polym. Chem. (2014).

G.N. Grover, R.L. Braden, K.L. Christman, Oxime Cross-Linked Injectable Hydrogels for Catheter Delivery., Adv. Mater. (2013) 1-6.

D.E. Discher, D.J. Mooney, P.W. Zandstra, NIH Public Access, 324 (2010) 1673-1677.

(56) References Cited

OTHER PUBLICATIONS

S. Pasche, S.M. Paul, J. Voros, N.D. Spencer, M. Textor, Poly(1-lysine)-graft-poly(ethylene glycol) Assembled Monolayers on Niobium Oxide Surfaces: A Quantitative Study of the Influence of Polymer Interfacial Architecture on Resistance to Protein Adsorption by ToF-SIMS and in Situ OWLS, Langmuir. 22 (2003) 9216-9225.

Y. Chung, Protein Adsorption and Cell Alignment on Micropatterned Phosphorylcholine Surfaces, 29 (2009) 320-324.

K.Y. Suh, J. Seong, A. Khademhosseini, P.E. Laibinis, R. Langer, A simple soft lithographic route to fabrication of poly (ethylene glycol) microstructures for protein and cell patterning, Biomaterials. 25 (2004) 557-563.

E. Tziampazis, J. Kohn, P. Moghe, PEG-variant biomaterials as selectively adhesive protein templates: model surfaces for controlled cell adhesion and migration, Biomaterials. 21 (2000) 511-520.

A. Shimoda, S. Sawada, A. Kano, A. Maruyama, A. Moquin, F.M. Winnik, et al., Dual crosslinked hydrogel nanoparticles by nanogel bottom-up method for sustained-release delivery., Colloids Surf. B. Biointerfaces. 99 (2012) 38-44.

H. Du, P. Chandaroy, S.W. Hui, Grafted poly-(ethylene glycol) on lipid surfaces inhibits protein adsorption and cell adhesion, Biochim. Biophys. Acta-Biomembr. 1326 (1997) 236-248.

E. Ruoslahti, RGD and other recognition sequences for integrins., Annu. Rev. Cell Dev. Biol. 12 (1996) 697-715.

E. Ruoslahti, M. Pierschbacher, Arg-Gly-Asp: a versatile cell recognition signal, Cell. 44 (1986) 517-518.

M.D. Pierschbacher, E. Ruoslahti, Cell attachment activity of fibronectin can be duplicated by small synthetic fragments of the molecule, Nature. 309 (1984) 30-33.

U. Hersel, C. Dahmen, H. Kessler, RGD modified polymers: biomaterials for stimulated cell adhesion and beyond, Biomaterials. 24 (2003) 4385-4415.

H.T.T. Duong, T.L. Uyen Nguyen, M.H. Stenzel, Micelles with surface conjugated RGD peptide and crosslinked polyurea core via RAFT polymerization, Polym. Chem. 1 (2010) 171-182.

F. Yang, C.G. Williams, D. Wang, H. Lee, P.N. Manson, J. Elisseeff, the effect of incorporating Rgd adhesive peptide in polyethylene glycol diacrylate hydrogel on osteogenesis of bone marrow stromal cells, Biomaterials. 26 (2005) 5991-5998.

J.A. Burdick, K.S. Anseth, Photoencapsulation of osteoblasts in injectable RGD-modified PEG hydrogels for bone tissue engineering, Biomaterials. 23 (2002) 4315-4323.

D. Guarnieri, A. Capua, M. Ventre, A. Borzacchiello, C. Pedone, D. Marasco, et al., Covalently immobilized RGD gradient on PEG hydrogel scaffold influences cell migration parameters, Acta Biomater. 6 (2010) 2532-2539.

Meid, J., Friedrich, T., Tieke, B., Lindner, P., Richtering, W. Physical Chemistry Chemical Physics. 13, 2011, 3039-3047.

Adachi, J., Sato, N. Journal of Organic Chemistry. 37, 1972, 221-225.

\* cited by examiner

POLY(OLIGOETHYLENE GLYCOL METHACRYLATE) HYDROGEL COMPOSITIONS, AND METHODS OF USE THEREOF

CROSS-REFERENCE TO RELATED APPLICATIONS

The present application claims the benefit of priority from U.S. provisional application No. 62/074,868 filed on Nov. 4, 2014, the contents of which are incorporated herein by reference in their entirety.

FIELD

The present application relates to hydrogel compositions comprising first and second precursor polymers, wherein the precursor polymers are poly(oligoethylene glycol methacrylate) copolymers that are crosslinked through covalent bonds.

BACKGROUND

Poly(ethylene glycol) (PEG) hydrogels have been extensively studied as synthetic matrices for the controlled release of therapeutics and as scaffolds for promoting tissue regeneration (1-3). The wide-spread use of PEG hydrogels in such applications is based on the hydrophilic, non-cytotoxic and non-immunogenic properties of PEG, effectively providing "stealth" capability to the biomaterial to mask the material from the host's immune system (4).

A significant drawback of PEG, however, is that the polymer lacks chemical versatility given that functionalization is typically limited to the hydroxyl chain end(s) (5). This limitation leads to synthetic challenges, which include synthesizing PEG-based hydrogels with desirable properties for various biomedical applications. PEG hydrogels are predominantly synthesized via step-growth polymerization of complimentary $\alpha,\omega$-functionalized PEG precursors (6) using thiolene chemistry (7) (including thiol-Michael addition (8), thiol-maleimide (9), and thiol-vinyl sulfone (10, 11)), alkyne-azide click chemistry (6,12), Diels-Alder chemistry (13), oxime chemistry (14), or Schiff-base formation (15). Although step-growth polymerization minimizes network non-idealities, further chemistry is often required to improve the elasticity, injectability and degradability of these hydrogels to make them suitable for desired applications. In particular, given that only two cross-links can be formed by each functionalized PEG precursor (at chain ends), the resulting hydrogels are typically relatively weak or require high concentrations of PEG precursor. In addition, the lack of potential for direct chain functionalization introduces significant difficulties in terms of modifying the physical properties (e.g. acid or base responsiveness), the chemical reactivity (e.g. the introduction of orthogonally reactive functional groups) or the biological properties (e.g. via grafting of adhesive peptides or targeting ligands) of the hydrogels. As a result of these limitations, there is increasing interest in polymers with similar (biological) properties that can be synthesized in a facile manner with improved control over the polymer functionality (16).

Poly(oligoethylene glycol methacrylate) (POEGMA)-based polymers (17) have been proposed to meet this need. POEGMA can be synthesized by facile free radical copolymerization (18-20) and has been demonstrated to serve as an effective PEG analogue (21), exhibiting analogous non-immunogenic, non-cytotoxic and protein repellent properties to PEG (22). Furthermore, any acrylate or methacrylate-based functional monomer can easily be copolymerized with oligoethylene glycol methacrylate (OEGMA) to impart any desired functionality directly via copolymerization at the magnitude desired within the polymer chain. A number of POEGMA-based hydrogels have been reported to-date (23-27); however, with the exception of a 4-arm PEG-b-POEGMA polymer reported by Fechler et. al, which undergoes physical gelation at the physiological temperature of 37° C. (28), none of these hydrogels are either injectable or degradable in vivo, which severely limits their potential clinical application.

Gelation kinetics and the final morphology of the hydrogel are often linked, given that rapid cross-linking reactions can induce gelation faster than the timescale required for diffusional mixing of precursor polymers. As a result, depending on the type of mechanical mixing used during the gel formation process, regions of local heterogeneity may form within the polymer matrices of these gels that scatter light (significantly affecting the utility of these gels in ophthalmic applications (49)), alter the diffusional properties of small molecules through the gel, and/or degrade the mechanical properties of the gel.

Temperature-Responsive Hydrogels

Temperature-responsive hydrogels have attracted significant interest in the context of their capacity to macroscopically change their dimensions and, as a result, pore sizes (used, for example, for the triggered release of therapeutics). [51, 52] as well as their hydrophobicity (used, for example, for reversible cell adhesion/detachment)[53-55] as a function of temperature. The most widely reported of such materials is poly(N-isopropylacrylamide) (PNIPAM), which shows a lower critical solution temperature (LCST) in aqueous media just below physiological temperature. [56] However, concerns regarding the acute toxicity of the monomer N-isopropylacrylamide (NIPAM) as well as the chronic toxicity of degradation products of PNIPAM in vivo have hampered clinical use.[57,58] In addition, changing the LCST by copolymerization of more or less hydrophilic monomers often results in broadening of the phase transition that is typically undesirable in switchable materials. In contrast, POEGMA polymers can be synthesized through facile free radical polymerization to display an LCST in aqueous media that is governed by the ethylene oxide chain length (n) of the oligo(ethylene glycol) methacrylate (OEGMA) monomer.[59,60] Through the statistical copolymerization of diethylene glycol methacrylate (M(EO)$_2$MA, n=2) and OEGMA$_{475}$ (n=8,9),[61-63] hydrogels can be prepared that display a volume phase transition temperature (VPTT) ranging anywhere from ~23° C. to ~90° C. while maintaining comparatively sharp transitions [64-68].

pH-Responsive Hydrogels pH-responsive hydrogels have attracted significant interest in the context of their capacity to sense (and actuate swelling changes) in different biological environments (e.g. lower pH values at infection or highly metabolically active sites such as tumors, protection of drugs in the acidic stomach environment and release where desired in the more basic intestine, etc.) In addition, the incorporation of charge inside hydrogels offers potential to significantly enhance the affinity of the hydrogel for charged bioactive agents (of the opposite charge to the charges in the hydrogel), improving their loading while slowing their release. In particular, amphoteric hydrogels that contain both positive and negative charged groups have attracted specific interest considering their charge distributions can mimic that of proteins; in this context, they have potential for controlled release of proteins without inducing protein denaturation as well as the potential to further reduce non-specific protein adsorption to materials (as demonstrated for a variety of zwitterionic materials such as poly(betaines)).

SUMMARY

The present disclosure relates to hydrogel compositions comprising precursor poly(oligoethylene glycol methacrylate) (POEGMA) polymers which have been functionalized with either nucleophilic or electrophilic moieties. In particular, in one embodiment, the hydrogel compositions all exhibit the desirable protein and cell-repellent properties of conventional PEG hydrogels while being injectable and chemically and mechanically tunable, enabling facile preparation of a range of hydrogels with targeted biomedical properties.

Accordingly, the present disclosure is directed to a hydrogel composition comprising,
a. a first precursor polymer which is a nucleophile-functionalized poly(oligoethylene glycol methacrylate) copolymer, and
b. a second precursor polymer which is an electrophile-functionalized poly(oligoethylene glycol methacrylate) copolymer, wherein the first and second precursor polymers are crosslinked through covalent bonds.

In another embodiment, the present disclosure is directed to a hydrogel composition comprising,
a. a first precursor polymer which is a hydrazide-functionalized poly(oligoethylene glycol methacrylate) copolymer, and
b. a second precursor polymer which is an aldehyde- and/or ketone-functionalized poly(oligoethylene glycol methacrylate) copolymer, wherein the first and second precursor polymers are crosslinked through hydrazone bonds.

In another embodiment, the present disclosure also includes a kit, comprising
a. a first precursor polymer which is a nucleophile-functionalized poly(oligoethylene glycol methacrylate) copolymer;
b. a second precursor polymer which is an electrophile-functionalized poly(oligoethylene glycol methacrylate) copolymer; and
c. instructions for use.

Further, the present disclosure also includes a double-barreled syringe, comprising,
a. a first precursor polymer which is a nucleophile-functionalized poly(oligoethylene glycol methacrylate) copolymer;
b. a second precursor polymer which is an electrophile-functionalized poly(oligoethylene glycol methacrylate) copolymer,
wherein, upon injection, the first and second precursor polymers form, in situ, the hydrogel composition.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 is a schematic representation illustrating the synthesis of a hydrogel composition of the disclosure.

FIG. 2 shows the physiochemical characterization of hydrogels of the disclosure. A) Equilibrium mass-based swelling ratio as a function of the precursor concentration and the degree of functionalization. B) Degradation kinetics as measured in 100 mM HCl as a function of precursor concentration and the degree of functionalization. C) Elastic storage modulus as a function of precursor degree of functionalization. D) Elastic storage modulus as a function of precursor concentration. E-J) Photographs of the physical appearance of the various hydrogels directly after.

Figure 6:
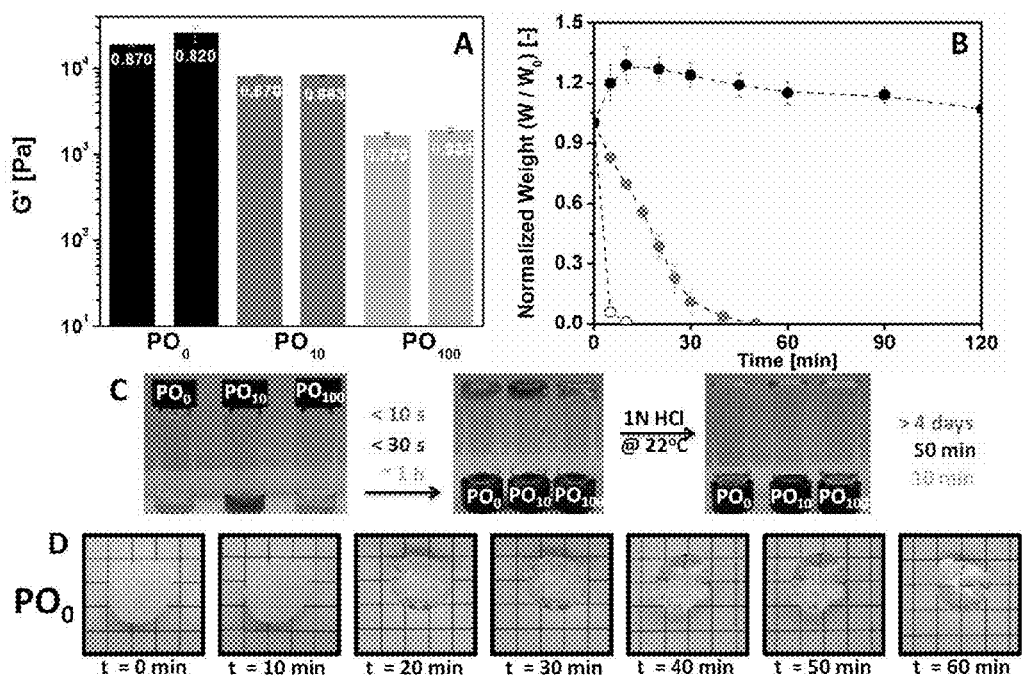

FIG. 6 are graphs showing A) Shear storage modulus (G') of hydrogels of the disclosure measured directly after preparation and after swelling for 24 hours. B) Degradation profiles of hydrogels of the disclosure. C) Gelation and degradation of hydrogels of the disclosure. D) Optical appearance of a hydrogel of the disclosure over the first 60 minutes of incubation.

Figure 7:
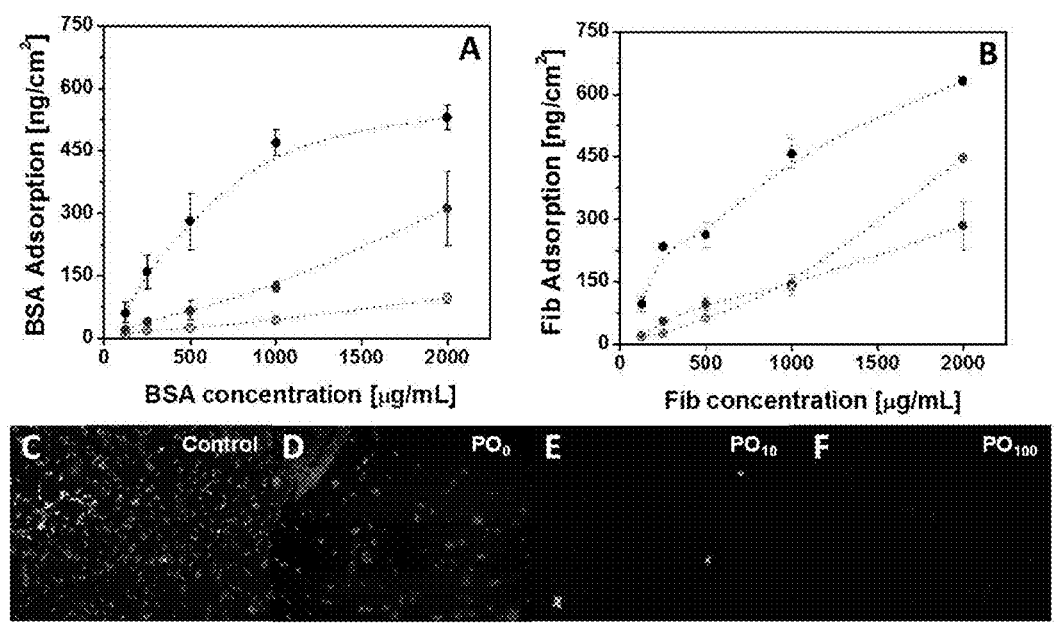

FIG. 7 shows A) Bovine serum albumin (BSA) and B) fibrinogen (Fib) adsorption onto hydrogels of the disclosure as function of the protein concentration in the loading solution. (C-F) 3T3 mouse fibroblast adhesion onto C) a tissue culture polystyrene control, and D) hydrogels of the disclosure.

Figure 8:
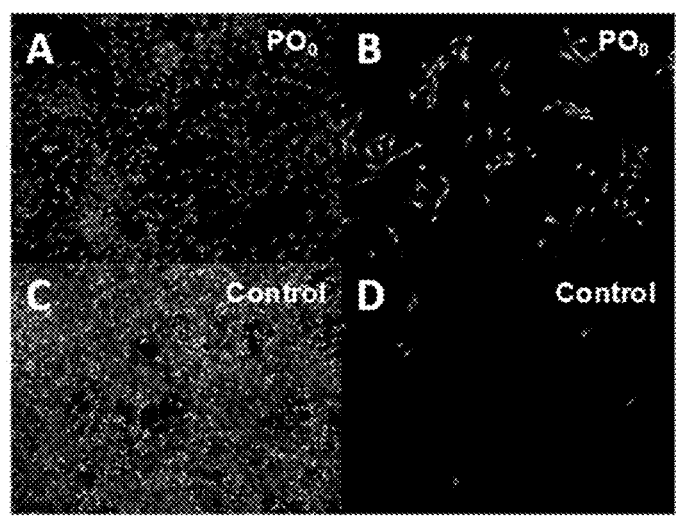

FIG. 8 shows cells recovered following delamination from a hydrogel of the disclosure interface (A,B) and tissue culture polystyrene surface (C,D) following trypsin treatment (A,C) and following thermal treatment (B,D).

Figure 9:
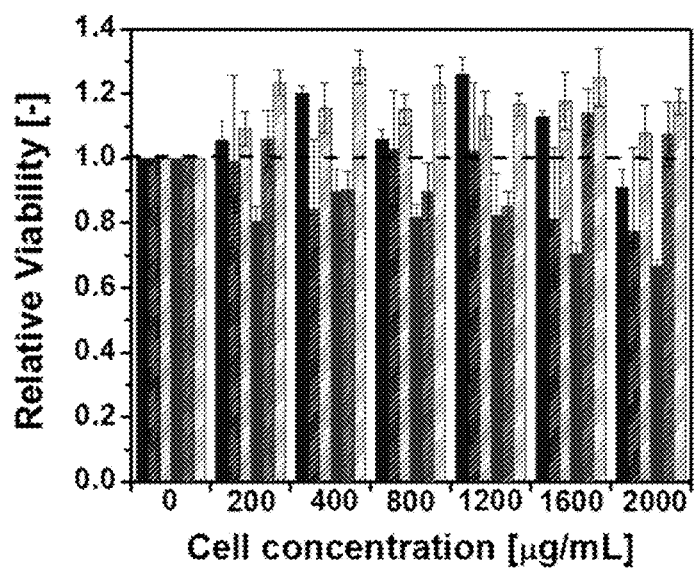

FIG. 9 is a graph which shows the cytotoxicity of precursors and degradation products via a MTT assay on 3T3 mouse fibroblasts.

Figure 10:
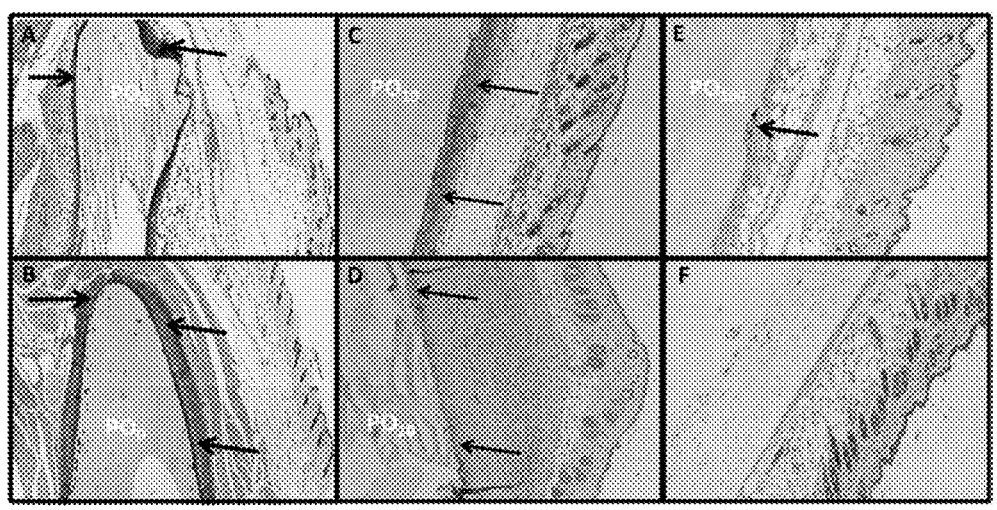

FIG. 10 shows the histological sections of stained subcutaneous tissue samples following injection of hydrogels of the disclosure.

Figure 11:
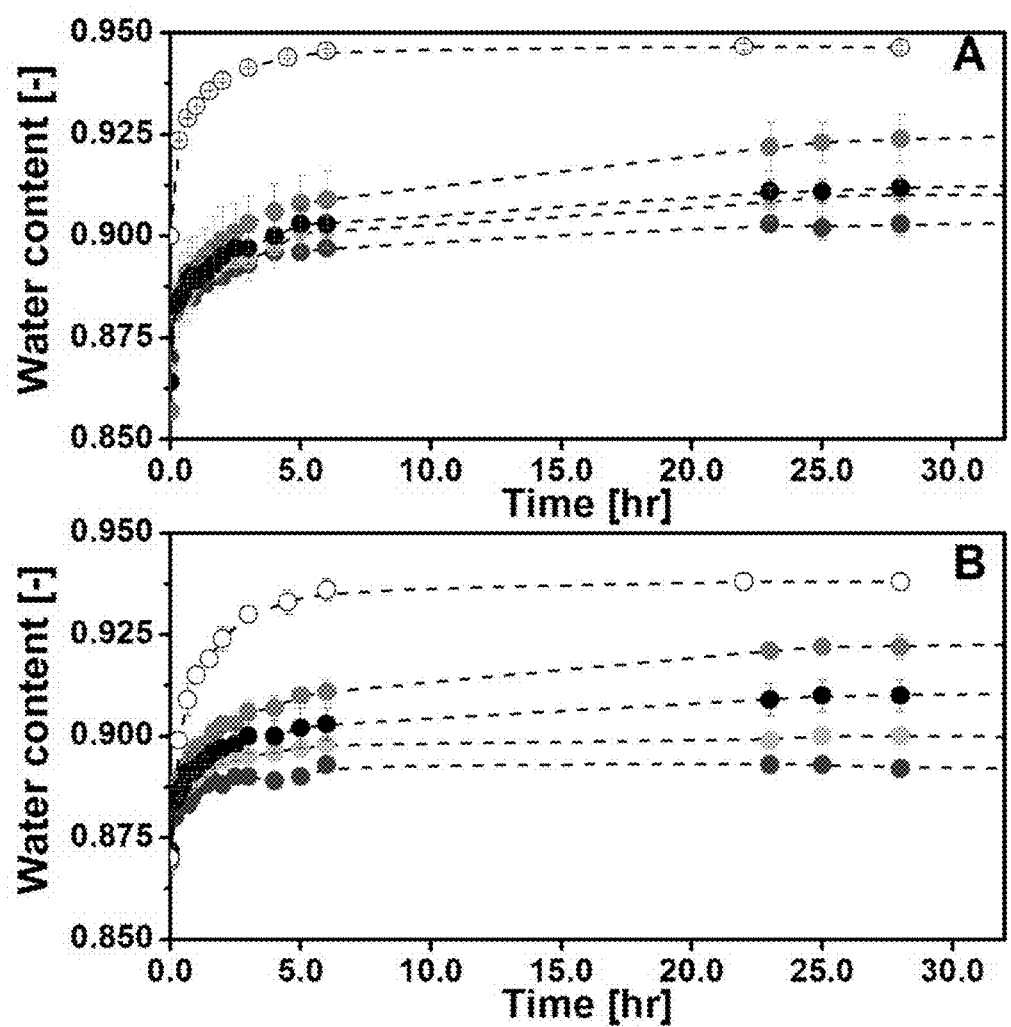

FIG. 11 are graphs showing the swelling kinetics of hydrogels of the disclosure.

Figure 12:
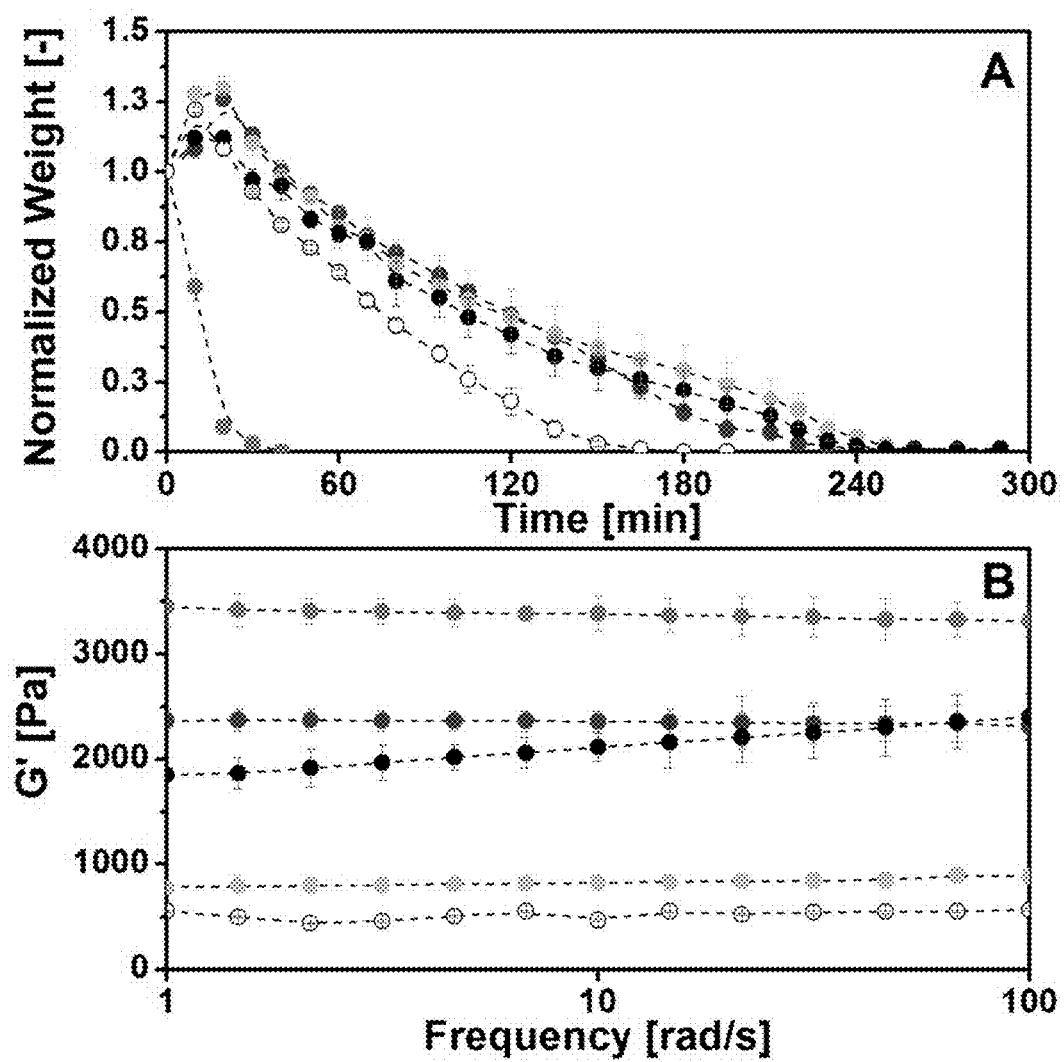

FIG. 12 are graphs showing the degradation kinetics (A) and elastic storage modulus (B) of hydrogels of the disclosure.

Figure 13:
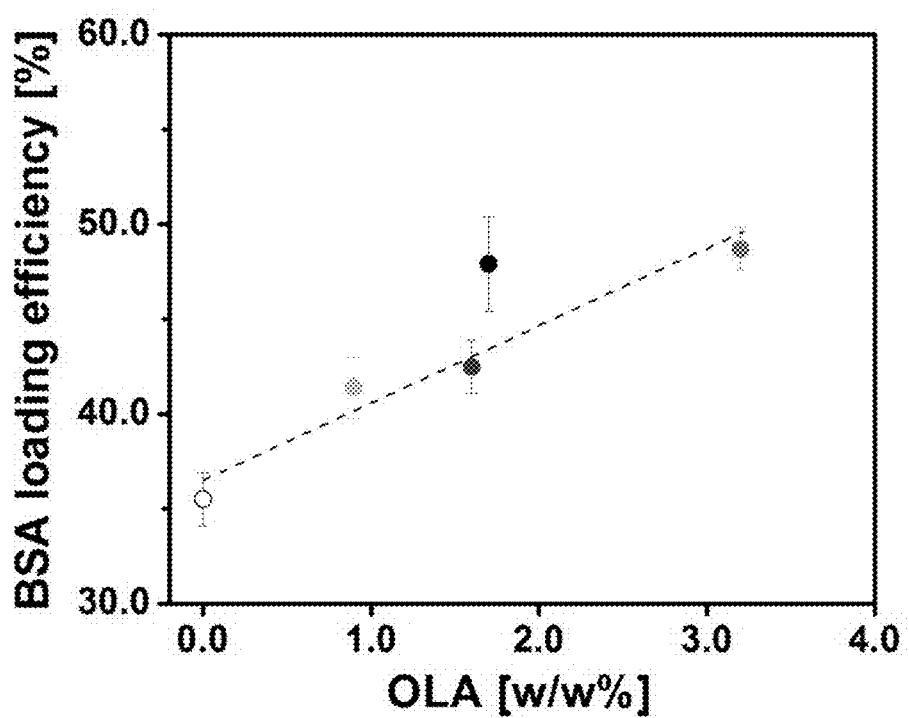
Figure 14:
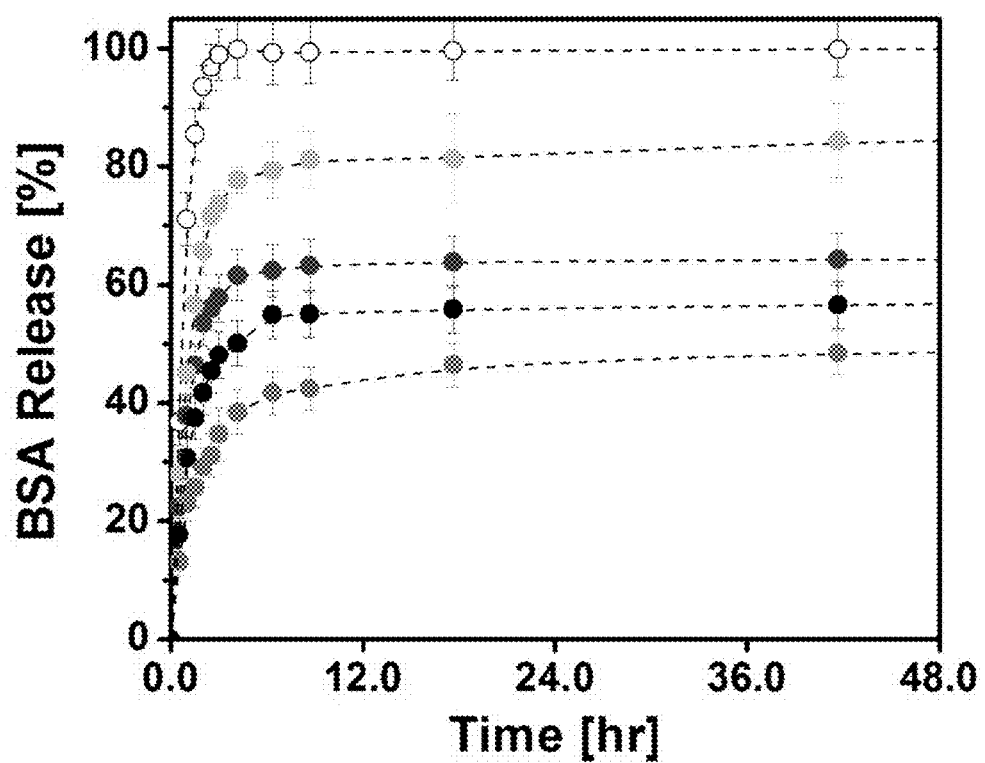

FIG. 13 is a graph showing the bovine serum albumin (BSA) loading efficiency of hydrogels of the disclosure FIG. 14 is a graph showing cumulative bovine serum albumin (BSA) release over the first 2 days hydrogels of the disclosure.

Figure 15:
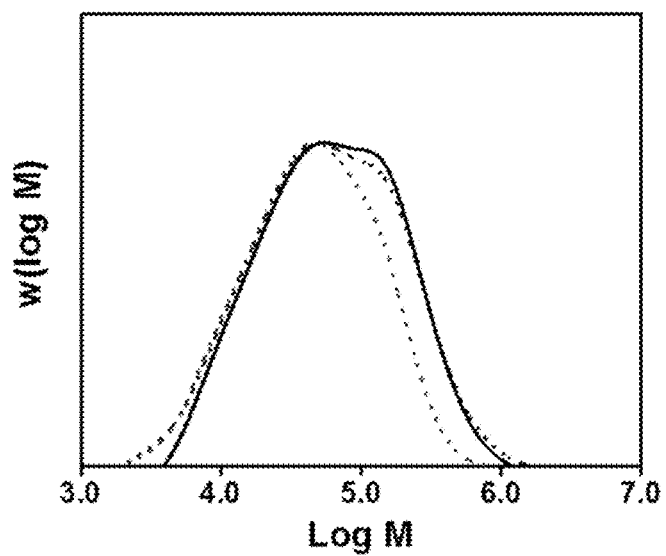

FIG. 15 is a graph showing the molecular weight distributions of hydrogels of the disclosure and the hydrogel degradation products (black) as measured by aqueous size exclusion chromatography.

Figure 16:
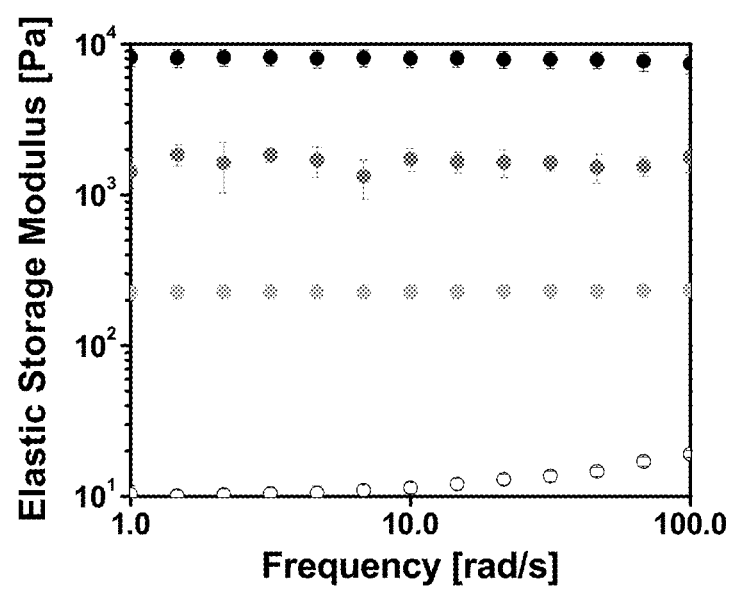

FIG. 16 is a graph showing the elastic storage modulus of hydrogels of the disclosure.

Figure 17:
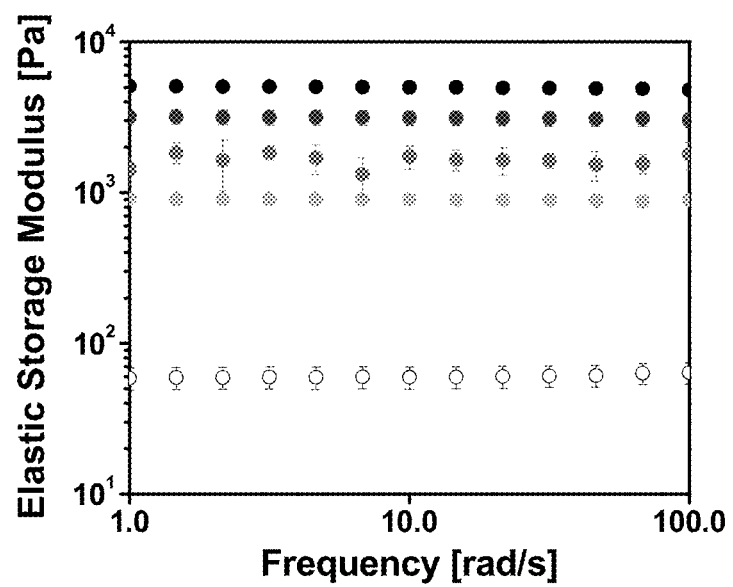

FIG. 17 is a graph showing the elastic storage modulus of hydrogels of the disclosure.

Figure 18:
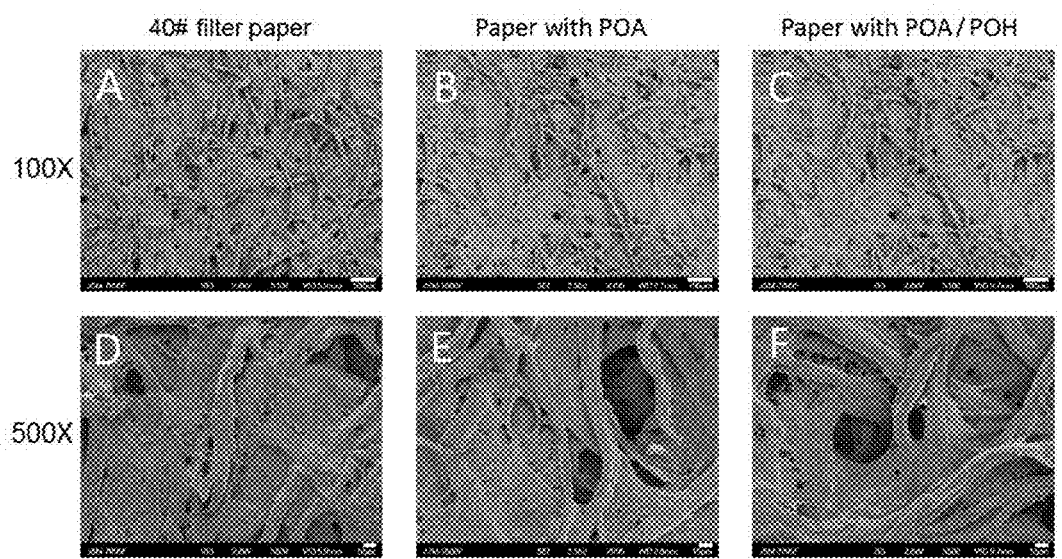

FIG. 18 shows scanning electron microscopy (SEM) images of 40# filter paper (A,D) and filter paper coated with a hydrogel of the disclosure alone (B,E) or with precursors sequentially (C,F) at 100× (A-C) and 500× (D-F) magnification.

Figure 19:
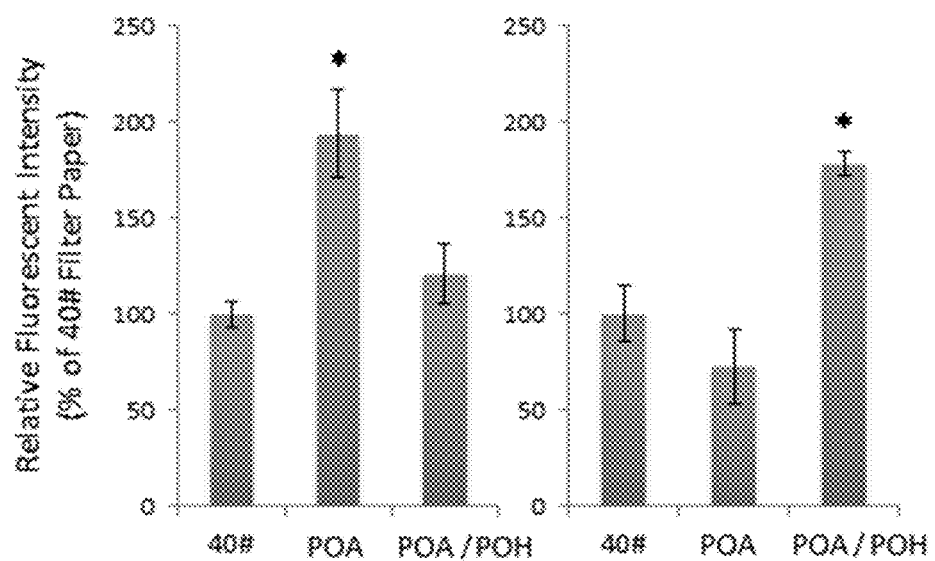

FIG. 19 are graphs showing the relative density of aldehyde and hydrazide groups on the paper with or without precursor coating.

Figure 20:
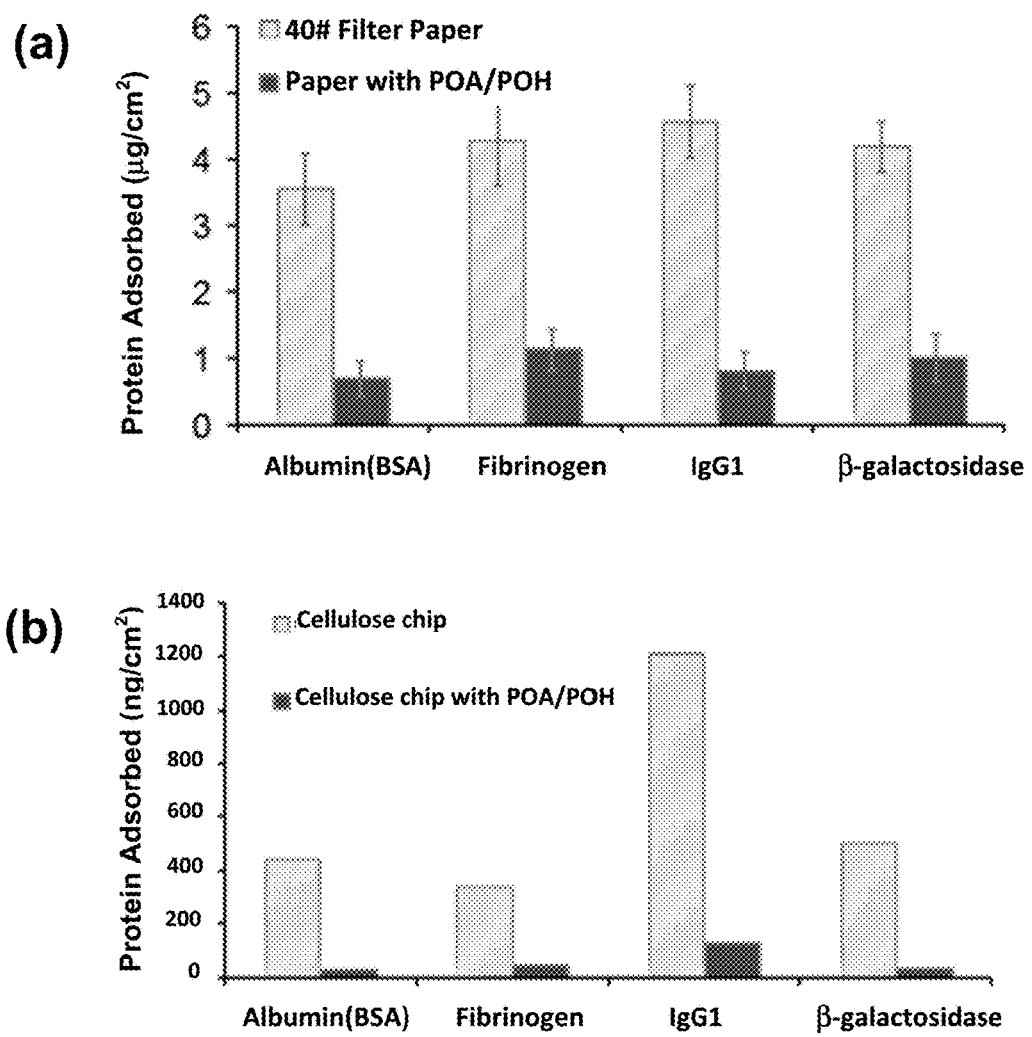

FIG. 20 are graphs showing a comparison of protein adsorption between unmodified and hydrogel modified surfaces for (a) Whatman 40# filter paper (porous cellulose substrate) and (b) cellulose-coated quartz crystal microbalance chip (solid cellulose substrate).

Figure 21:
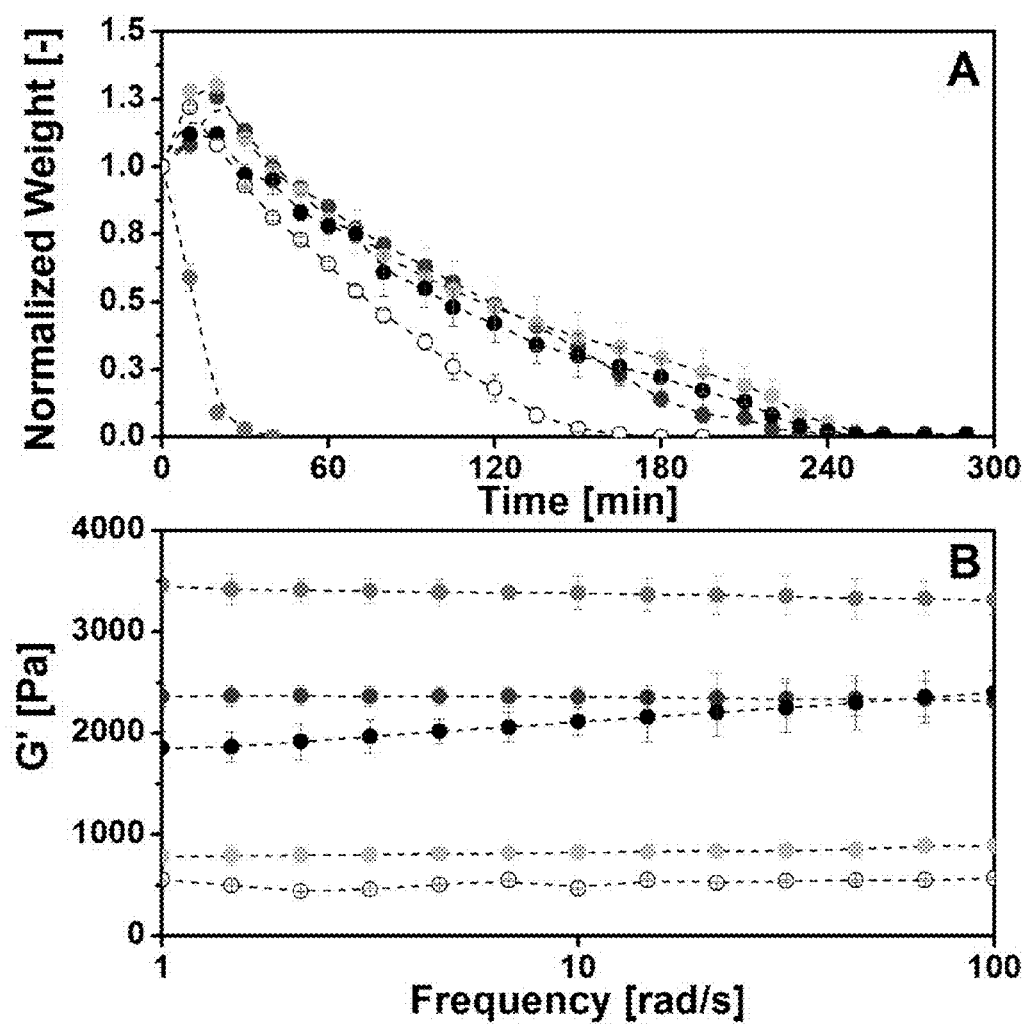

FIG. 21 are graphs showing the decoupling of gel degradation kinetics and gel mechanics via dual cross-linking mechanism: (A) gravimetric swelling/degradation in accelerated conditions; (B) elastic storage modulus G'.

Figure 22:
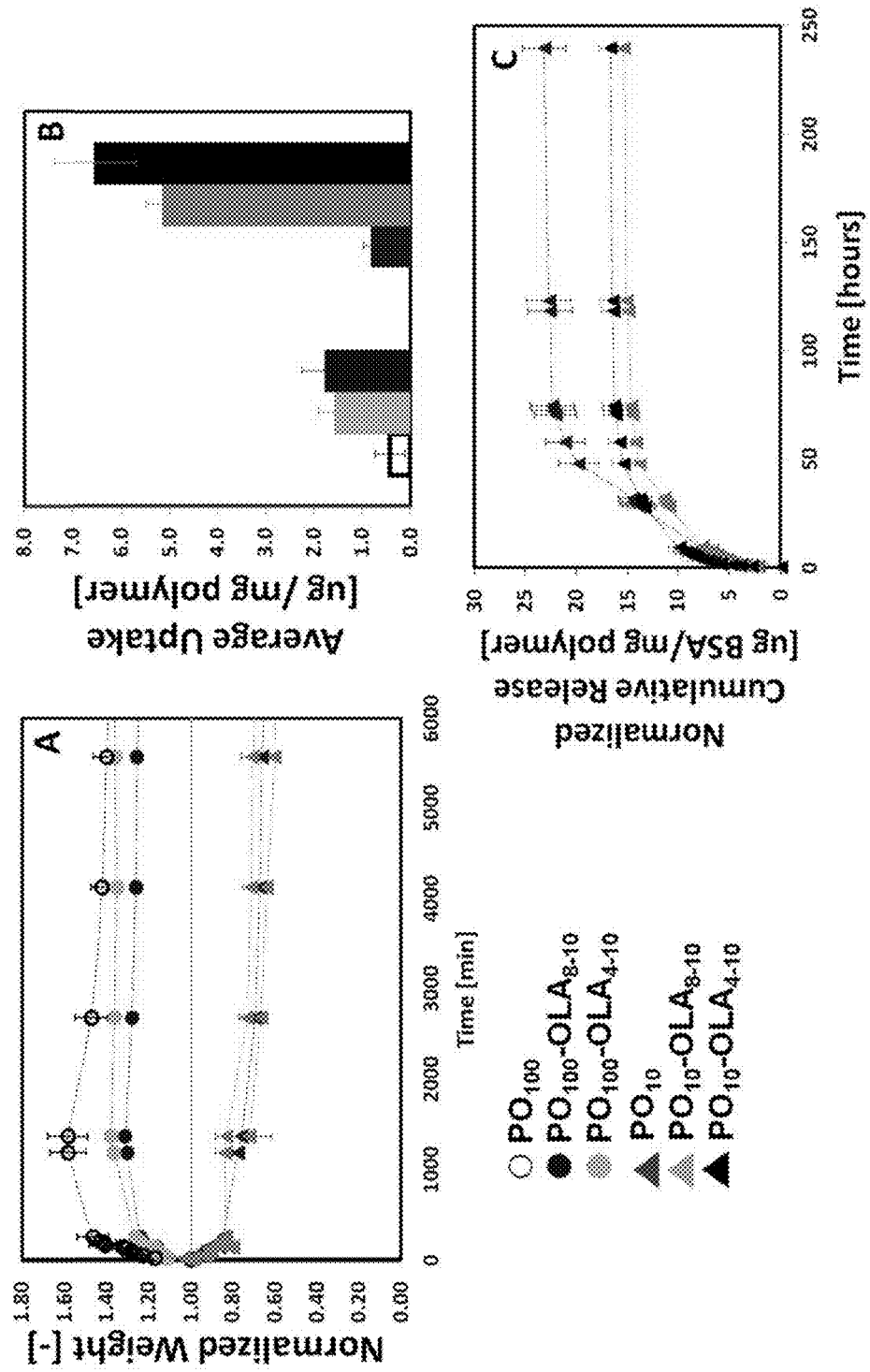

FIG. 22 shows (A) swelling kinetics of a hydrogel of the disclosure; (B) BSA protein affinity to a hydrogel of the disclosure; (C) BSA protein release from a hydrogel of the disclosure.

Figure 23:
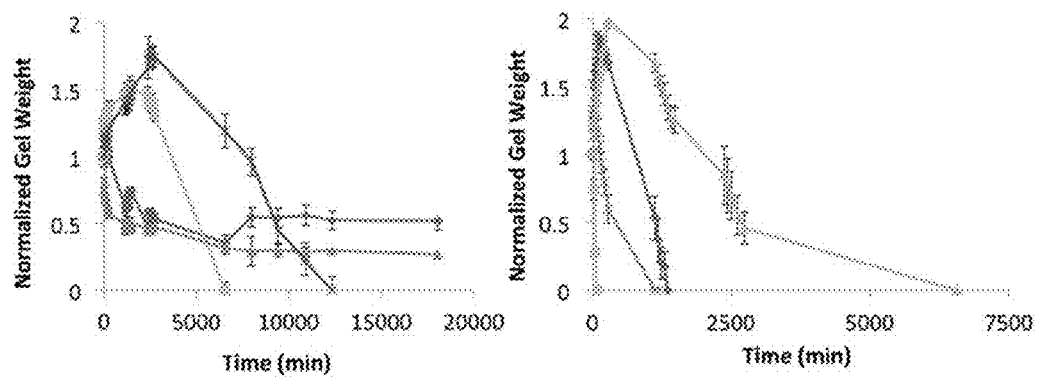

FIG. 23 are graphs showing the degradation profiles of hydrogels of the disclosure.

Figure 24:
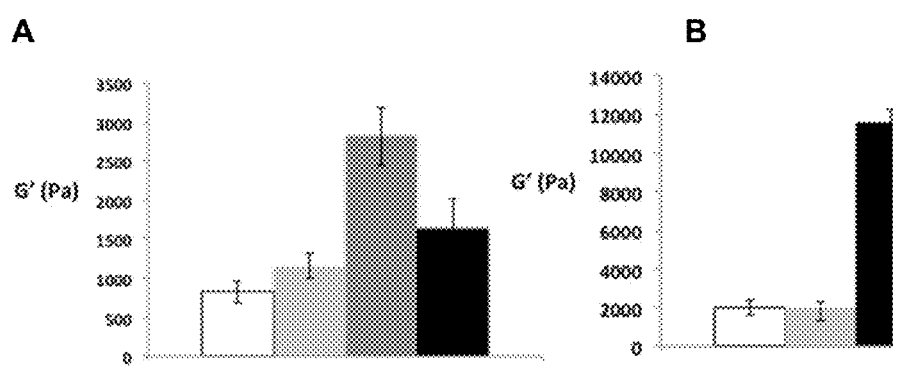

FIG. 24 are graphs showing the average elastic storage moduli (G') of hydrogels of the disclosure.

Figure 25:
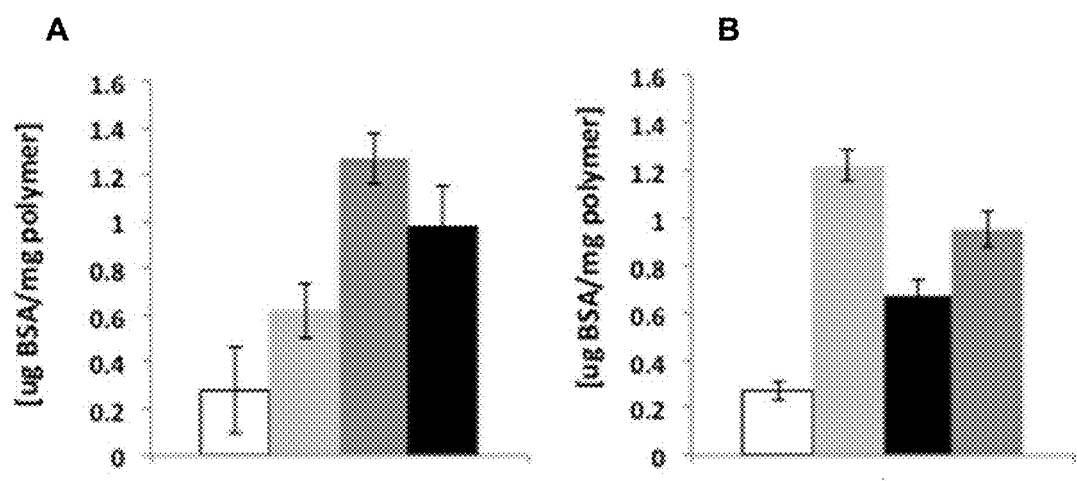

FIG. 25 are graphs showing BSA uptake into hydrogels of the disclosure.

Figure 26:
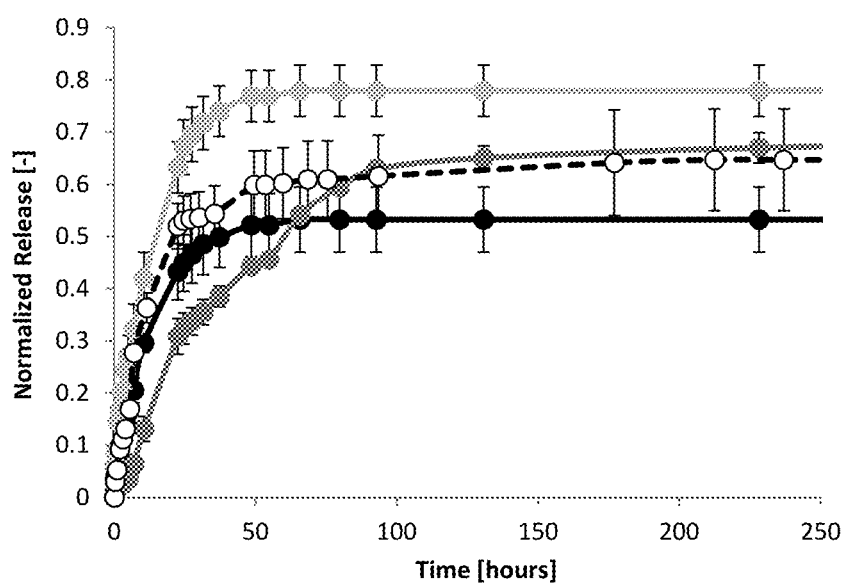

FIG. 26 shows protein release (fluorescein-labeled BSA) from hydrogels of the disclosure.

Figure 27:
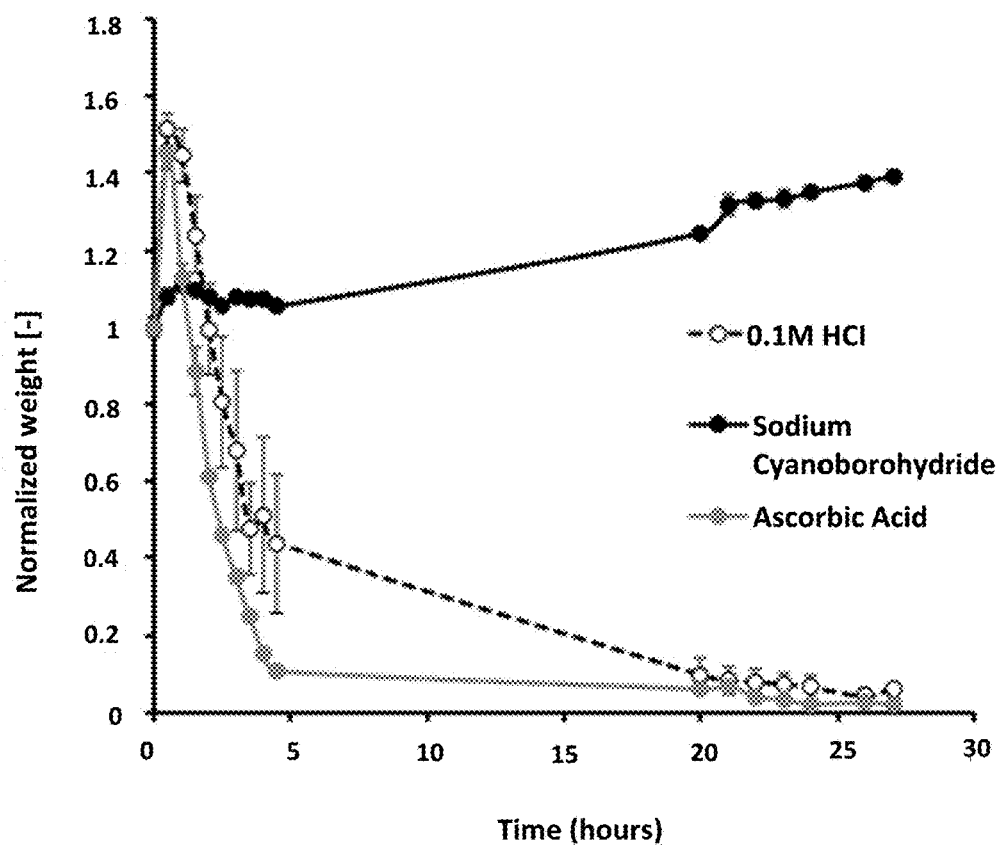

FIG. 27 illustrates a mass-based degradation assay of a hydrogel of the disclosure untreated, reduced with ascorbic acid, or reduced with sodium cyanoborohydride.

Figure 28:
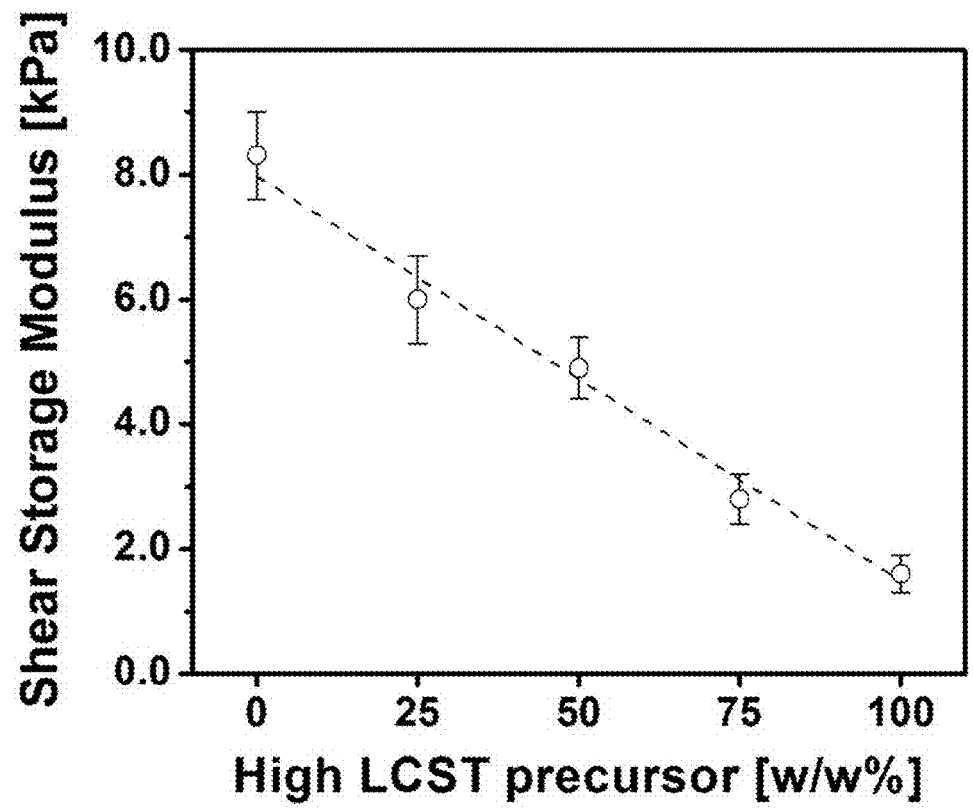

FIG. 28 is a graph showing the average shear storage moduli of a swollen hydrogel of the disclosure.

Figure 29:
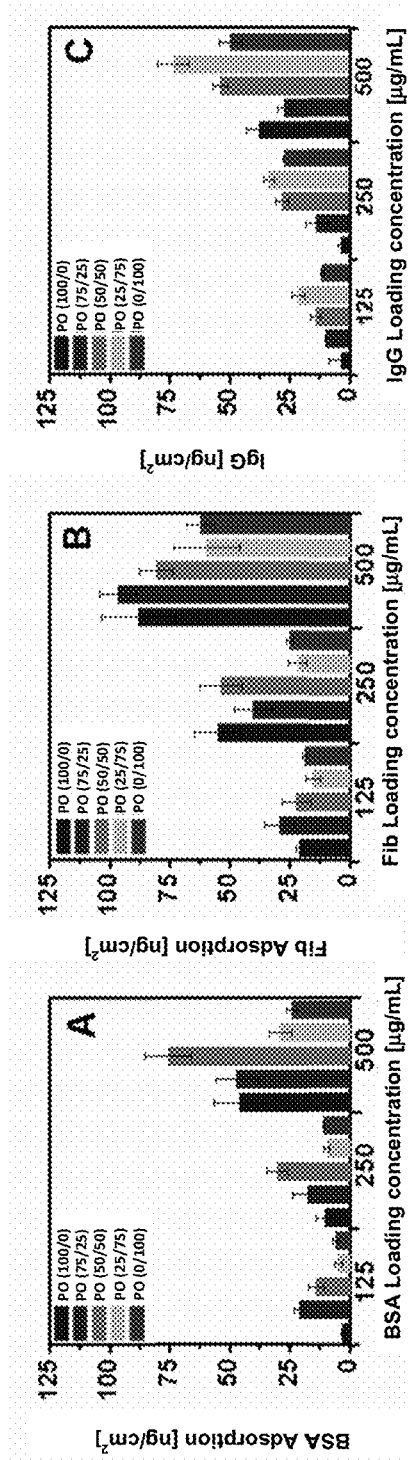

FIG. 29 are bar graphs showing (A) Bovine serum albumin (BSA), (B) fibrinogen (Fib), and (C) immunoglobulin G (IgG) uptake in hydrogels of the disclosure.

Figure 30:
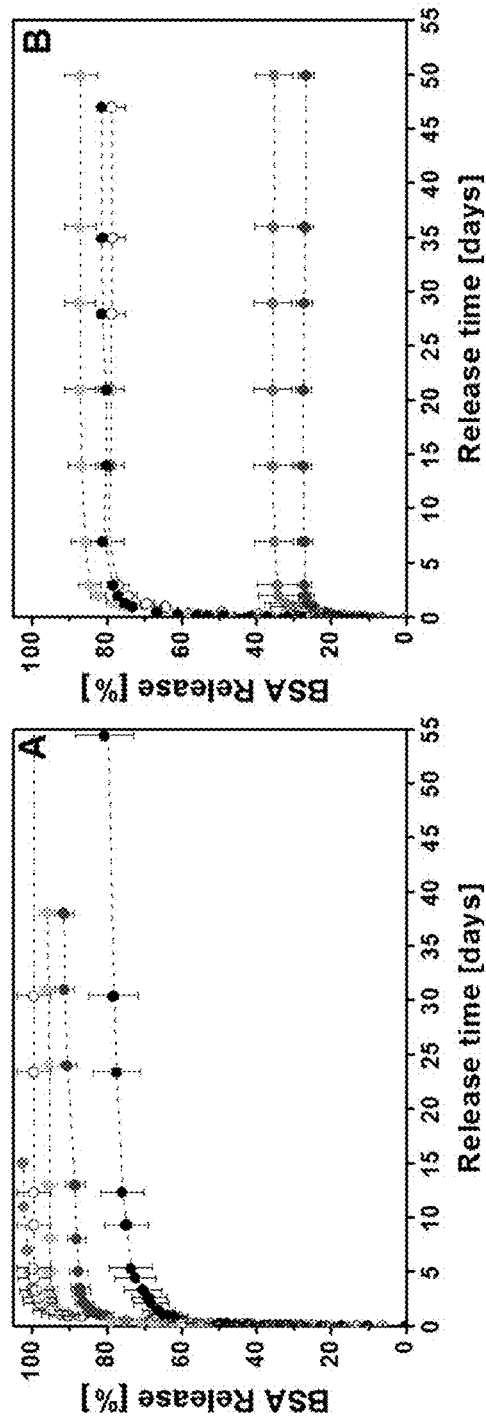

FIG. 30 are graphs showing BSA release kinetics for hydrogels of the disclosure.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

As used in this application, the singular forms "a", "an" and "the" include plural references unless the content clearly dictates otherwise. For example, an embodiment including "the polymer" should be understood to present certain aspects with one polymer or two or more additional polymers.

In embodiments comprising an "additional" or "second" component, such as an additional or second polymer, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "alkyl" as used herein, whether it is used alone or as part of another group, means straight or branched chain, saturated alkyl groups, and includes for example, methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like. The term $C_{1-6}$alkyl means an alkyl group having 1, 2, 3, 4, 5, or 6 carbon atoms.

The term "alkylene" as used herein, whether alone or as part of another group, means an alkyl group that is bivalent; i.e. that is substituted on two ends with another group. The term $C_{0-2}$alkylene means an alkylene group having 0, 1 or 2 carbon atoms. It is an embodiment of the application that, in the alkylene groups, one or more, including all, of the hydrogen atoms are optionally replaced with F or $^2H$.

The term "aryl" as used herein means a monocyclic, bicyclic or tricyclic aromatic ring system containing, depending on the number of atoms in the rings, for example from 6 to 10 carbon atoms, and at least 1 aromatic ring and includes, but is not limited to, phenyl, naphthyl, anthracenyl, 1,2-dihydronaphthyl, 1,2,3,4-tetrahydronaphthyl, fluorenyl, indanyl, indenyl and the like.

The term "heteroaryl" as used herein refers to cyclic groups that contain at least one aromatic ring and at least one heteroatom, such as N, O and/or S. The term $C_{5-10}$heteroaryl means an aryl group having 5, 6, 7, 8, 9 or 10 atoms, in which at least one atom is a heteroatom, such as N, O and/or S, and includes, but is not limited to, thienyl, furyl, pyrrolyl, pyrididyl, indolyl, quinolyl, isoquinolyl, tetrahydroquinolyl, benzofuryl, benzothienyl and the like.

The term "polymerizable" as used herein refers to the property of individual monomers to react with other monomers, whether the same or different, under appropriate conditions to yield polymers The term "reducing agent" as used herein means any compound or combination of compounds that reduces a desired functional group. A reducing agent results in the overall addition of electrons, or in the case of organic chemistry, hydrogen atoms to the functional group.

The term "derivative" as used herein refers to a substance which comprises the same basic carbon skeleton and functionality as the parent compound, but can also bear one or more substituents or substitutions of the parent compound. For example, alkyl derivatives of oligoethylene glycol methacrylate would include any compounds in which an alkyl group is substituted on the oligoethylene glycol methacrylate backbone.

The term "precursor polymer" as used herein refers to an oligoethylene glycol methacrylate-based copolymer that has been modified to contain a reactive functional group, for example, a nucleophilic or electrophilic moiety. In one embodiment for example, a precursor polymer of the present disclosure comprises a hydrazide reactive group, or an aldehyde and/or ketone reactive functional group on a poly(oligoethylene glycol methacrylate) polymer.

The term "copolymer" as used herein is defined as a polymer derived from two or more different monomers. In one embodiment for example, a copolymer of the present disclosure includes a co-polymer of oligoethylene glycol methacrylate and acrylic acid. Other co-polymers include, for example, a co-polymer of oligoethylene glycol methacrylate and N-(2,2-dimethoxyethyl)methacrylamide (DMEMAm).

The term "nucleophile-functionalized" as used herein refers to a copolymer comprised of at least repeating units of oligoethylene glycol methacrylate in which a part of the copolymer has been functionalized with a nucleophilic moiety which can react with an electrophile or electrophilic moiety to form covalent cross-linked bonds.

The term "electrophile-functionalized" as used herein refers to a copolymer comprised of at least repeating units of oligoethylene glycol methacrylate in which a part of the copolymer has been functionalized with an electrophilic moiety which can react with a nucleophile or nucleophilic moiety to form covalent cross-linked bonds.

The term "polymeric backbone" as used herein refers to the main chain of a suitable polymer comprising a series of covalently bonded atoms that together create the continuous chain (straight or branched) of the polymeric molecule.

The term "crosslinked" or "crosslink" as used herein is defined as a bond that links a first precursor polymer to a second precursor polymer. The bonds can be covalent bonds. For example, the "crosslink" is a reversible hydrazone bond formed between a reactive hydrazide, and aldehyde and/or ketone functional groups.

The term "hydrogel" as used herein refers to a polymeric material that exhibits the ability to swell and retain a significant fraction of water within its structure, without dissolving in water.

The term "w/w" as used herein means the number of grams of solute in 100 g of solution.

The term "w/v" as used herein refers to the number of grams of solution in 100 mL of solvent.

II. Compositions and Kits of the Application

The present disclosure is generally directed to a hydrogel composition comprising a first precursor polymer, which is a nucleophile-functionalized poly(oligoethylene glycol methacrylate) copolymer and a second precursor polymer, which is an electrophile-functionalized poly(oligoethylene glycol methacrylate) copolymer, wherein the first and second precursor polymers are crosslinked through covalent bonds by reaction between the nucleophilic and electrophilic moieties. In one embodiment, the poly(oligoethyle glycol methacrylate) hydrogels of the disclosure are chemically and mechanically tunable, and are also injectable.

Accordingly, the present disclosure is directed to a hydrogel composition comprising,
  c. at least one first precursor polymer which is a nucleophile-functionalized poly(oligoethylene glycol methacrylate) copolymer, and
  d. at least one second precursor polymer which is an electrophile-functionalized poly(oligoethylene glycol methacrylate) copolymer, wherein the first and second precursor polymers are crosslinked through covalent bonds by reaction between the nucleophilic and electrophilic moieties.

In another embodiment, the nucleophile-functionalized poly(oligoethylene glycol methacrylate) copolymer comprises a nucleophilic moiety which is a hydrazine or amine derivative, a carbonyl hydrate, an alcohol, cyanohydrin or cyanohydrin derivative, a thiol or thiol derivative, or a phosphorus ylide or derivative thereof. In another embodiment, the nucleophilic moiety is a hydrazide.

In another embodiment, the electrophile-functionalized poly(oligoethylene glycol methacrylate) copolymer comprises an electrophilic moiety which is an aldehyde, a ketones, a carboxylic acid, an ester, an amides, a maleimide, an acyl (acid) chloride, an acid anhydride, or an alkene or derivatives thereof. In another embodiment, the electrophilic moiety is an aldehyde or a ketone.

In another embodiment, the hydrogel composition comprises two or more first precursor polymers. In another embodiment, the hydrogel composition comprises two or more second precursor polymers.

In another embodiment, the present disclosure is directed to a hydrogel composition, comprising,
  a. at least one first precursor polymer which is a hydrazide-functionalized poly(oligoethylene glycol methacrylate) copolymer, and
  b. a second precursor polymer which is an aldehyde- and/or ketone-functionalized poly(oligoethylene glycol methacrylate) copolymer,
  wherein the first and second precursor polymers are crosslinked through hydrazone bonds.

In an embodiment, the first and second precursor polymers have a molecular weight which is less than the molecular weight cut-off for renal (kidney) clearance. In another embodiment, the first and second precursor polymers have a molecular weight which is less than about 50 kDa, or less than about 40 kDa. In another embodiment, the first and second precursor polymers have a molecular weight of about 10 kDa to about 50 kDa, or about 20 kDa to about 50 kDa.

In one embodiment, the first precursor polymer is a copolymer comprising monomeric units of:

a. a first monomer which is oligoethylene glycol methacrylate, or a derivative thereof; and
b. at least one second polymerizable monomer which is functionalized, or is capable of being functionalized, with a nucleophilic moiety.

In an embodiment, the first monomer has the structure of the formula (I):

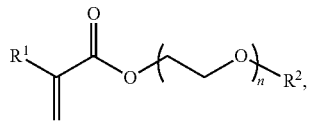

wherein
$R^1$ is H, $(C_1-C_{10})$alkyl or $(C_2-C_{10})$alkynyl;
$R^2$ is H, $(C_1-C_{10})$alkyl, $(C_2-C_{10})$alkynyl, $-(C_0-C_4)$-alkylene-$(C_6-C_{10})$aryl, $-(C_0-C_4)$-alkylene-$(C_5-C_{10})$heteroaryl, $-C(O)NR'$ or $-C(O)OR'$, wherein R' is H or $(C_1-C_6)$alkyl, and
n is any integer between 6 and 30.

In another embodiment, $R^1$ is H, $(C_1-C_6)$alkyl or $(C_2-C_6)$alkynyl. In a further embodiment, $R^1$ is H or $(C_1-C_4)$alkyl. In another embodiment, $R^1$ is H or $CH_3$. In another embodiment, $R^1$ is $CH_3$. In one embodiment, $R^1$ is H.

In another embodiment, $R^2$ is H, $(C_1-C_6)$alkyl, $(C_2-C_6)$alkynyl, $-(C_0-C_2)$-alkylene-$(C_6-C_{10})$aryl, $-C(O)NR'$ or $-C(O)OR'$, wherein R' is H or $(C_1-C_4)$alkyl. In a further embodiment, $R^2$ is H, $(C_1-C_4)$alkyl, $-(C_0-C_2)$-alkylene-phenyl, $-C(O)NR'$ or $-C(O)OR'$, wherein R' is H or $(C_1-C_4)$alkyl. In another embodiment, $R^2$ is H or $CH_3$.

In one embodiment, n is any integer between 6 and 20, or between 6 and 12.

In another embodiment, the second polymerizable monomer is functionalized, or is capable of being functionalized, with a nucleophilic moiety, wherein the nucleophilic moiety is hydrazine or amine derivative, a carbonyl hydrate, an alcohol, cyanohydrin or cyanohydrin derivative, a thiol or thiol derivative, or a phosphorus ylide or derivatives thereof. In another embodiment, the nucleophilic moiety is a hydrazide.

In another embodiment, the first precursor polymer is a copolymer comprising monomeric units of:
a. a first monomer which is oligoethylene glycol methacrylate, or a derivative thereof; and
b. at least one second polymerizable monomer which is functionalized, or is capable of being functionalized, with a hydrazide moiety.

In one embodiment, the second polymerizable monomer has a carboxylic acid moiety, as the carboxylic acid can be functionalized to a hydrazide moiety. In another embodiment, the second polymerizable monomer is acrylic acid or a derivative thereof, methacrylic acid, itaconic acid, fumaric acid, maleic acid, or vinylacetic acid. In a further embodiment, the second monomer is acrylic acid or a derivative thereof. In another embodiment, the second polymerizable moiety is vinyl alcohol or allylic alcohol, which can be functionalized to a hydrazide moiety. In another embodiment, the second polymerizable moiety contains a nucleophilic moiety, such as a hydrazide moiety. In one embodiment, the second polymerizable moiety is acrylic acid functionalized with a hydrazide moiety

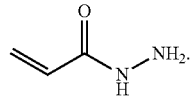

In another embodiment, the second polymerizable moiety of the first precursor polymer is

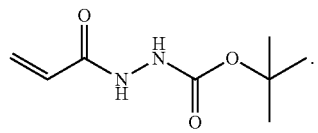

In another embodiment of the disclosure, the first precursor polymer is a co-polymer which further comprises a third monomer which has the structure of the formula (II):

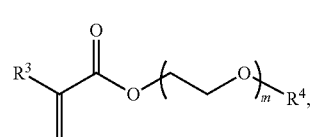

wherein
$R^3$ is H, $(C_1-C_{10})$alkyl or $(C_2-C_{10})$alkynyl;
$R^4$ is H, $(C_1-C_{10})$alkyl, $(C_2-C_{10})$alkynyl, $-(C_0-C_4)$-alkylene-$(C_6-C_{10})$aryl, $-(C_0-C_4)$-alkylene-$(C_5-C_{10})$heteroaryl, $-C(O)NR'$ or $-C(O)O-R'$, wherein R' is H or $(C_1-C_6)$alkyl, and
m is any integer between 3 and 5.

In another embodiment, $R^3$ is H, $(C_1-C_6)$alkyl or $(C_2-C_6)$alkynyl. In a further embodiment, $R^3$ is H or $(C_1-C_4)$alkyl. In another embodiment, $R^3$ is H or $CH_3$. In another embodiment, $R^3$ is $CH_3$. In one embodiment, $R^3$ is H.

In another embodiment, $R^4$ is H, $(C_1-C_6)$alkyl, $(C_2-C_{16})$alkynyl, $-(C_0-C_4)$-alkylene-$(C_6-C_{10})$aryl, $-C(O)NR'$ or $-C(O)O-R'$, wherein R' is H or $(C_1-C_4)$alkyl. In a further embodiment, $R^4$ is H, $(C_1-C_4)$alkyl, $-(C_0-C_4)$-alkylene-phenyl, $-C(O)NR'$ or $-C(O)O-R'$, wherein R' is H or $(C_1-C_4)$alkyl. In a further embodiment, and $R^4$ is H or $CH_3$.

In another embodiment of the disclosure, the second precursor polymer is a copolymer comprising monomeric units of:
a. a first monomer which is oligoethylene glycol methacrylate, or a derivative thereof; and
b. a second polymerizable monomer which is functionalized, or is capable of being functionalized, with an electrophilic moiety.

In another embodiment, the second polymerizable monomer is functionalized, or is capable of being functionalized, with an electrophilic moiety, wherein the electrophilic moiety is an aldehyde, a ketones, a carboxylic acid, an ester, an amides, a maleimide, an acyl (acid) chloride, an acid anhydride, or an alkene or derivatives thereof. In another embodiment, the electrophilic moiety is an aldehyde or a ketone moiety.

In an embodiment, the second precursor polymer is a copolymer comprising monomeric units of:
a. a first monomer which is oligoethylene glycol methacrylate, or a derivative thereof; and b. a second polymerizable monomer which is functionalized, or is capable of being functionalized, with an electrophilic moiety, in which the electrophilic moiety is an aldehyde or a ketone moiety.

In an embodiment, the first monomer has the structure of the formula (I):

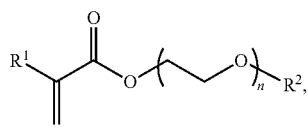

wherein
$R^1$ is H, $(C_1\text{-}C_{10})$alkyl or $(C_2\text{-}C_{10})$alkynyl;
$R^2$ is H, $(C_1\text{-}C_{10})$alkyl, $(C_2\text{-}C_{10})$alkynyl, —$(C_0\text{-}C_4)$-alkylene-$(C_6\text{-}C_{10})$aryl, —$(C_0\text{-}C_4)$-alkylene-$(C_5\text{-}C_{10})$heteroaryl, —C(O)NR' or —C(O)OR', wherein R' is H or $(C_1\text{-}C_6)$alkyl, and
n is any integer between 6 and 30.

In another embodiment, $R^1$ is H, $(C_1\text{-}C_6)$alkyl or $(C_2\text{-}C_6)$alkynyl. In a further embodiment, $R^1$ is H or $(C_1\text{-}C_4)$alkyl. In another embodiment, $R^1$ is H or $CH_3$. In another embodiment, $R^1$ is $CH_3$. In one embodiment, $R^1$ is H.

In another embodiment, $R^2$ is H, $(C_1\text{-}C_6)$alkyl, $(C_2\text{-}C_6)$alkynyl, —$(C_0\text{-}C_2)$-alkylene-$(C_6\text{-}C_{10})$aryl, —C(O)NR' or —C(O)OR', wherein R' is H or $(C_1\text{-}C_4)$alkyl. In a further embodiment, $R^2$ is H, $(C_1\text{-}C_4)$alkyl, —$(C_0\text{-}C_2)$-alkylenephenyl, —C(O)NR' or —C(O)OR', wherein R' is H or $(C_1\text{-}C_4)$alkyl. In a further embodiment, and $R^2$ is H or $CH_3$.

In one embodiment, n is any integer between 6 and 20, or between 6 and 12.

In an embodiment, the second polymerizable monomer is functionalized with an acetal moiety or a ketal moiety, as these moieties can be converted, after polymerization, to aldehyde or ketone moieties. In a further embodiment, the second polymerizable monomer is N-(2,2-dimethoxyethyl)methacrylamide (DMEMAm), allylic aldehyde or (N-((2-methyl-1,3-dioxolan-2-yl)methyl)methacrylamide).

In another embodiment of the disclosure, the second precursor polymer is a co-polymer which further comprises a third monomer which has the structure of the formula (II):

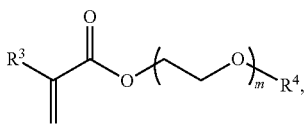

wherein
$R^3$ is H, $(C_1\text{-}C_{10})$alkyl or $(C_2\text{-}C_{10})$alkynyl;
$R^4$ is H, $(C_1\text{-}C_{10})$alkyl, $(C_2\text{-}C_{10})$alkynyl, —$(C_0\text{-}C_4)$-alkylene-$(C_6\text{-}C_{10})$aryl, —$(C_0\text{-}C_4)$-alkylene-$(C_5\text{-}C_{10})$heteroaryl, —C(O)NR' or —C(O)O—R', wherein R' is H or $(C_1\text{-}C_6)$alkyl, and
m is any integer between 3 and 5.

In another embodiment, $R^3$ is H, $(C_1\text{-}C_6)$alkyl or $(C_2\text{-}C_6)$alkynyl. In a further embodiment, $R^3$ is H or $(C_1\text{-}C_4)$alkyl. In another embodiment, $R^3$ is H or $CH_3$. In another embodiment, $R^3$ is $CH_3$. In one embodiment, $R^3$ is H.

In another embodiment, $R^4$ is H, $(C_1\text{-}C_6)$alkyl, $(C_2\text{-}C_{16})$alkynyl, —$(C_0\text{-}C_4)$-alkylene-$(C_6\text{-}C_{10})$aryl, —C(O)NR' or —C(O)O—R', wherein R' is H or $(C_1\text{-}C_4)$alkyl. In a further embodiment, $R^4$ is H, $(C_1\text{-}C_4)$alkyl, —$(C_0\text{-}C_4)$-alkylenephenyl, —C(O)NR' or —C(O)O—R', wherein R' is H or $(C_1\text{-}C_4)$alkyl. In a further embodiment, and $R^4$ is H or $CH_3$.

In other embodiments, the first and second precursor polymers are co-polymers which may further contain other monomers to adjust (tune) the properties of the final precursor polymers, and therefore, the hydrogel composition. In another embodiment, the first and second precursor polymers may also be modified after polymerization to introduce functional groups to the hydrogel composition In an embodiment, the first and/or second precursor polymers are further functionalized with a ligand binding sequence, such as antibodies, proteins, aptamers, and other biological recognition agents. In one embodiment, the ligand binding sequence is a cell recognition peptide sequence. In another embodiment, the cell recognition peptide sequence is arginyl-glycyl-aspartic acid (RGD) or a derivative thereof. In one embodiment, a ligand binding sequence is bonded to the hydrogel composition such that the binding sequence, can for example, bind a drug target or an analyte in biosensing applications.

In another embodiment, the first and/or second precursor polymers are bonded to cell adhesion ligands, such that the hydrogel compositions are useful in cell or tissue cultures etc., whereby the hydrogel compositions become adhesive to mammalian cells (in vitro or in vivo). In one embodiment, the cell adhesion ligand is RGD, wherein the N-terminus of the RGD peptide is reacted with the hydrogel composition, for example, residual aldehyde groups of a aldehyde-functionalized precursor polymer through reductive amination, or with residual carboxyl groups of a hydrazide-functionalized precursor polymer. In one embodiment, the —COOH terminus of the RGD peptide is reacted with the hydrogel composition, for example residual hydrazide groups. In another embodiment, such ligands can be reacted with the precursor polymers before cross-linking.

In another embodiment, the first and/or second precursor polymers are co-polymers as defined above and further comprise a monomer, oligomer or macromonomer that increases the hydrophobicity of the precursor polymers. In one embodiment, the monomer, oligomer or macromonomer can form hydrophobic nanodomains (i.e. hydrophobic associations between the hydrophobic moieties) during hydrogel formation, which can aid in the cross-linking of the precursor polymers. In one embodiment, the hydrophobic nanodomains result in increased protein and/or hydrophobic drug binding. In one embodiment, the monomer, oligomer or macromonomer is oligo(lactic acid) methacrylate, poly(glycolic acid), copolymers of lactic acid and glycolic acid, polycaprolactone and other polyesters, polyamides, $(C_4\text{-}C_{20})$-alkyl or $(C_6\text{-}C_{14})$-aryl.

In one embodiment, the use of different additional monomers in either of the precursor polymers can impart different ionic character on the hydrogel. In one embodiment, the first and/or second precursor polymers are co-polymers as defined above, and further include acrylic acid, methacrylic acid, itaconic acid, fumaric acid, maleic acid, vinylacetic acid or tert-butyl2-acryloylhydrazinecarboxylate (BAHC), which impart anionic character on the hydrogel composition, while 2-dimethylaminoethylmethacrylate (DMAEMA), 2-dimethylaminoethyacrylate (DMAEA), aminoethyl methacrylate (AEMA) or structural analogues thereof, or allylamine, impart cationic character on the hydrogel. For example, in one embodiment, a cationic hydrogel is formed wherein the first precursor polymer is comprised of OEGMA, acrylic acid and DMEAMA, and the second precursor polymer is comprised of OEGMA and DMEMA, in which the DMEAMA monomer provides cationic character to the overall hydrogel composition.

In an embodiment, the hydrogel composition of the present disclosure comprises,
a. the first precursor polymer which is a co-polymer of oligoethylene glycol methacrylate and acrylic acid;
b. the second precursor polymer which is a co-polymer of oligoethylene glycol methacrylate and N-(2,2-dimethoxyethyl)methacrylamide (DMEMAm), wherein the acrylic acid has carboxylic acid groups which are functionalized as hydrazide moieties, and DMEMAm has acetal groups which are hydrolyzed to aldehyde moieties.

In an embodiment, the hydrogel compositions of the present disclosure comprise about 10 mol %, about 50 mol % or about 90 mol % of oligoethylene glycol methacrylate monomer (OEGMA$_{475}$). In a further embodiment, the hydrogel compositions comprise between about 0-90 mol %, 20-90 mol % or about 30-90 mol % of oligoethylene glycol methacrylate monomer (OEGMA$_{475}$).

In another embodiment, the hydrogel compositions comprise a concentration of the hydrazide-functionalized poly(oligoethylene glycol methacrylate) polymer and a concentration of the aldehyde- and/or ketone-functionalized poly(oligoethylene glycol methacrylate) polymer in a range of about 50 mg/mL to about 600 mg/mL or about 100 mg/mL to about 300 mg/mL. In a further embodiment, the hydrogel compositions comprise a concentration of hydrazide-functionalized poly(oligoethylene glycol methacrylate) polymer and a concentration of aldehyde- and/or ketone-functionalized poly(oligoethylene glycol methacrylate) polymer in a range of about 100 mg/mL to about 200 mg/mL.

In an embodiment, the hydrogel compositions comprise a degree of functionalization comprising the hydrazide-functionalized poly(oligoethylene glycol methacrylate) polymer and the aldehyde- and/or ketone-functionalized poly(oligoethylene glycol methacrylate) polymer in the range of about 5 mol % to about 50 mol %, about 10 mol % to about 45 mol % or about 20 mol % to about 40 mol %. In another embodiment, the hydrogel compositions comprise a degree of functionalization comprising the hydrazide-functionalized poly(oligoethylene glycol methacrylate) polymer and the aldehyde- and/or ketone-functionalized poly(oligoethylene glycol methacrylate) polymer in the range of about 20 mol % to about 40 mol %.

In an embodiment, the hydrogel compositions of the present application are chemically and mechanically tunable, for example, based on the selection and identity of the monomers of the precursor polymers. In one embodiment, the first and/or second precursor polymers include M(EO)$_2$MA as a monomer which results in thermoresponsive hydrogels. In one embodiment, the first and/or second precursor polymers include acrylic acid, methacrylic acid, itaconic acid, fumaric acid, maleic acid, vinylacetic acid or tert-butyl2-acryloylhydrazinecarboxylate (BAHC), 2-dimethylaminoethylmethacrylate (DMAEMA), 2-dimethylaminoethyacrylate (DMAEA), aminoethyl methacrylate (AEMA), or allylamine which results in a pH-responsive hydrogel. In one embodiment, the hydrogels contain cell-specific ligands which results in a bioactive hydrogel. In an embodiment, two or more hydrazide-functionalized poly(oligoethylene glycol methacrylate) polymers and two or more aldehyde-functionalized poly(oligoethylene glycol methacrylate) polymers with different oligo(ethylene glycol) side chain lengths (n) are mixed together to create hydrogels with intermediate properties to the constituent precursor polymers.

In another embodiment, the properties of the hydrogel compositions are tuned by selecting precursor polymers having different lower critical solution temperatures (LCST) within the hydrogel compositions. For example, a mixture of two first precursor polymers having two different LCSTs and two second precursor polymers having two different LCSTs results in hydrogels with well-defined phase-separated nanoscale domains. In one embodiment, changing the ratio of the monomers within the precursor polymers results in hydrogels with different properties.

In one embodiment, any free radical polymerizable monomer such as vinylics, (meth)acrylics, acrylamides, allylics, or styrenics polymerizable with OEGMA can be used to functionalize POEGMA-based materials. In one embodiment, the co-monomer is a (meth)acrylic-type co-monomer.

In one embodiment of the disclosure, the first and/or second precursor polymers of the present disclosure have cationic, anionic or amphoteric character. For example, in one embodiment, a cationic hydrogel composition is comprised of cationic, hydrazide functionalized poly(oligoethylene glycol methacrylate) and aldehyde and/or ketone functionalized poly(oligoethylene glycol methacrylate). In another embodiment, an anionic hydrogel composition is comprised of anionic, hydrazide functionalized poly(oligoethylene glycol methacrylate) and aldehyde and/or ketone functionalized poly(oligoethylene glycol methacrylate). In a further embodiment, amphoteric hydrogel compositions are comprised of either anionic or cationic hydrazide functionalized poly(oligoethylene glycol methacrylate) and anionic or cationic aldehyde and/or ketone functionalized poly(oligoethylene glycol methacrylate). In other embodiments, the first or second precursor polymer is neutral, cationic or anionic depending on the selection of the monomers.

In another embodiment of the disclosure, depending on the identity of the first and/or second precursor polymers, the hydrogel compositions have different gelation times. In one embodiment, immediate gelation is useful for drug delivery applications which avoid the drug from diffusing out of pre-gelled compositions. In other embodiments, gelation times of 5-30 minutes are favorable, for example, in biological barrier applications enabling the polymers to spread to fill gaps before gelation happens.

In an embodiment, the mass-base swelling ratio relative to the dry state ($Q_m$), the rate of degradation and the elastic storage modulus (G') of the hydrogel compositions of the present application are controlled by the degree of functionalization and the concentration of the hydrazide-functionalized poly(oligoethylene glycol methacrylate) polymer and the aldehyde- and/or ketone-functionalized poly(oligoethylene glycol methacrylate) polymer.

In an embodiment, the mass-base swelling ratio relative to the dry state ($Q_m$) is about 2.0 to about 100.0, about 3.0 to about 50.0, or about 4.0 to about 20.0. In a further embodiment, the elastic storage modulus (G') is about 0.1 kPa to about 40 kPa, about 0.5 kPa to about 30 kPa, or about 1.0 kPa to about 25 kPa.

In one embodiment, depending on the identity of the precursor polymers, the stability of the hydrogel compositions can be adjusted. In one embodiment, the hydrogel compositions of the present application are stable in vivo for period of at least about 3-6 months. In another embodiment, the hydrogel compositions of the present application are stable in vivo for period of at least 1 day, two days, 3 days, 7 days, 2 weeks or 3 weeks.

In one embodiment, depending on the external environment, the hydrogel compositions of the present disclosure de-swell to a plateau water content of about 60% (w/w)

water, about 70% (w/w) of water, about 80% (w/w) of water. In another embodiment, the hydrogel compositions swell to about 90% (w/w) or about 95% (w/w) of water. In another embodiment, physiological temperature induces de-swelling of the hydrogels. In this embodiment, such hydrogel compositions are collapsed which refers to hydrogels which are substantially reduced in size and have a smaller average diameter than in the swollen state. In the collapsed state, the hydrogels adopt a configuration which does not favor the ingress of water into the particle. It will be appreciated that the swelling of a hydrogel is caused by a flow of water into the particle. It will be appreciated that the amount of water in the particle will depend on the temperature and/or pH as well the properties of the polymer comprising the hydrogel (e.g. charge density).

In one embodiment, the hydrazone cross-linking, for example, by hydrazone bond formation, is useful in biomedical applications, as hydrazone bonds are degradable via hydrolysis as well as enzymatic action, and thus can break apart to release the lower molecular weight precursor polymers for ultimate clearance through the kidneys. In an embodiment, due to the reversible or degradable nature of the cross-linking bonds, the hydrogel compositions are degradable in vivo and reform the first and second precursor polymers having the same, or similar, molecular weight compared to the non-crosslinked precursor polymers. In one embodiment, the hydrogels have a molecular weight which is less than the molecular weight cut-off for renal (kidney) clearance. In another embodiment, the hydrogels have a molecular weight which is less than about 60 kDa, or less than about 50 kDa. In another embodiment, the hydrogels have a molecular weight of between about 10 to about 60 kDa, or about between about 20 to about 60 kDa.

In an embodiment, the hydrazide-functionalized poly (oligoethylene glycol methacrylate) polymer and the aldehyde- and/or ketone-functionalized poly(oligoethylene glycol methacrylate) polymer represent both the hydrogel precursor polymers as well as the hydrogel degradation products.

In an embodiment, the hydrogel compositions of the present application are weakly binding to cells and proteins, and therefore minimize the inflammatory response when the hydrogels are used in biomedical applications (such as injection of a drug-loaded hydrogel). In another embodiment, the hydrogel compositions are non-cytotoxic. In an embodiment, the hydrogel compositions of the present application are injectable.

The present disclosure also includes a kit for preparing a hydrogel composition, the kit comprising:
 a. a first precursor polymer as defined in the present disclosure;
 b. a second precursor polymer as defined in the present disclosure; and
 c. instructions for use.

The present disclosure also includes a double-barreled syringe, comprising,
 a. a first barrel containing a first precursor polymer as defined in the present disclosure;
 b. a second barrel containing a second precursor polymer as defined in the present disclosure,
wherein upon injection, the first and second precursor polymers form, in situ, the hydrogel composition as defined in the present disclosure.

In one embodiment of the disclosure, the hydrogel compositions of the present disclosure are useful in biomedical applications including drug delivery vehicles, molecular probes, mechanical supports for soft tissue, biological lubricants, and other applications. In another embodiment, the degradability (for example, acidic degradability) of the hydrogel compositions is useful as intracellular drug delivery vehicles (i.e. degradation would happen faster inside the endosome than outside the cell).

In one embodiment, the double-barreled syringe further contains a drug for the treatment of a condition. In one embodiment, the in situ formed hydrogel composition is, for example, responsive to the environment upon which it is located and can deliver a drug based on environmental signals. For example, in one embodiment, the in situ formed hydrogel composition is thermoresponsive and deswells upon an increase in temperature. In one embodiment therefore, the hydrogel composition acts a drug delivery composition at a site of infection where the body's temperature is increased. Upon being exposed to higher temperatures, the hydrogel composition deswells and releases the drug.

In one embodiment, there is included a method for coating a substrate with a hydrogel composition of the disclosure, the method comprising,
 a. adsorbing or reacting a first or second precursor polymer as defined herein on the substrate;
 b. coating the substrate from step (a) with the alternate precursor polymer;
 c. optionally repeating steps (a) and (b),
wherein the hydrogel composition is formed on the substrate. In one embodiment, the at least one first or at least one second precursor polymer is adsorbed, reacted or coated on the substrate by dipping, printing, painting, spraying or delivering the polymers onto the substrate in any manner which results in the polymers forming the hydrogel compositions.

In one embodiment, the hydrogels of the present disclosure are layered upon a substrate using a layer-by-layer dipping technique, wherein a precursor polymer is applied to the substrate to coat the substrate, such that some of the polymer is adsorbed or reacted on the substrate. The first coat may either be the first precursor polymer or the second precursor polymer as described in the present disclosure. Upon coating with the first layer, the other (complementary) precursor polymer is subsequently coated on the substrate, wherein covalent cross-linking bonds (such as hydrazone bonds, when the precursor polymers are hydrazide and aldehyde-functionalized) form between the two layers thereby forming a hydrogel on the substrate. This process is repeated for as many times as desired, using alternating precursor polymers, forming a hydrogel coated substrate. In another embodiment, the covalent cross-linking bonds, such as hydrazone bonds, formed on the substrate may subsequently be reduced to form non-reversible hydrazine bonds. In one embodiment, the substrate is cellulose, polysulfone, cellulose acetate, or polyacrylonitrile, which are commonly used for dialysis membranes. In other embodiments, substrates include biomaterials (in which suppressing protein adsorption suppresses inflammation), such as polyethylene, polyesters, silicones, or polymethyl methacrylate. In other embodiments, wastewater treatment membranes may be treated with hydrogel compositions which are low fouling.

In another embodiment, the hydrogel compositions of the present disclosure are useful in biosensing applications for minimizing non-specific, off-target binding to the biosensor (see for example, Deng et al., JACS, 2014, 136, 12852-12855). In a further embodiment, the biosensing applications include, but are not limited to, coatings in both solid and porous surfaces. In an embodiment, the coated solid and porous surfaces are prepared by sequential layer-by-layer dipping technique analogous to polyelectrolyte layer-bylayer deposition using the hydrogel compositions of the present disclosure. In another embodiment, the solid and porous surfaces are coated for bioseparation applications. In a further embodiment, the solid and porous surfaces are coated to minimize non-specific protein adsorption. In one embodiment, the hydrogel compositions of the disclosure passivate the surface against non-specific binding, and thereby increase the specificity and signal-to-noise of a sensing event.

The hydrogels of the present disclosure are also useful for coating surfaces using a layer-by-layer dipping technique. For example, in one embodiment, cross-linking of nucleophilic and electrophilic-functionalized POEGMA polymers is used as a facile method to coat solid surfaces (both solid and porous) using the layer-by-layer dipping technique. For example, cross-linking of hydrazide and aldehyde-functionalized POEGMA polymers is used as a facile method to coat solid surfaces (both solid and porous) using the layer-by-layer dipping technique. In one embodiment, using the precursor polymer of the present disclosure avoids the need to surface-functionalize materials prior to coating (wherein at least a portion of the precursor polymer is adsorbed on the substrate in a first dipping step), and enables the facile creation of thin-layer gel structure as opposed to brush structures (better suited to the delivery of bioactive agents from a protein passivation layer).

In one embodiment of the present disclosure, the hydrogel compositions of the present disclosure are non-degradable hydrogel compositions. In an embodiment, the reversible hydrazone crosslink bonds are reduced by a suitable reducing agent to produce irreversible crosslink bonds. In another embodiment, the suitable reducing agents include, but are not limited to, sodium cyanoborohydride. In an embodiment, the non-degradable hydrogel compositions are stable in highly acidic environments for a period of about 60 hours, about 50 hours, about 40 hours or about 30 hours. In another embodiment, the non-degradable hydrogel compositions are useful in biosensing and bioseparation applications. In a further embodiment, the biosensing and bioseparation applications are coatings for biosensors or membranes.

The first and/or second precursor polymers of the present disclosure can be synthesized using any polymerization technique known in the art. In one embodiment, the precursor polymers are prepared using chain transfer free radical copolymerization. In another embodiment, the precursor polymers are prepared using controlled radical polymerization (atom transfer radical polymerization, reversible addition-fragmentation chain transfer polymerization), which allows for the preparation of such precursors having defined and narrow range of molecular weights, which in one embodiment, aids in the ability of the hydrogels to be cleared from the body in, for example, drug delivery applications.

EXAMPLES

The following non-limiting examples are illustrative of the present application:

Example 1: Synthesis of Pre-polymers and Preparation of Hydrogels

Materials

Oligo(ethylene glycol) methyl ether methacrylate with an average number-average molecular weight of 475 g/mol (OEGMA$_{475}$, Sigma Aldrich, 95%) was purified by passing it over a column of basic aluminum oxide (Sigma Aldrich, type CG-20) to remove the methyl ether hydroquinone (MEHQ) and butylated hydroxytoluene (BHT) inhibitors. Acrylic acid (AA, Sigma Aldrich, 99%), thioglycolic acid (TGA, Sigma Aldrich, 98%) and 2,2-azobisisobutryic acid dimethyl ester (AIBMe, Wako Chemicals, 98.5%), adipic acid dihydrazyde (ADH, Alfa Aesar, 98%), N'-ethyl-N-(3-dimethylaminopropyl)-carbodiimide (EDC, Carbosynth, Compton Calif., commercial grade), sodium cyanoborohydride (NaBH$_3$CN, Sigma Aldrich, reagent grade), aminoacetaldehyde dimethyl acetal (Sigma Aldrich, 99%), 2,2,6,6-tetramethyl-1-piperidinyloxy (TEMPO, Sigma Aldrich, 98%), methacryloyl chloride (Sigma Aldrich, purum), bovine serum albumin (BSA, Sigma Aldrich, >96%), fibrinogen from human plasma (Sigma Aldrich), Arg-Gly-Asp (RGD, Sigma Aldrich, ≥97%) and fluorescein isothiocyanate (FITC, Sigma Aldrich, 90%) were all used as received. For all experiments Milli-Q grade distilled deionized water (DIW) was used. Dimethyl sulfoxide (DMSO, reagent grade) was purchased from Caledon Laboratory Chemicals (Georgetown, ON). Hydrochloric acid (1M) was received from LabChem Inc. (Pittsburgh, Pa.). 3T3 mouse fibroblasts were obtained from ATCC: Cederlane Laboratories (Burlington, ON). Cell proliferation media, recovery media, and trypsin-EDTA were obtained from Invitrogen (Burlington, ON). Media contents included Dulbecco's Modified Eagle Medium-high glucose (DMEM), fetal bovine serum (FBS), penicillin streptomycin (PS), and trypsin-EDTA and were purchased from Invitrogen Canada (Burlington, ON). Thiazolyl blue tetrazolium bromide (MTT) was purchased from Sigma Aldrich (Oakville, ON). LIVE/DEAD assay for cell viability were purchased from Invitrogen Canada (Burlington).

Chemical Characterization

Aqueous size exclusion chromatography (SEC) was performed on a system consisting of a Waters 515 HPLC pump, Waters 717 plus autosampler, three Ultrahydrogel columns (30 cm×7.8 mm i.d.; exclusion limits: 0-3 kDa, 0-50 kDa, 2-300 kDa) and a Waters 2414 refractive index detector. A mobile phase consisting of 0.3 M sodium nitrate and 0.05 M phosphate buffer (pH 7) at a flow rate of 0.8 mL/min was used for all polymers analyzed, and the system was calibrated with narrow-dispersed poly(ethylene glycol) standards ranging from 106 to 584×10$^3$ g/mol (Waters). $^1$H-NMR was performed on a Bruker AVANCE 600 MHz spectrometer using deuterated chloroform as the solvent. The acrylic acid content of the polymers was determined using base-into-acid conductometric titration (ManTech Associates) using 50 mg of polymer dissolved in 50 mL of 1 mM NaCl as the analysis sample and 0.1 M NaOH as the titrant.

Synthesis of N-(2,2-dimethoxyethyl)methacrylamide (DMEMAm)

The N-(2,2-dimethoxyethyl)methacrylamide (DMEMAm) monomer was synthesized by adding aminoacetaldehyde dimethylacetal (50 mL, 461 mmol) and 100 mg of TEMPO to a concentrated sodium hydroxide solution (100 mL) at 10° C. Methacryloyl chloride (47.08 mL, 486 mmol) was then added drop-wise over a period of 2 hours under nitrogen, and the resulting mixture was allowed to react for 24 hours under nitrogen at room temperature. Subsequently, the mixture was extracted with 150 mL of petroleum ether to remove impurities. The aqueous phase was then saturated with sodium chloride and extracted three times with 75 mL tert-butyl methyl ether. The organic phase was dried with magnesium sulfate, filtered, and concentrated under reduced pressure, yielding an orange oil as the final product. This product was stored in the dark at 10° C. until use. (Purity: determined from $^1$H-NMR, >99%). $^1$H-NMR (DMSO, 600 MHz): δ=1.84 (s, 3H, —CH3), δ=3.00-3.35 (m, 8H, O—CH3 and —N(H)—CH2), δ=4.42 (t, 1H, —CH), δ=5.32 (s, 1H, =CH2), δ=5.66 (s, 1H, =CH2), δ=7.98 (s, 1H, —NH).

Synthesis of the Hydrazide-Functionalized Precursor (POH)

POH precursors were prepared by adding AIBMe (37 mg, 0.14 mmol), OEGMA$_{475}$ (4.0 g, 8.4 mmol), AA (0.25 g, 3.5 mmol, for PO$_{100}$H$_{30}$), and TGA (1 µL, 0.02 mmol) to a 50 mL Schlenk flask. Dioxane (20 mL) was added and the solution was purged with nitrogen for at least 30 minutes. Subsequently, the flask was sealed and submerged in a pre-heated oil bath at 75° C. for 4 hours under magnetic stirring. After the solvent was removed, the resulting poly(OEGMA-co-AA) polymer was purified by dialysis against DIW for a minimum of 6 (6+ hour) cycles and lyophilized to dryness. The carboxylic acid groups of POH precursor were subsequently converted to hydrazide groups via a carbodiimide-mediated conjugation of a large excess of adipic acid dihydrazide (ADH). The polymer (3.8 g) was dissolved in 100 mL DIW and added to a 250 mL round-bottom flask. ADH (2.65 g, 15.2 mmol, 5 mol eq.) was added and the pH of the solution adjusted to pH=4.75 using 0.1 M HCl. Subsequently, EDC (1.18 g, 7.6 mmol, 2.5 mol eq.) was added and the pH maintained at pH=4.75 by the dropwise addition of 0.1 M HCl over 4 hours. The solution was left to stir overnight, dialyzed against DIW for a minimum of 6 (6+ hour) cycles, and lyophilized. The degree of functionalization was determined from conductometric base-into-acid titration. The polymers were stored as 20 w/w % solutions in PBS at 4° C.

Synthesis of the Aldehyde-Functionalized Precursor (POA)

POA precursors were prepared by adding AIBMe (60 mg, 0.26 mmol), OEGMA$_{475}$ (4.0 g, 8.4 mmol), DMEMAm (0.60 g, 3.5 mmol, for PO$_{100}$A$_{30}$) and TGA (1 µL, 0.02 mmol) to a 50 mL Schlenk flask. Dioxane (20 mL) was added and the solution was purged with nitrogen for at least 30 minutes. Subsequently, the flask was sealed and submerged in a pre-heated oil bath at 75° C. for 4 hours under magnetic stirring. After polymerization, the solvent was removed and the poly(OEGMA-co-DMEMAm) polymer was purified by dialysis against DIW for a minimum of 6 (6+ hour) cycles and lyophilized to dryness. The acetal groups of PO$_{10}$A were subsequently converted to aldehydes by dissolving 3.5 g of the copolymer prepared above in 75 mL DIW and 25 mL 1.0 M HCl in a 250 mL round-bottom flask. The solution was left to stir for 24 hours, dialyzed for a minimum of 6 (6+ hour) cycles and lyophilized to dryness. The polymer was stored as 20 w/w % solution in PBS at 4° C.

Synthesis of RGD Labelled POA

RGD labelled POA precursor (PO$_{100}$A$_{30}$-RGD) was prepared by incubating a solution of PO$_{100}$A$_{30}$ (0.6 g) and RGD (10 mg, 28.9 µmol) in 50 mL distilled deionized water for 24 hours under continuous agitation. Subsequently, sodium cyanoborohydride (18.2 mg, 0.29 mmol, 10 mol eq. to RGD) was added and the solution stirred for another 48 hours. The solution was dialyzed for a minimum of 6 (6+ hour) cycles and lyophilized to dryness. The polymer was stored as 20 w/w % solution in PBS at 4° C.

Synthesis of Fluorescein-Isothiocyanate Labelled Proteins

Fluorescein-isothiocyanate (FITC)-labelled bovine serum albumin (BSA-FITC) and fibrinogen (Fib-FITC) were prepared by dissolving 50 mg of the protein in a 100 mL carbonate buffer at pH=9.0. FITC (1 mg) was added and the solution was incubated at room temperature for at least 12 h under gentile mechanical agitation. The FITC-labelled protein was subsequently dialyzed against distilled deionized water 6 (6+ hour) cycles and lyophilized to dryness. The isolated conjugated protein was stored at −4° C. in the dark. For both proteins, a calibration curve was prepared to relate their concentration in PBS to the fluorescence signal measured at λ=495 nm and 535 nm, with linear calibration curves ($R^2$>0.99) observed in the concentration range of 2 to 10 µg/mL and 10 to 100 µg/mL respectively for BSA and fibrinogen.

Synthesis of a Ketal-Protected Ketone Monomer (N-((2-methyl-1,3-dioxolan-2-yl)methyl)methacrylamide)

Synthesis of the protected ketone monomer was conducted based on a modification of a previously reported protocol (50). Chloroacetone (10 mL, 12.5 mmol) and the potassium salt of phthalimide (25.5 g, 13.8 mmol) were added to 150 mL of stirred dry acetone. The solution was then heated to 80° C. for 20 hours, after which it was cooled to room temperature and the acetone was removed in a rotary evaporator. The resulting solid was then redissolved in methylene chloride and washed repeatedly with water. The methylene chloride layer was dried over magnesium sulfate, filtered, and removed using a rotary evaporator. The resulting yellow crude solid was washed with diethyl ether several times until the solid became white; this solid was subsequently dried in a vacuum oven to yield purified intermediate A (Scheme 1A). Intermediate A (10 g, 50 mmol) was then added to 180 mL of toluene along with ethylene glycol (5.85 mL, 100 mmol) and dry para-tolenesulfonic acid (934 mg, 5 mmol) and refluxed for 15 hours. The reaction mixture was cooled to room temperature and the ethylene glycol layer was extracted three times with diethyl ether. The toluene and ether fractions were combined and washed three times with 5% (w/v) NaOH followed by deionized water. The organic layer was dried over magnesium sulfate and solvent was removed in a rotary evaporator. The crude was recrystallized from ethanol to yield pure intermediate B (Scheme 1B). Intermediate B was subsequently added to 100 mL of deionized water along with 15 g of NaOH and refluxed for 2 days, with an additional 60 g of NaOH added slowly over the course of the reflux. Afterwards, the reaction mixture was cooled to room temperature and extracted three times with 50 mL dichloromethane. The organic layers were then combined and dried over magnesium sulfate, filtered, and concentrated in a rotary evaporator to yield pure product C (Scheme 1C), a slightly yellow oil. Finally, the monomer was prepared by adding product C (21.1 mL, 180 mmol) to a 20% (w/v) NaOH solution (in water) containing 4-hydroxy TEMPO (10 mg, 0.06 mmol). This reaction mixture was brought to 0° C. in an ice bath and methacryloyl chloride (16.5 mL, 174 mmol)

was added drop-wise over 2 hours under nitrogen flow. The ice bath was then allowed to warm to room temperature and the reaction left to stir overnight in darkness. After this time, stirring was halted and the product was allowed to collect at the top of the reaction flask. The pure monomer product (along with inhibitor) (shown in Scheme 1D) was then isolated using a separatory funnel. The monomer was stored in the darkness at −20° C. until use.

$^1$H NMR (600 MHz) in DMSO-$d_6$: RNHCH$_2$C(OCH$_2$CH$_2$O)CH$_3$, 1.3 ppm, singlet, 3H; CH$_2$CCH$_3$CONHR', 2 ppm, singlet, 3H; RNHCH$_2$C(OCH$_2$CH$_2$O)CH$_3$, 3.5 ppm, doublet, 2H; RNHCH$_2$C(OCH$_2$CH$_2$O)CH$_3$, 4 ppm, singlet, 4H; CH$_2$CCH$_3$CONHR', 5.35-5.65 ppm, doublet, 2H; CH$_2$CCH$_3$CONHR', 6 ppm, singlet, 1H.

Scheme 1. Synthesis of a ketal-protected ketone monomer

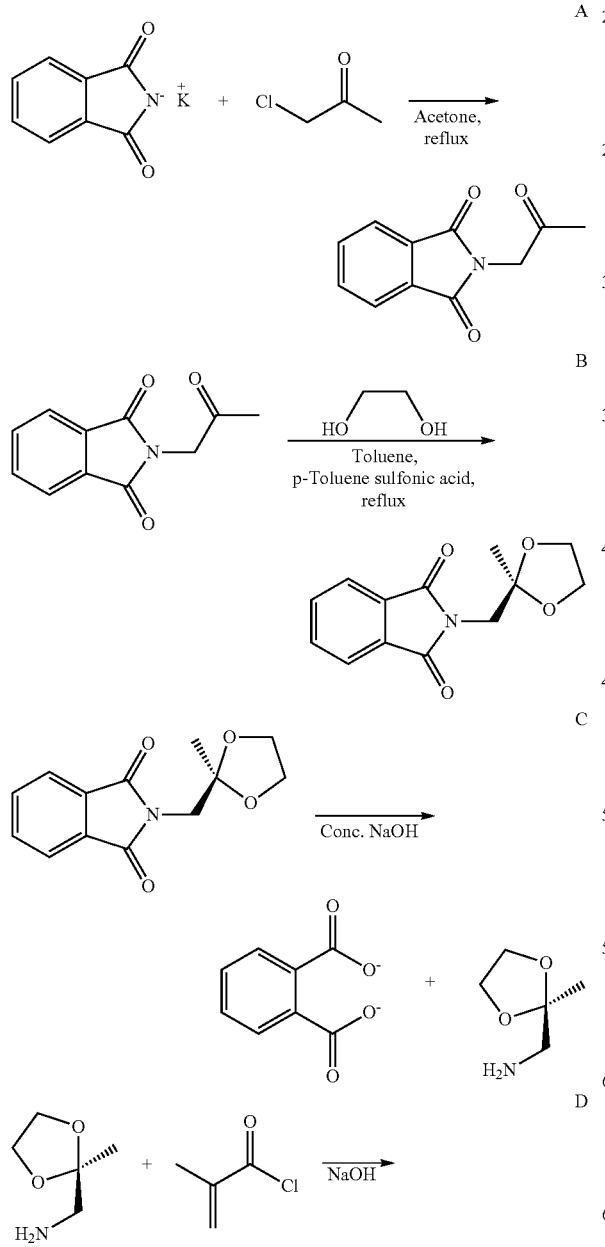

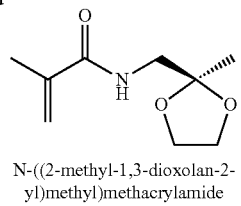

N-((2-methyl-1,3-dioxolan-2-yl)methyl)methacrylamide

Synthesis of Acrylate Hydrazide Monomer

To a solution of boc-carbazate (2.07 g, 15.7 μmoles) in CH$_2$Cl$_2$ (75 mL) was added Et$_3$N (2.40 mL, 17.3 μmoles, 1.1 eq) under a nitrogen atmosphere and the solution was cooled to 0° C. Acryloyl chloride (1.27 mL, 15.7 μmoles) was added dropwise over 5 min and the reaction was allowed to stir at 0° C. for 30 min. The crude reaction mixture was filtered to remove the triethylamine hydrochloride salt and the filtrate was concentrated by rotary evaporation. The product was purified via silica gel column chromatography (2:1→1:1 Hex/EtOAc) to give 1.52 g of the desired product (52% yield). $^1$H NMR (600 MHz; DMSO): δ9.79 (s, 1H), 8.84 (s, 1H), 6.21-6.16 (m, 2H), 5.71 (dd, J=9.2, 3.1, 1H), 1.41 (s, 9H). $^{13}$C NMR (150 MHz; DMSO): 164.19, 155.20, 129.34, 126.75, 79.17, 28.03.

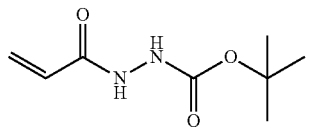

Following polymerization, the hydrazone bond is cleaved off by acid treatment to expose the reactive hydrazide group.

Preparation of Injectable Hydrogels:

POEGMA hydrogels were prepared via co-extrusion of hydrazide-functionalized (POH) and aldehyde-functionalized (POA) precursors dissolved in 10 mM PBS. Intensive mechanical mixing of both polymer precursor solutions was achieved through the use of a double barrel syringe fitted with a static mixer at the outlet (Medmix Systems). Hydrogel disks for all in vitro testing were prepared by extrusion of the reactive polymer precursors through the double barrel syringe into cylindrical silicone rubber molds (diameter=7 mm, volume=300 μL) and incubated at room temperature for at least 12 hours to ensure complete gelation prior to testing.

Swelling Kinetics:

Swelling of POEGMA hydrogels was determined at 22° C. in 10 mM PBS at pH 7.4. Hydrogels (n=4) were placed into cell culture inserts that are then placed in a 12-well cell culture plate and completely submerged with PBS (4 mL/well). At predetermined time intervals, the cell culture inserts were removed from the well, the PBS drained, and the hydrogel gently dried to wick off non absorbed PBS prior to weighing of the hydrogel. Subsequently, the hydrogels were resubmerged in a fresh 4 mL of PBS solution and tested repeatedly until equilibrium swelling was reached (generally ~30 hours). Error bars represent the standard deviation of the replicate measurements. The mass-based swell ratio ($Q_m$) was calculated by dividing the mass of the hydrogel at any given time point ($m_h$) by the dry mass of polymer in the hydrogel ($m_p$=initial hydrogel mass×(1−water content)).

The markers ((Δ) 25 mol %, (●) 30 mol % and (▽) 40 mol %) indicate the initial swell ratio at preparation (lower number) and the equilibrium swell ratio after soaking in 10 mM PBS for 30 hours (higher number) at condition.

Degradation Kinetics:

Degradation of POEGMA hydrogels ((○) 100 mg/mL, (◐) 125 mg/mL, (◑) 150 mg/mL, (◕) 175 mg/mL, (●) 200 mg/mL and (Δ) 150 mg/mL and 40 mol %) was determined at 37° C. in 100 mM HCl at pH 1.0; these acid-catalyzed conditions were used to compare the degradation properties of the hydrogels on a more measurable time frame. Hydrogels (n=4) were placed into cell culture inserts that are subsequently placed in a 12-well cell culture plate and completely submerged with the HCl solution (4 mL per well). At predetermined time intervals, the cell culture inserts were removed from the well, the PBS drained and the hydrogel gently dried to wick off non absorbed solution prior to weighing of the hydrogel. Subsequently, the hydrogels were resubmerged in fresh HCl solution (4 mL/well) until the hydrogel was completely degraded (i.e. no separate phase was observed between the hydrogel and the HCl bath solution). Error bars represent the standard deviation of the replicate measurements.

Hydrogel Rheology:

The rheological properties of the hydrogels were measured using an ARES rheometer (TA Instruments) operating under parallel-plate geometry with a plate diameter of 7 mm and a plate spacing of 1 mm. Rheological properties were measured by first conducting a strain sweep from 0.1-100% strain at 1 Hz to identify the linear viscoelastic range of the hydrogels. A strain was then selected from within this linear range and set as a constant to perform a frequency sweep from 1 to 100 rad/s to measure shear elastic (G') and loss (G") moduli. All measurements were conducted at 25° C. and in triplicate, with error bars representing the standard deviation of the replicate measurements.

Cytotoxicity Assay:

The cytocompatibility of POH and POA precursors (n=4) was quantified using a MTT assay. NIH 3T3 fibroblasts were maintained in tissue culture flasks in DMEM supplemented with 10% FBS and 1% penicillin. Cytotoxicity of the linear polymers (at concentrations ranging from 200 to 2000 µg/mL) was evaluated using an MTT assay over a 1-day exposure time. NIH 3T3 fibroblasts were plated at density of $1.0 \times 10^4$ cells per well in a 24-well plate and maintained in DMEM media supplemented with 10% FBS and 1% penicillin. Cell viability was then characterized by removing the polymer solution, adding the MTT solution, and incubating over four hours. The absorbance of the MTT solution was read using a Biorad microplate reader (model 550) at 570 nm, normalized against a 630 nm baseline, and compared to that measured in cell-only wells in which no materials were added to estimate relative cell viability. Each experiment (hydrogels as well as controls) were done in quadruplicate, with reported errors representing the standard deviation of the replicates.

In Vitro Protein Adsorption Assay:

Protein absorption to the POEGMA hydrogels was assayed in 96 well plates. POH and POA polymer solutions (150 mg/mL) were sterilized and 60 µL of each precursor solution was extruded into each well and left overnight to ensure complete gelation. Once gelation was complete, 60 µL of 10 mM PBS was added to each well and hydrogels were allowed to swell to equilibrium prior to protein addition (over 30 hours). Unabsorbed PBS was then removed and 60 µL of either BSA-FITC or Fib-FITC solution (125, 250 or 500 µg/mL) was added. The hydrogels were incubated for 2 hours at 37° C. After 2 hours, the hydrogels were rinsed to remove unabsorbed protein and the fluorescence signal was measured using a VICTOR 3 multi-label microplate reader and compared to the stock solution controls. Each experiment (hydrogels as well as controls) were done in quadruplicate, with reported errors representing the standard deviation of the replicates.

Figure 3:
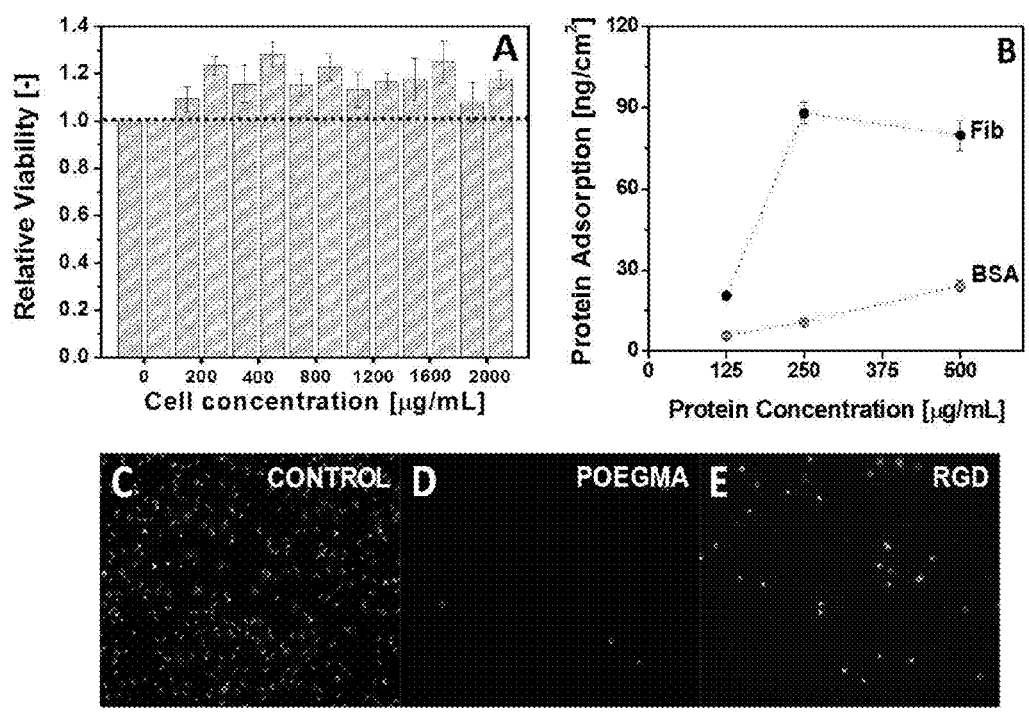
FIG. 3 shows biological properties of injectable precursors, hydrogels and degradation products of the disclosure. A) Relative cell viability of precursors as determined from an MTT assay on 3T3 mouse fibroblasts, B) BSA and Fib adsorption onto hydrogels of the disclosure, C-E) fluorescent microscopy images comparing the relative adhesion of 3T3 mouse fibroblasts to a polystyrene control.
Figure 4:
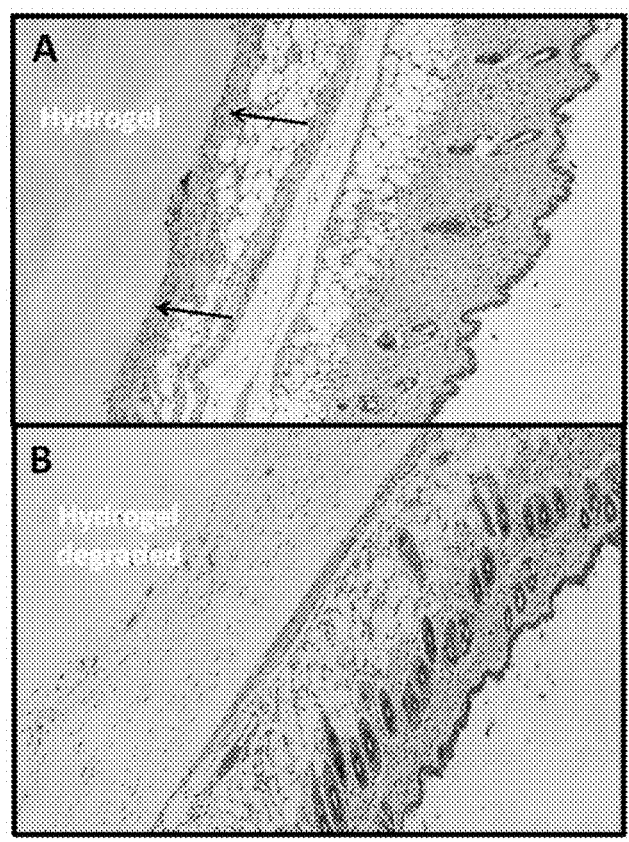
FIG. 4 shows histological section of H&E stained subcutaneous tissue samples following co-injection of precursors following A) acute and B) chronic time points. Arrows indicate the presence of leukocytes.

In Vitro Cell Adhesion Assay:

Cell adhesion to the POEGMA hydrogels and RGD-functionalized POEGMA hydrogels was assayed in 48-well plates using 3T3 fibroblasts as a model cell. Hydrogels were directly extruded into each well, with 100 µL of each sterilized polymer precursor solution (150 mg/mL in 10 mM PBS) added and then left overnight to ensure complete gelation. Gels were then washed with DMEM culture media prior to cell addition. Cells were plated on top of the hydrogels at a density of $2.0 \times 10^4$ cells per well together with 400 µL of DMEM and incubated for 24 hours at 37° C. After incubation, a LIVE/DEAD assay was conducted to visualize cells using microscopy and quantify adhesion. After staining, each well was washed three times with sterile 10 mM PBS to remove any non-adherent cells from the gels. Once washed, the resulting fluorescence of the cells on the gels was quantified using a VICTOR 3 multi-label microplate reader and compared to the cell-only TCPS control. All experiments were conducted in quadruplicate and multiple images were taken per well for analysis, with error ranges reported representing the standard deviation associated with the cell counts in the replicate measurements. Cell morphology on the hydrogels was visualized using a Zeiss Axiovert 200M fluorescence/live cell imaging microscope. The cell adhesions assays as shown in FIGS. 3C-E illustrate the fluorescent microscopy images comparing the relative adhesion of 3T3 mouse fibroblasts to a polystyrene control (C), POEGMA hydrogel (D) and POEGMA RGD hydrogel (E).

In Vivo Tolerability Assay:

The in vivo toxicity of the POEGMA hydrogels was assessed using a mouse subcutaneous injection model. A total of four BALB/c mice (22-24 g, Charles River Laboratories) were injected with 0.35 mL samples of a 150 mg/mL POH-POA hydrogels using a double-barrel syringe. Four additional mice were injected with 0.15M NaCl to serve as controls for comparing the tissue response to the hydrogels. Animals were also visually observed to identify any systemic toxic response. Both treated and control animals were sacrificed after 7 days (acute response) and 2 months (chronic response) after injection. A tissue sample that includes skin, underlying tissue, and residual material was recovered from the animals and subjected to histological analysis using hematoxylin and eosin staining. Animals were cared for in compliance with protocols approved by the Animal Research Ethics Board at McMaster University and regulations of the Animals for Research Act of the Province of Ontario and the guidelines of the Canadian Council on Animal Care.

Results and Discussion

Figure 1:
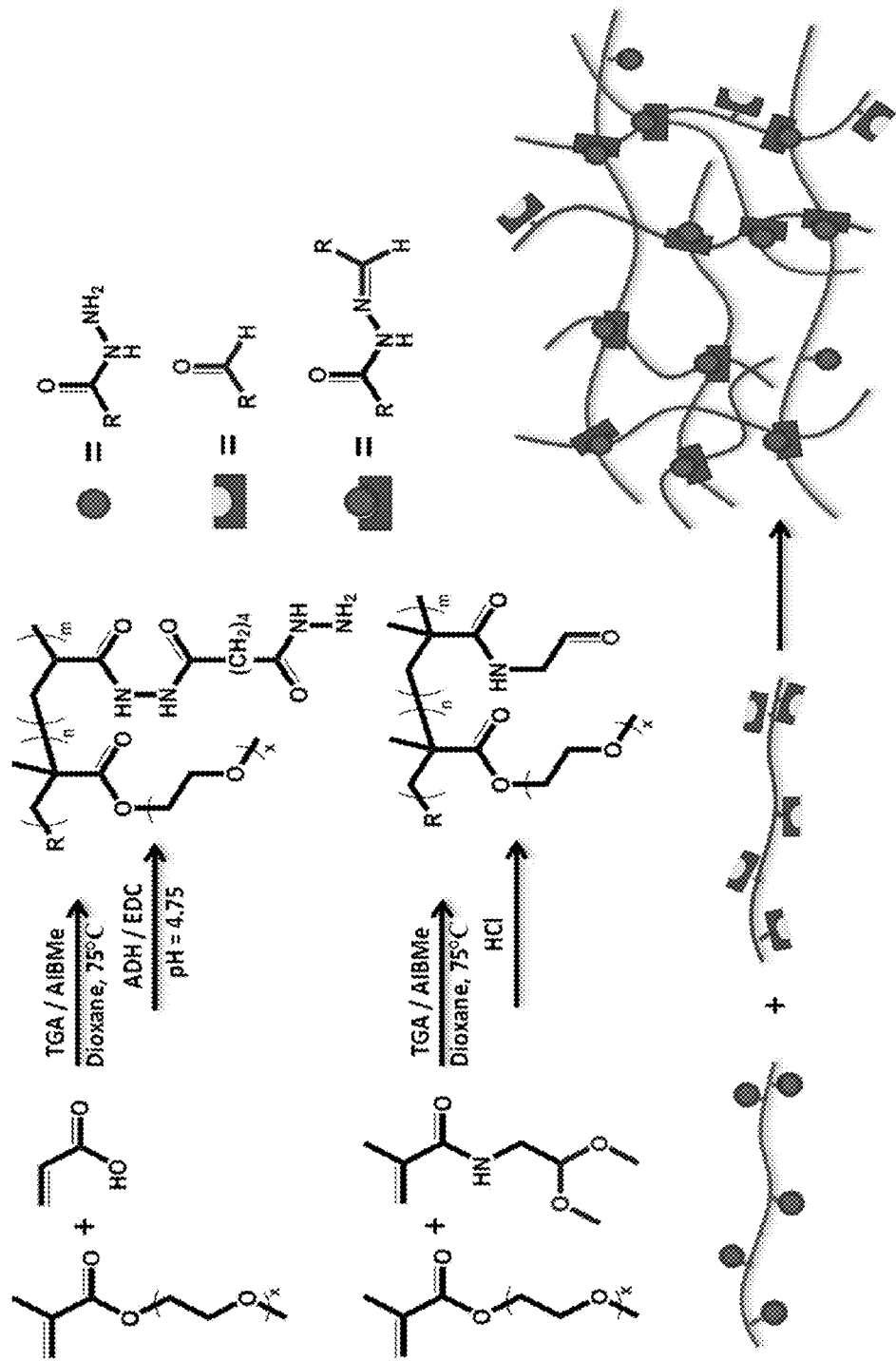

Hydrazide-functionalized POEGMA precursors (POH) are synthesized from conventional free-radical copolymerization of $M(EO)_2MA$, $OEGMA_{475}$ (EO repeat units, n=8-9) and acrylic acid (AA) in the presence of thioglycolic acid (TGA), followed by post-polymerization modification using carbodiimide-catalyzed coupling of adipic acid dihydrazide (ADH) in excess (29). The aldehyde functionalized POEGMA precursors (POA) are synthesized from the copolymerization of $M(EO)_2MA$, $OEGMA_{475}$ and N-2,2-diethoxyethyl methacrylamide (DMEMAm) in the presence of TGA, followed by the acid-catalyzed deprotection of the acetal to the aldehyde (FIG. 1) (29). The number-average molecular weight of the precursor polymers was controlled to be lower than $20 \times 10^3$ g/mol via the use of a chain transfer agent (Table 1), well below the renal clearance limit of $40\text{-}50 \times 10^3$ g/mol to facilitate polymer elimination following gel degradation (30). The aldehyde and hydrazide reactive precursors are labelled according to schemes $PO_xA_y$ and $PO_xH_y$ respectively, where x denotes the mole percentage of $OEGMA_{475}$ among the OEGMA monomers used and y denotes the overall mole percentage of DMEMAm or AA in the synthesis recipe. The synthetic versatility of the POEGMA platform to synthesize precursor polymers that differ was investigated in (i) reactive group content ($20 \leq y \leq 40$, and thus theoretical cross-link density) (29), (ii) in OEGMA composition ($0 \leq x \leq 100$, and thus phase transition temperature) (31), or (iii) the presence of specific functional moieties (e.g. hydrophobic oligo(lactic acid) (OLA) (32), or (iv) RGD cell-signaling peptide) (29) (FIG. 1). Since the POH and POA polymers represent both the hydrogel precursors as well as degradation products (29), the design of these polymers with a $M_n$ below the renal clearance-limit of ~32 kDa and a cloud point well above physiological temperature (>50° C.) should facilitate elimination of the precursors via the kidneys following hydrogel degradation while limiting polymer precipitation and associated inflammation of the surrounding tissue.

Figure 2:
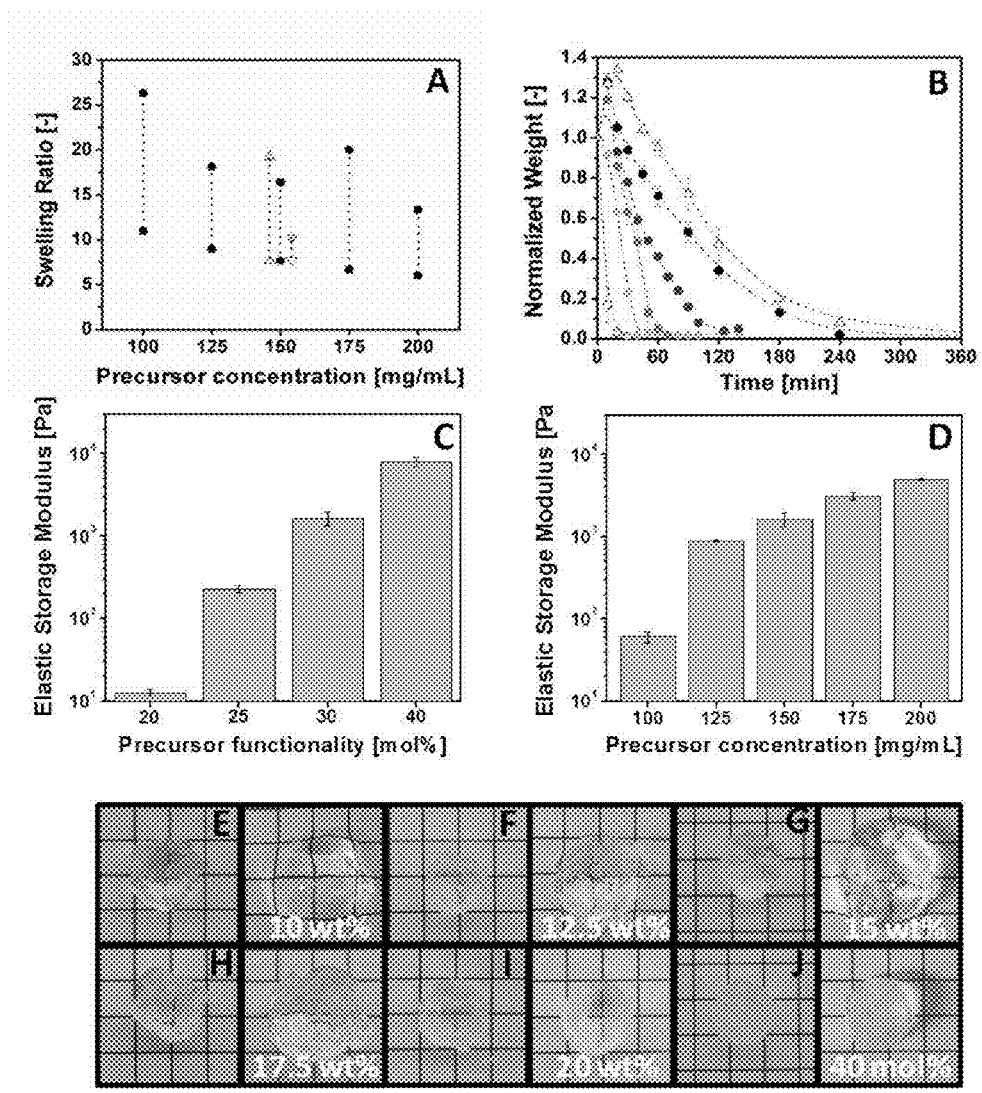

(i) POEGMA hydrogels were prepared by extruding 100, 125, 150 and 175 mg/mL $PO_{100}H_{30}$ and $PO_{100}A_{30}$ solutions in 10 mM PBS using a double-barrel syringe. Depending on the precursor concentration, gelation occurs over time frames ranging from a several hours (~8 hours) to a few minutes (<10 min), with precursor solutions of higher concentration and/or higher degrees of functionalization gelling faster representing the preferred embodiment for in vivo application. The hydrogels swell in PBS following preparation in PBS and after reaching equilibrium swelling after 30 hours (FIG. 2, E-J), indicating high hydrophilicity. The degree of functionalization of the $PO_{100}H_y$ and $PO_{100}A_y$ precursors (ranging from y=20 to 40 mol %, (Δ) 25 mol %, (●) 30 mol % and (∇) 40 mol %) and the concentration (ranging from 100 to 200 mg/mL, (○) 100 mg/mL, ( ) 125 mg/mL, ( ) 150 mg/mL, ( ) 175 mg/mL, (●) 200 mg/mL and (Δ) 150 mg/mL and 40 mol %) determines the cross-link density, which in turn controls the equilibrium mass-base swelling ratio ($Q_m$, FIG. 2A), the rate of degradation (FIG. 2B) and the elastic storage modulus (G', FIG. 2C) of the resulting hydrogel.

For POEGMA hydrogels prepared with precursors containing 25, 30 and 40 mol % functional groups, the equilibrium $Q_m$ is reached within 30 h (data not shown) and decreases systematically with the degree of chain functionalization from 19.2±0.25 (25 mol %) to 16.4±0.1 (30 mol %) to 10.2±0.03 (40 mol %). A similar trend is observed for hydrogels prepared with increasing precursor concentrations; as the $PO_{100}H_{30}$ and $PO_{100}A_{30}$ concentration is increased from 100 to 200 mg/mL the $Q_m$ generally decreases from 26.3±0.16 to 13.3±0.03.

The POEGMA hydrogels are cross-linked through the formation of dynamic hydrazone bonds, which are reversible in aqueous media. Aqueous size exclusion chromatography of the degradation products of a hydrogel prepared from $PO_xH_y$ and $PO_xA_y$ showed that the molecular weight distribution (MWD) of the degradation products is virtually identical to the combined MWDs of both precursors, with degradation proceeding from a bulk hydrogel to microgels, hyperbranched polymers, and ultimately the linear precursors (data not shown). Consequently, the $PO_xH_y$ and $PO_xA_y$ polymers represent both the hydrogel precursors as well as the hydrogel degradation products. Degradation of the POEGMA hydrogels is governed by the cross-link density and thus by the degree of functionalization or concentration of the $PO_xH_y$ and $PO_xA_y$ precursors (FIG. 2B). $PO_{100}$ hydrogels prepared at low concentration (<125 mg/mL) or a low degree of functionality (<30 mol %) degrade within 1 minute in 100 mM HCl. Hydrogels prepared at high concentration (200 mg/mL) or high functionality (40 mol %) degrade significantly slower, requiring approximately 5 hours to fully degrade under acid-catalyzed conditions (FIG. 2B). Long-term drug release experiments showed that the hydrazone cross-linked POEGMA hydrogels (150 mg/mL and 30 mol % reactive hydrazide and aldehyde groups) are stable for at least 5 months under physiological conditions in vitro but degrade within 4 weeks in vivo following subcutaneous injection in Balb/c mice. Thus, degradation times can be adjusted based on the degree of functionality or concentration of the polymer precursors used to prepare the hydrogels.

The $PO_{100}H_y$ and $PO_{100}A_y$ precursor system also yields hydrogels with an elastic modulus that can be tuned depending on the number of reactive functional groups as well as the precursor concentration. G' values ranging from 0.23±0.02 kPa (150 mg/mL, 25 mol %) to 8.0±1.0 kPa (150 mg/mL, 40 mol %) could be achieved by varying the precursor concentration and the degree of precursor functionalization (FIG. 2C). For comparison, the G' of conventional, pre-formed PEG hydrogels prepared from multi-arm and di-functional PEG precursors at comparable concentrations typically ranges from 0.25 to 6.0 kPa, analogous to the range that can be achieved with the injectable, in situ gelling hydrogels of the present disclosure. This facile tunability of G' enables effective matching of the hydrogel mechanical properties to that of the target tissue, which is important, for example, for tissue engineering applications. For example, from soft brain tissue (0.2-1 kPa) to relatively stiff cartilage or pre-calcified bone tissue (20-60 kPa) (34). Furthermore, the modulus of injectable POEGMA gel systems can be tuned independent of polymer concentration (and thus hydrogel osmotic pressure) if desired by modifying the number of cross-linkable functional groups on the polymer backbone.

Figure 5:
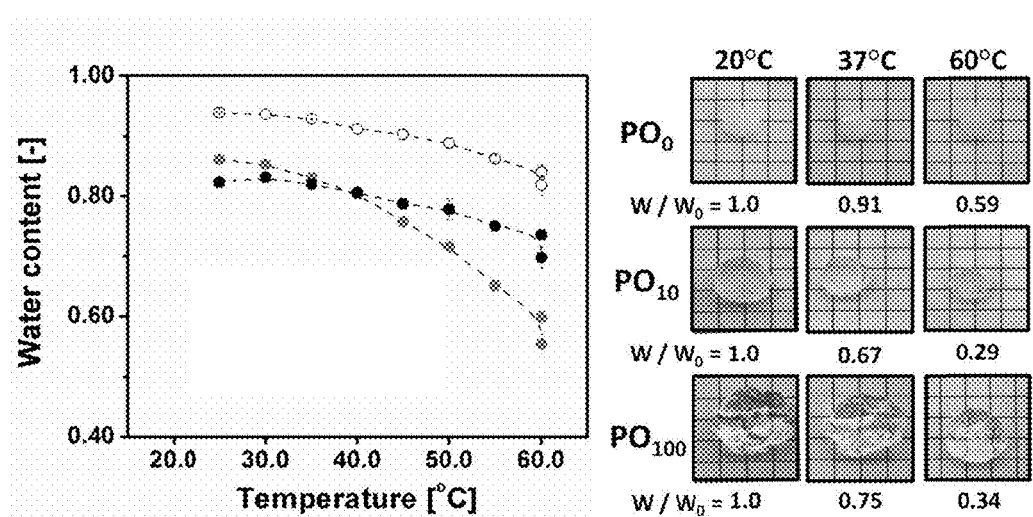
FIG. 5 is a graph which shows thermoresponsive properties of hydrogels of the disclosure.

(ii) POEGMA precursor polymers with varying amounts of $OEGMA_{475}$ monomer in the polymer (labeled as $PO_x$, where x indicates the mol fraction $OEGMA_{475}$ among the OEGMA monomers, with the remainder being $MEO_2MA$) were prepared by coextruding POH and POA precursor solutions of equal concentration (most typically 150 mg/mL=13 w/w %) and comparable degrees of functionality (y=30 mol %) (Table 1). By varying the incorporation of $OEGMA_{475}$, POEGMA injectable hydrogels can be prepared that are completely collapsed at 23° C. ($PO_0$), ($PO_{10}$) display a VPTT comparable to PNIPAm at ~33° C., ($PO_{100}$) do not display a VPTT up to 60° C. comparable to PEG. These hydrogels show differences in swelling kinetics at physiological temperature due to these different temperature dependencies; $PO_0$ (●) and $PO_{10}$ ( ) hydrogels prepared at 13 w/w % in PBS (water content=87.0%) de-swell at 37° C. to plateau water contents of 80 w/w % and 78 w/w %, respectively while $PO_{100}$ hydrogels prepared at the same precursor concentration swell to a plateau water content of 91 w/w % at 37° C. (FIG. 5). The shear storage modulus (G') of the $PO_0$, $PO_{10}$ and $PO_{100}$ hydrogels were measured directly after preparation and after swelling for 24 hours. The degradation profiles for (●)$PO_0$, ( ) $PO_{10}$ and (○) $PO_{100}$ in 1 M HCl are illustrated in FIGS. 6B-D. The gelation time and cross-link density decrease with increasing mole fraction of OEGMA$_{475}$ (n=8-9); for example, whereas PO$_0$H$_{30}$ and PO$_0$A$_{30}$ gel within 5 s and form a stiff hydrogel (G'~10 kPa), PO$_{100}$H$_{30}$ and PO$_{100}$A$_{30}$ require 20 min to gel and form a relatively weaker hydrogel (G'~0.8 kPa) (FIG. 6). Without wishing to be bound by theory, it is hypothesized that this trend is attributable to the steric hindrance of the longer PEG side chains in OEGMA$_{475}$ (n=8-9) that reduces the availability of the reactive aldehyde and hydrazide groups for cross-linking.

The biointerfacial properties of the injectable POEGMA hydrogels were evaluated using protein adsorption (FIG. 3B, and FIGS. 7A and B) and cell adhesion (FIG. 3C-E) assays. POEGMA hydrogels (150 mg/mL and 30 mol % reactive hydrazide and aldehyde groups) were incubated with two abundant human plasma proteins, bovine serum albumin (BSA) and fibrinogen (Fib), which are known to adsorb onto biomaterial surfaces within seconds to minutes. Both BSA and Fib adsorption to the POEGMA hydrogel is maintained below 90 ng/cm$^2$ even when exposed to a 500 µg/mL protein solution. BSA adsorption values in literature for PEGylated surfaces range in the order of 10 to 100 ng/cm$^2$ depending on concentration of the loading solution (35-40), comparable to the adsorption values reported in FIG. 3B. Thus, the injectable POEGMA hydrogels exhibit analogous protein repellent properties to conventional PEG-based hydrogels. Protein absorption is also likely to occur for POEGMA hydrogels (particularly for the smaller BSA molecule), which would suggest that the true protein adsorption on the hydrogel surface is likely even lower than reported in FIG. 3B. However, while a clear trend in protein adsorption is observed as a function of OEGMA monomer ratio (FIGS. 7A and B), all of these protein adsorption values reported (even for PO$_0$) are low relative to most biomaterials, indicating these POEGMA-based hydrogels are useful for biomedical applications. Indeed, the facile delamination of cells observed when the PO$_0$ hydrogel was subsequently cooled to 20° C. as well as the delamination observed from the tissue culture polystyrene surface (FIGS. 8C and D) following trypsin treatment (FIGS. 8 A and C) and following thermal treatment at 4° C. for 15 minutes (FIGS. 8B and D), suggests relatively weak binding of cells (and likely also proteins) to even this more "hydrophobic" hydrogel while also making this hydrogel of interest for the culturing and subsequent recovery of cells under very mild recovery conditions (FIG. 8). The PO$_x$H$_y$ and PO$_x$A$_y$ polymers (representing both the starting materials and the degradation products) did not impart any significant in vitro toxicity to 3T3 mouse fibroblasts up to a concentration of 2000 µg/mL (FIG. 3A and FIG. 9), a value which should be noted, represents an extremely high concentration relative to other reported in vitro assays. This result demonstrates that precursors as well as the degradation products of the hydrogels are non-cytotoxic.

(iii) Controlled adhesion of 3T3 mouse fibroblasts was achieved by functionalizing PO$_{100}$ hydrogels with a cell recognition peptide sequence arginyl-glycyl-aspartic acid (RGD) (41-44). RGD was coupled to the aldehyde functionalized PO$_{100}$A$_{30}$ precursor by a reductive amination to give an average degree of RGD functionalization of 1 RGD sequence per polymer chain (45). The average degree of functionalization can, however, easily be increased by functionalizing a larger fraction aldehyde groups on the precursor. Once extruded at 150 mg/mL with the PO$_{100}$H$_{30}$ precursor polymer, swollen POEGMA hydrogels contain 1.2 mM RGD, comparable to RGD functionalized hydrogels reported previously (46-48). At this concentration, RGD promotes a ~600% increase in 3T3 mouse fibroblast adhesion, as 36±1 cells/mm$^2$ (n=6) adhere compared to 6±1 cells/mm$^2$ (n=6) for the unmodified POEGMA hydrogel after 24 hours of incubation (44). Thus, the injectable POEGMA hydrogels can either suppress, or support, cell adhesion, consistent with other PEG-based hydrogels reported that are typically non-injectable and significantly more limited in terms of compositional diversity.

The in vivo response to the POEGMA hydrogels was evaluated by subcutaneous injection of 150 mg/mL polymer precursor solutions using a double-barrel syringe in BALB/c mice. Co-injection of the precursor solutions resulted in the formation of stable gels within the subcutaneous space of the mice for each hydrogel tested PO$_{100}$ (FIGS. 10A and B), PO$_{10}$ (FIGS. 10C and D) and PO$_0$ (Figures E and F), as confirmed via acute (2 days) histopathological analysis (FIGS. 10A, 10C and 10E). Injection of the PO$_{100}$H$_{30}$ and PO$_{100}$A$_{30}$ precursors resulted in minimal leukocytotic infiltration at the hydrogel-tissue interface (~100 mm$^{-2}$) two days post-injection (FIG. 10A), suggesting a relatively mild acute inflammatory reaction to the hydrogel. The PO$_{100}$ hydrogel fully degraded within the subcutaneous space after one month (FIG. 7B), and no signs of chronic inflammation were observed at this time point (i.e. no macrophage, foreign body giant cells, fibrous capsule, or granulation tissue was observed histopathologically). Hence, PO$_{100}$ appears to be tolerated in vivo, analogous to conventional PEG hydrogels. Co-injection of PO$_{10}$H$_{30}$ and PO$_{10}$A$_{30}$ precursors results in significantly higher leukocyte infiltration two days post-injection (~500 mm$^{-2}$ at the hydrogel-tissue interface, FIG. 10C). The 30 day chronic time point data indicates that the gel remains present but exhibits evidence of at least partial degradation, with clear ridging observed in the residual hydrogel sample (FIG. 10D). Cellular infiltration at the hydrogel-tissue interface is still present at this stage; however, the cellular density is significantly reduced (~75 mm$^{-2}$) However, no chronic foreign body response is observed at this time point, and the presence of polymorphonuclear neutrophils even 30 days post-injection demonstrates an ongoing infiltrative response toward the material likely mediated by the presence of precursor chains following its biodegradation. Thus, the PO$_{10}$ gel both facilitates slower degradation and elicits a somewhat stronger inflammatory response than the high transition temperature PO$_{100}$ gel, consistent with the relative hydrophilicities of both hydrogels suggested by in vitro swelling measurements. However, given that no fibrous capsule formation is observed and the degree of chronic inflammation is quite mild compared to many other biomaterials, the PO$_{10}$ hydrogel is well-tolerated in vivo. Co-injection of PO$_0$H$_{30}$ and PO$_0$A$_{30}$ reveals leukocyte infiltration toward the interface of the hydrogel at a cell concentration of ~500 mm$^{-2}$, similar to the PO$_{10}$ gels but significantly higher than the PO$_{100}$ gels. By contrast, however, histopathological analysis of the acute incubation of the PO$_0$ gels within the subcutaneous space shows that the gel remains fully intact over the span of 30 days (FIG. 10F). In addition, chronic inflammation of the tissue surrounding the injected hydrogel is apparent even at the chronic time interval, with a retained cell density of ~500 mm$^{-2}$ along with the presence of granulation tissue and neovascularization.

Injectable, hydrazone-crosslinked hydrogels based on POEGMA prepared with mixtures of long (n=8-9) and short (n=2) ethylene oxide side chains easily tunable in situ gelling biomaterials. By tuning the M(EO)$_2$MA (n=2): OEGMA$_{475}$ (n=8-9) ratio in the preparation of reactive POEGMA gel precursors, the properties of the resulting hydrogels can be tuned to meet the needs of multiple biomedical applications. The variance in mechanical strength (1 kPa<G'<25 kPa), swelling (4.0<$Q_m$, <16.5) and degradation (10 min to >7 days) achievable by incorporating M(EO)$_2$MA monomer into the hydrogel, making such hydrogels useful even in cases in which hydrogel thermo-responsivity of is not itself targeted. In addition, the ability to turn cell adhesion effectively on and off to these hydrogels by adjusting monomer ratio and (in the case of PO$_0$) temperature offers potential to apply these materials in (for example) tissue engineering applications not readily served by conventional PEG hydrogels (at least without surface modification). Finally, these POEGMA-based hydrogels offer the potential to reproduce the essential functional properties of PEG hydrogels (PO$_{100}$) and PNIPAM hydrogels (PO$_{10}$) while mitigating the challenges associated with each of those two polymers (tuning cross-link density and functionalization of PEG and ensuring the biocompatibility of PNIPAM in vivo).

Example 2: Layer-by-layer Assembly of Protein-Repellant Surfaces Enabled by POEGMA Hydrazone Chemistry Method POEGMA-hydrazide and POEGMA-aldehyde polymers prepared from Example 1, were first dissolved in 4% (w/v) phosphate buffered saline (PBS) solutions. Samples of Whatman 40# ashless filter paper were cut into small pieces (1 cm×2 cm) or strips (0.8 cm×8 cm) and then dipped in the polymer solutions by completely submerging the paper in the solution. POA was used in the first dipping step for all reported experiments since initiating the sequential dipping with POA instead of POH was demonstrated in preliminary work to facilitate improved protein repellency; we attribute this result to the enhanced affinity between aldehyde-functionalized POA and paper, which can more effectively anchor the POEGMA polymer to the fiber network. After 4 h of gentle shaking (~30 rpm) at room temperature, the paper samples were removed from the solution and washed twice with PBS. Afterwards, all the samples were dried overnight at ambient conditions (~23° C. and ~30% relative humidity). Subsequently, the dried paper was dipped in the 4% (w/v) POH solution for another 4 hours and then washed and dried using the same procedure outlined above. It should be noted that preliminary work was performed to investigate the utility of multiple dipping cycles on the ability of the dip-modified paper to suppress non-specific protein adsorption. While step-by-step mass gain (i.e. POEGMA adsorption or grafting) was achieved on sequential dipping cycles, no significant improvement in protein repellency was observed; as such, a single dipping cycle is sufficient to impart functionality.

Results & Discussion

Based on fluorescent labeling of the POA (aldehyde) and POH (hydrazide) polymers with separate fluorophores, the polymers are effectively co-localized on the cellulose fibers of the filter paper. Scanning electron microscopy (SEM) images at 100× (FIGS. 18A-C) and 500× (FIGS. 18D-F) of 40# filter paper alone (FIGS. 18A and D), filter paper coated with POA alone (FIGS. 18B and E) and filter paper coated sequentially with POA and POH (FIGS. 18C and F) illustrate this localization and network formation occurs without significantly altering the microporosity of the filter paper which maintains the lateral flow and morphological advantages of paper or other porous materials (e.g. membranes) for applications in bioseparations or biosensing.

Chemical analysis of the residual hydrazide and aldehyde functional groups following each dipping step with or without POA and POH precursor coating was conducted. The aldehyde and hydrazide groups were labeled with fluorescein-5-thiosemicarbazide (5-FTSC) and 5-fluorescein isothiocyanate (5-FITC) respectively. The fluorescence intensity of the paper samples was measured by fluorescent plate reader at the excitation wavelength of 488 nm and emission wavelength of 535 nm and normalized to the results obtained with unmodified 40# filter paper. The chemical analysis illustrated show that hydrazide groups are consumed upon aldehyde polymer addition and vice versa, indicating that (1) the polymers do adsorb to the cellulose fibers and (2) covalent bond formation is occurring to form a thin hydrogel film on the fiber surface (FIG. 19). FIG. 20 illustrates a comparison of protein adsorption between unmodified and POA/POH dip-coated polymer hydrogel modified surfaces for (a) Whatman 40# filter paper (porous cellulose substrate) and (b) cellulose-coated quartz crystal microbalance chip (solid cellulose substrate). The resulting coated surfaces exhibited lower protein adsorption for a variety of proteins of different charges and molecular weights (FIG. 20A), with at least four-fold reductions in adsorbed protein amounts demonstrated for each protein tested on coated Whatman 40# cellulose filter paper. Analogously, when layer-by-layer assembly of the POEGMA hydrogel film was conducted on a solid cellulose-coated quartz crystal microbalance chip, at least ten-fold reductions in protein adsorption were achieved across the full spectrum of protein properties tested (FIG. 20B). Thus, this sequential dip coating strategy, enabled by the in situ-gelling properties of the POEGMA precursor polymers, represents an effective and surface modification chemistry-free strategy to coat both solid surfaces as well as porous surfaces, in the latter case without significantly changing the microporosity of the surface. In these applications (e.g., bio-separation membranes and biosensors), in which the layer-by-layer covalent dip-coating process offers a benefit for surface functionalization of protein-repellent gel layers but long-term storage stability of the hydrogel is either beneficial or required, the hydrazone bonds (i.e. the cross-linking bonds) are reduced using a suitable reducing agent to form irreversible hydrazine bonds resulting in a non-degradable hydrogel as shown in Example 4.

Using the layer-by-layer dipping technique with the precursor polymers of the disclosure to prepare such stable hydrogels, the hydrogels reduce the fouling response in bio-separation applications (i.e. avoiding blockages of pores in complex media that would limit throughput or require membrane replacement or cleaning), and non-specific adsorption responses in biosensor applications (i.e. ensuring that binding of the target analyte is not blocked by non-specific binding of off-target analytes from complex media such as blood plasma, an event that would both reduce the sensitivity as well as the signal-to-noise ratio of such sensors).

Example 3: Facile Functionalization of POEGMA Hydrogels Via Copolymerization of Functional Monomers (i) Hydrophobically-Modified POEGMA Hydrogels Via Copolymerization with Oligo(Lactic Acid Methacrylate) (OLA):

Using oligo(lactic acid methacrylate) (OLA) as a monomer in the hydrogel preparation allows for hydrophobic drug binding and delivery using such hydrogels.

Copolymerization of OEGMA with oligo(lactic acid) methacrylate (OLA) to form hydrophobically functionalized POEGMA precursor polymers was investigated as these materials can (1) self-associate via OLA-OLA interactions to form hydrophobic nanodomains enabling significantly enhanced protein and hydrophobic drug binding and (2) can cross-link by both hydrophobic associations and covalent hydrazone chemistry, with the competition between the two chemistries enabling decoupling of gel mechanics and gel degradation. While oligo(lactic acid) was used as the hydrophobic side chain in this specific example, the same technique could be used to form associative POEGMA hydrogels with any unsaturated side chain, including those based on degradable polymers (e.g. poly(glycolic acid) or mixtures of lactic acid and glycolic acid repeat units (PLGA), polycaprolactone, etc.) as well as non-degradable aliphatic groups of any length, provided that the precursor monomers can be dissolved in a solvent compatible with the OEGMA monomers used to form the precursor polymers.

POEGMA hydrogels with associative hydrophobic domains have also been prepared by synthesizing a $PO_{100}H_{30}$ precursor containing a functional oligo(lactic acid) methacrylate macromonomer ($OLA_m$, where m represents the lactic acid chain length) (Table 3) (32). Co-extrusion with $PO_{100}A_{30}$ results in the formation of POEGMA hydrogels that are both chemically (formation of hydrazone bonds) and physically (association of hydrophobic OLA chains) cross-linked. Hydrogel swelling, degradation and elasticity can be independently tuned using POH-OLA precursors according to the OLA chain length (m=4, 8, or 16) and concentration (z=10, 20, or 30 mol %) (FIG. 11 and FIG. 12). The swelling kinetics of PO-OLA hydrogels ((○) PO, ( ) $PO-OLA_{8-10}$, ( ) $PO-OLA_{8-20}$, ( ), $PO-OLA_{4-10}$, (●, black) $PO-OLA_{16-10}$) in 10 mM PBS were measured at 22° C. (FIG. 11A) and 37° C. (FIG. 11B). The degradation kinetics of the PO-OLA hydrogels ((○) PO, ( ) $PO-OLA_{8-10}$, ( ) $PO-OLA_{8-20}$, ( ) $PO-OLA_{4-10}$, (●, black) $PO-OLA_{16-10}$) in 50 mM HCl were measured at 22° C. (FIG. 12A) as well as the elastic storage modulus (FIG. 12B). SANS analysis of the hydrogel microstructure revealed the presence of hydrophobic associative domains as well as the effect of the competition between physical and chemical cross-linking on the mesh size. Incorporating $OLA_m$ into $PO_{100}H_{30}$ precursors, has an effect on BSA loading (FIG. 13) and release (FIG. 14), while maintain high viability of 3T3 mouse fibroblasts based on the molecular weight distribution (FIG. 15).

Method

Hydrazide-functionalized poly(OEGMA-OLA) copolymers ($PO_xOLA_{m-z}$) were prepared by free radical chain transfer copolymerization of OEGMA, OLA, and acrylic acid, followed by carbodiimide-mediated coupling of an excess of adipic acid dihydrazide, using the same solvents and functionalization chemistries already described. OEGMA monomer mixtures of 10% n=2/90% n=8-9 ($PO_{10}$) or 100% n=8-9 ($PO_{100}$), where n is the number of ethylene glycol repeat units in the OEGMA monomer, were used, the former of which creates a thermoresponsive gel and the latter of which has no thermal phase transition temperature. Similarly, OLA monomers containing m=4, m=8, or m=16 lactic acid repeat units were prepared and copolymerized at overall monomer ratios ranging from z=0-20 mol % to vary the hydrophobic driving force for POLA self-assembly. Cross-linking was performed using aldehyde-functionalized POEGMA polymers with the same OEGMA monomer ratio. Copolymers were evaluated by $^1$H-NMR, conductometric titration, and gel permeation chromatography. Hydrogel swelling and degradation were tracked gravimetrically in accelerated conditions (0.1 M HCl, FIG. 21A) as well, the elastic storage modulus G' (FIG. 21B) was measured. Small angle neutron scattering was used to confirm the domain structure of the hydrogels. Fluorescein-labeled bovine serum albumin (BSA) was used as a model therapeutic for loading and release experiments.

Results & Discussion

Gelation of OLA-containing oligomers was significantly faster than that of OEGMA-only oligomers, owing to the presence of the hydrophobic intrachain interactions. Note that the n=16 PLA sample exhibits by far the fastest degradation time of all hydrogels but also exhibits the highest G' value; this result is consistent with the dual cross-linking within these hydrogels, as the physical associations between OLA groups enhance the gel mechanics but can also be more easily disrupted upon dilution or acid treatment (which degrades the OLA polymer). Hydrogels prepared using oligomers containing longer or higher concentration OLA monomer concentrations exhibited stronger mechanics but faster degradation (FIG. 21), owing to higher physical cross-link densities (via OLA self-association) competing with the formation of the more stable hydrazone covalent bond, which represents a mechanism to decouple gel mechanics and degradability which is not directly translatable to PEG-based materials, since adding other types of functional groups necessarily requires decreasing the number of functional groups available for covalent cross-linking (i.e. the number of reactive sites is fixed by the number of PEG chain ends in the sample).

Small angle neutron scattering confirmed the presence of self-assembled domains in OLA-containing hydrogels on the tens of nanometer scale, and pyrene fluorescence assays confirm their hydrophobic nature. $PO_{100}OLA$ polymers self-assembled but did not show lower critical solution temperature (LCST) behavior; $PO_{10}OLA$ polymers all showed distinct LCSTs that were decreased with higher OLA loadings, showing that these materials can be tuned in the same way as the base POEGMA hydrogels as seen in Example 1. However, the volume phase transition temperature behavior and the swelling kinetics of the resulting hydrogels were not significantly affected by the incorporation of OLA (FIG. 22A), suggesting that the OLA groups are self-associating and thus phase separating within the material as to have minimal impact on the behavior of the POEGMA component of the gel. In contrast, protein adsorption is significantly increased as more OLA (higher z) of longer chain lengths (higher m) is incorporated into the gels, with thermoresponsive $PO_{10}OLA$ gels further enhancing protein uptake at 37° C. (FIG. 22B). Reduction of BSA release kinetics is also observed in the $PO_{10}OLA$ gels with OLA incorporated (FIG. 22C), consistent with enhanced affinity between loaded BSA and the hydrogel.

Hydrophobic gel modification via simple copolymerization can be used as a strategy to alter the functionality of these hydrogels for delivering both proteins with affinity for hydrophobic phases as well as small molecule hydrophobic drugs currently challenging to deliver using hydrogel-based materials that maintain comparatively low non-specific protein adsorption (and thus likely lower potential for local inflammation) to other reported hydrophobic drug delivery vehicles.

(ii) Charged, pH-Responsive POEGMA Hydrogels:

As evidenced, functionalization of the hydrogels alters the swelling properties of the gels, can provide specific affinity sites for the binding of drugs, analytes, or cells, can introduce new types of cross-linking or intermolecular interactions to alter gel mechanics and/or degradation, or create properties (e.g. pH responsiveness) to expand the stimulus-responsive potential of such materials, all while maintaining the injectability/layer-by-layer assembly of the hydrogel and the low non-specific protein adsorption facilitated by POEGMA.

Method

Linear hydrazide functionalized POEGMA precursors ($PO_{100}H_{30}$), and ($PO_{10}H_{30}$) were synthesized as described previously. Linear cationic hydrazide functionalized POEGMA precursors ($PO_{100}H_{30}$-cat) and ($PO_{10}A_{30}$-cat) were synthesized by incorporating AIBMe (37 mg, 0.14 mmol), $OEGMA_{475}$ (4.0 g, 6.4 mmol), functional monomer DMEAMA (20 mol %), AA (0.36 g, 5.0 mmol), and TGA (1 μL, 0.03 mmol) in 1,4-dioxane (20 mL). After purging for 30 min, the flask was sealed and submerged in a pre-heated oil bath at 75° C. for 4 hours under magnetic stirring. The solvent was removed and the polymer dissolved in 100 mL DIW. Adipic acid dihydrazide (4.4 g, 21 mmol) in excess was added, pH lowered to pH=4.75 using 0.1 M HCl, after which EDC (1.6 g, 10.6 mmol) was added and the pH maintained at pH=4.75 by the dropwise addition of 0.1 M HCl over 4 hours. The solution was left to stir overnight, dialyzed against DIW for a minimum of 6 cycles, and lyophilized. The polymers were stored as 20 w/w % solutions in PBS at 4° C.

Linear aldehyde functionalized POEGMA precursor ($PO_{100}A_{30}$) was synthesized as described earlier. Linear anionic aldehyde functionalized POEGMA precursor ($PO_{100}A_{30}$-cat) was synthesized by incorporating AIBMe (37 mg, 0.14 mmol), $OEGMA_{475}$ (4.0 g, 6.4 mmol), DMEMAm (0.90 g, 5.2 mmol), functional monomer AA (20 mol %), and TGA (1 μL, 0.03 mmol) in 1,4-dioxane (20 mL). After purging for at least 30 min, the flask was sealed and submerged in a pre-heated oil bath at 75° C. for 4 hours under magnetic stirring. The solvent was removed, and the polymer was subsequently dissolved in 100 mL of 0.5 M HCl. The solution was left to stir for 24 hours, dialyzed against DIW for a minimum of 6 cycles, and lyophilized.

The degree of functionalization was determined from $^1$H-NMR analysis. The polymers were stored as 20 w/w % solutions in PBS at 4° C. The functionalized precursors are labeled as $ZO_xH/A_yZ'$, where x denotes the mole fraction of $OEGMA_{475}$ among the OEGMA monomers used (the remainder being $M(EO)_2MA$), y denotes the overall mole fraction of AA (among all comonomers) in the synthesis recipe and Z' denotes the overall charge of the polymer (cationic or anionic).

FIG. 23 illustrates the degradation profiles of charged POEGMA hydrogels in 0.1M HCl at 37° C.: (A) $PO_{10}$-based hydrogels: (✵) $PO_{10}H/PO_{10}A$; (▨) $PO_{10}H$-cat/$PO_{10}A$; (⚘) $PO_{10}H/PO_{10}A$-an; (✶) $PO_{10}H$-cat/$PO_{10}A$-an. (B) $PO_{100}$-based hydrogels: (✵) $PO_{100}H/PO_{100}A$; (▨) $PO_{100}H$-cat/$PO_{100}A$; (⚘) $PO_{100}H/PO_{100}A$-an; (✶) $PO_{100}H$-cat/$PO_{100}A$-an.

FIG. 24 illustrates the average elastic storage moduli (G') of charged POEGMA hydrogels at 22° C.: (A) $PO_{10}$-based hydrogels: (✵) $PO_{10}H/PO_{10}A$; (▨) $PO_{10}H$-cat/$PO_{10}A$; (●) $PO_{10}H/PO_{10}A$-an; (❀) $PO_{10}H$-cat/$PO_{10}A$-an. (B) $PO_{100}$-based hydrogels: (o) $PO_{100}H/PO_{100}A$; (▨) $PO_{100}H$-cat/$PO_{100}A$; (●) $PO_{100}H/PO_{100}A$-an; (❀) $PO_{100}H$-cat/$PO_{100}A$-an.

FIG. 25 illustrates the BSA uptake into charged POEGMA hydrogels after 2 hours at 37° C.: (A) $PO_{10}$-based hydrogels: (o) $PO_{10}H/PO_{10}A$; (▨) $PO_{10}H$-cat/$PO_{10}A$; (●) $PO_{10}H/PO_{10}A$-an; (✶) $PO_{10}H$-cat/$PO_{10}A$-an. (B) $PO_{100}$-based hydrogels: (o) $PO_{100}H/PO_{100}A$; (▨) $PO_{100}H$-cat/$PO_{100}A$; (●) $PO_{100}H/PO_{100}A$-an; (❀) $PO_{100}H$-cat/$PO_{100}A$-an FIG. 26 shows the protein release (fluorescein-labeled BSA) from charged $PO_{100}$-based hydrogels at 37° C.: (o) $PO_{100}H/PO_{100}A$; (▨) $PO_{100}H$-cat/$PO_{100}A$; (●) $PO_{100}H/PO_{100}A$-an; (❀) $PO_{100}H$-cat/$PO_{100}A$-an.

Results & Discussion

The incorporation of charge has impacts on the physicochemical properties of the hydrogels. Degradation kinetics are accelerated with the incorporation of cationic charge into the hydrogels, while anionic charge incorporation prolongs degradation compared to cationic, neutral and amphoteric gels (FIG. 23). In addition, hydrogels with single charges have higher elastic moduli than hydrogels prepared without charge in the $PO_{100}$ hydrogels, while the anionic gels exhibit higher G' values than neutral, cationic, or amphoteric hydrogels when incorporated into $PO_{100}$-based precursor polymers (FIG. 24).

Without wishing to be bound by theory, it is hypothesized these results are attributable to the increased water binding inside the hydrogels due to the presence of charges, resulting in higher swelling (and thus higher rates of hydrolysis) in both single charge gels, that is counteracted by the formation of hydrogen bonds between —COOH groups in the charged residues and —OH groups on the OEGMA residues that results in the enhanced mechanics of the anionic hydrogels. The amphoteric hydrogels can form cross-links both via hydrazone bonding and via polyelectrolyte interactions, slightly increasing their mechanics while also slowing their degradation in the $PO_{10}$-based hydrogels. Furthermore, while still low relative to other types of biomaterials, protein adsorption (and thus the affinity of proteins for the hydrogels) is significantly enhanced in the charged (cationic, amphoteric and anionic) gels (FIG. 25), owing to the electrostatic attraction introduced between at least selected domain(s) of the proteins and the hydrogels. Similarly, protein release from amphoteric hydrogels in particular is slowed (FIG. 26) due to the enhanced affinity of the proteins for the gel phase. Thus, by simple copolymerization of one or more pH-ionizable monomers (including those used but also encompassing any vinylic, (meth)acrylic, (meth)acrylamide, allylic, styrenic, or other monomer that contains a monomer that has a $pK_a$ value accessible in an aqueous solvent), charged injectable hydrogels can be produced that retain the thermoresponsive, degradation, and (comparatively) low non-specific protein adsorption properties of the base POEGMA hydrogels.

Example 4: Post-Alteration of Hydrogel Degradation Via Reduction of the Hydrazone Bond Method Neutral POEGMA hydrogels ($PO_{10}$) were formed using the same methods previously outlined. Samples were then exposed to sodium cyanoborohydride (50 mM solution in water for 2 hours) and ascorbic acid (50 mM solution in water for 2 hours) to reduce the hydrazone bond. Following purification by extensive dialysis to remove excess reducing agent (6×6 hours), degradation assays were then performed as previously described using 0.1M HCl, which acid-catalyzes the degradation of the non-reduced hydrazone bond.

Results & Discussion

Treatment of the hydrogel with sodium cyanoborohydride results in a hydrogel that does not functionally degrade over at least 30 hours even when exposed to a highly acidic environment as illustrated in a mass degradation assay in 0.1M HCl (FIG. 27). In contrast, hydrogels not post-treated (i.e. still hydrazone cross-linked) as well as hydrogels treated with ascorbic acid, a much weaker but biologically more tolerated reducing agent, degrade within the first few hours following exposure to acid. As a result, reduction of the hydrazone bond via sodium cyanoborohydride treatment can functionally convert the hydrogel into a non-degradable network, improving the stability of such coatings for biosensors or membranes in particular.

Example 5: Changing Hydrogel Properties by Mixing Precursor Polymers with Different Lower-Critical Solution Temperatures By mixing pairs of hydrazide and aldehyde precursor polymers with different transition temperatures, hydrogels with well-defined phase-separated nanoscale domains were produced (as confirmed by small angle neutron scattering) depending on the ratio of high and low LCST precursor polymer pairs added. Such domains can decouple the bulk and nanoscale properties of injectable thermoresponsive hydrogels.

Methods

Hydrogels were prepared by co-extruding one or more hydrazide-functionalized precursor(s) ($PO_{10}H_{30}$, $PO_{55}H_{30}$ and/or $PO_{100}H_{30}$) with one or more aldehyde-functionalized precursor(s) ($PO_{10}A_{30}$, $PO_{55}A_{30}$ and/or $PO_{100}A_{30}$), produced as previously described, using a double barrel syringe (Medmix) Each barrel contained polymer at a total concentration of 150 mg/mL in 10 mM PBS. Hydrogel disks for swelling, degradation and transparency measurements were prepared by extruding the reactive polymer precursors through the double barrel syringe into cylindrical silicone rubber molds (diameter=7 mm, volume=300 up. In all cases, gels were incubated at room temperature for at least 12 hours to ensure complete gelation prior to testing.

Three categories of hydrogels were prepared. First, single precursor, same LCST hydrogels were prepared by co-extruding hydrazide and aldehyde precursors with the same OEGMA co-monomer content (i.e. similar LCST values), analogous to those previously described (PO(100/0)= $PO_{10}H_{30}+PO_{10}A_{30}$; $PO_{55}=PO_{55}H_{30}+PO_{55}A_{30}$; PO(0/100)= $PO_{100}H_{30}+PO_{100}A_{30}$). Second, single precursor, different LCST hydrogels were prepared by mixing precursors with different OEGMA comonomer contents (i.e. different LCST values) (PO(L/H)=$PO_{10}H_{30}+PO_{100}A_{30}$; PO(H/L)= $PO_{100}H_{30}+PO_{10}A_{30}$). Finally, mixed precursor hydrogels (PO(75/25), PO(50/50) and PO(25/75)) were prepared by mixing both high LCST ($PO_{100}$) and low LCST ($PO_{10}$) precursor polymers in both the hydrazide ($PO_{10}H_{30}$ and $PO_{100}H_{30}$) and aldehyde ($PO_{10}A_{30}$ and $PO_{100}A_{30}$) barrels of the double barrel syringe at the ratios indicated by the hydrogel sample code ($PO_{10}/PO_{100}$ content) at a total concentration of 150 mg/mL in 10 mM PBS. The difference between these groups is that each mixed precursor hydrogel is prepared by mixing four (2 hydrazide-functionalized and 2 aldehyde-functionalized) precursor polymers with different LCST values, while the single precursor hydrogels are prepared by mixing only two (1 hydrazide-functionalized and 1 aldehyde-functionalized) precursor polymers which may have the same or different LCST values (Table 4). All analysis was done consistent with previously described methods.

Results

By mixing precursor polymers with different properties, the macroscopic and microscopic properties of the mixed precursor hydrogels can be decoupled. Macroscopically, gelation rates, swelling kinetics, degradation kinetics, and mechanical properties of the hydrogels can be predicted by a simple rule of mixtures (for example, see FIG. 28 for shear storage modulus; similar results were acquired for the other macroscopic properties mentioned). FIG. 28 shows the average shear storage moduli (G') of the fully swollen mixed precursor POEGMA hydrogels as a function of the weight fraction of high LCST precursor polymers used to prepare the hydrogels (Correlation: G'=7.97±0.33−(0.065±0.004)x; $R^2$=0.984. n=3; error bars represent the standard deviation of three independently extruded hydrogel disks). Microscopically, phase separated domains result in localized phase transitions within the hydrogels, inducing changes in protein affinity (with higher protein binding observed in mixtures than in either single-component hydrogel, FIG. 29), drug release kinetics (with substantially slower protein release for bovine serum albumin observed from the mixed precursor hydrogels as opposed to single component hydrogels, particularly when the gel was extruded at a temperature above the LCST of the lower phase transition temperature polymer as shown in FIG. 30) optical transparency (with significantly higher turbidity in samples prepared with mixed precursors), and cell adhesion (with higher cell adhesion observed in mixed precursor gels versus either single component hydrogel). FIG. 29 shows (A) Bovine serum albumin (BSA), (B) fibrinogen (Fib), and (C) immunoglobulin G (IgG) uptake (expressed as ng per cross-sectional area of hydrogel) to POEGMA hydrogels; n=4; error bars represent the standard deviation of four independently extruded hydrogel disks. FIG. 30 shows BSA release kinetics at 37° C. for the POEGMA hydrogels prepared at (A) 22° C. and (B) 37° C.; (●) PO(100/0); (※) PO(75/25); (※)PO(50/50); (○) PO(25/75) and (※) PO(0/100). n=4; error bars represent the standard deviation of four independently extruded hydrogel disks.

Furthermore, mixing of precursors can be used to straightforwardly tune the hydrogel properties according to the desired application while circumventing the need to synthesize and test a vast library of POEGMA precursor polymers. For example, by mixing the high and low LCST precursor polymers together in different ratios, a M(EO)$_2$MA: OEGMA$_{475}$ composition of x=55 mol % (i.e. PO(50/50)) was identified as a desired zero-swelling hydrogel composition ideal for space-filling applications in vivo (such as vitreous humor replacement, for which hydrogel swelling/ de-swelling over time must be avoided to avoid glaucoma). Further, this zero-swelling property is maintained in the absence of any kind of pre-swelling equilibrium, enabling direct injection of the precursors in a phosphate buffer solution. Hydrogels prepared from precursor polymers with this same M(EO)$_2$MA:OEGMA$_{475}$ ratio ($PO_{55}H_{30}$ and $PO_{55}A_{30}$, Table 4) as well as mixtures of one low LCST and one high LCST precursor with complementary reactivities that also maintain the same overall M(EO)$_2$MA:OEGMA$_{475}$ ratio (PO(L/H) and PO(H/L), Table 4) each exhibited mass-based swelling ratios $Q_m$ within 10% of each other at 37° C. and shear storage moduli within experimental error (p>0.05 for all pair-wise comparisons, Table 5). In contrast, the $PO_{55}$ hydrogel exhibits transparency (similar to $PO_{100}$) at 37° C. and the single precursor (same LCST) hydrogels are also largely transparent, while the corresponding mixed precursor hydrogel is effectively opaque (Table 5). Together, these results indicate using a mixing approach to identify hydrogels with similar macroscopic properties but different microstructures.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1 shows the characterization of synthesized POEGMA polymer precursors.

| | Functional Group [—] | Theoretical Functional Monomer [mol %]$^a$ | Actual OEGMA$_{475}$ [mol %] | Actual Functional Monomer [mol %]$^b$ | $M_n$ [×10$^3$ g·mol$^{-1}$]$^c$ | Đ [—]$^d$ | Average # of Functional Groups/Chain |
|---|---|---|---|---|---|---|---|
| PO$_{100}$H$_{20}$ | NHNH$_2$ | 20.0 | 81.8 | 18.2 | 16.9 | 2.66 | 8 |
| PO$_{100}$A$_{25}$ | NHNH$_2$ | 25.0 | 77.9 | 22.1 | 18.1 | 2.43 | 10 |
| PO$_{100}$H$_{30}$ | NHNH$_2$ | 30.0 | 72.8 | 27.2 | 19.4 | 2.35 | 16 |
| PO$_{100}$H$_{40}$ | NHNH$_2$ | 40.0 | 64.4 | 35.6 | 19.1 | 3.15 | 20 |
| PO$_{100}$A$_{20}$ | CHO | 20.0 | 82.7 | 17.3 | 19.5 | 3.15 | 7 |
| PO$_{100}$A$_{25}$ | CHO | 25.0 | 75.2 | 24.8 | 17.9 | 2.87 | 9 |
| PO$_{100}$A$_{30}$ | CHO | 30.0 | 71.9 | 28.1 | 19.3 | 2.43 | 12 |
| PO$_{100}$A$_{40}$ | CHO | 40.0 | 60.2 | 39.8 | 20.3 | 3.21 | 17 |

TABLE 2 shows the chemical characterization of the various thermoresponsive POEGMA precursors.

| | Funct. Mon [—] | M(EO)$_2$MA$^a$ [mol %] | OEGMA$_{475}$$^a$ [mol %] | Funct mon [mol %] | $M_n$ [10$^3$ g·mol$^{-1}$] | Đ [—] | Funct. groups [#/chain] | LCST$^c$ [° C.] |
|---|---|---|---|---|---|---|---|---|
| PO$_0$H$_{30}$ | NHNH$_2$ | 77.1 | 0.0 | 22.9$^b$ | 16.2 | 2.41 | 24 | 51.0 |
| PO$_{10}$H$_{30}$ | NHNH$_2$ | 72.5 | 5.9 | 21.6$^b$ | 17.0 | 1.59 | 22 | 63.1 |
| PO$_{100}$H$_{30}$ | NHNH$_2$ | 0.0 | 72.8 | 27.2$^b$ | 19.4$^d$ | 2.35$^d$ | 16 | >80$^e$ |
| PO$_0$A$_{30}$ | CHO | 80.6 | 0.0 | 19.4$^a$ | 16.9 | 2.49 | 17 | 40.1 |
| PO$_{10}$A$_{30}$ | CHO | 70.4 | 5.7 | 23.9$^a$ | 13.0 | 2.03 | 19 | 53.6 |
| PO$_{100}$A$_{30}$ | CHO | 0.0 | 71.9 | 28.1$^a$ | 18.3$^d$ | 2.43$^d$ | 16 | >80$^e$ |

$^a$Determined by $^1$H-NMR,
$^b$Determined from conductometric titration
$^c$ Determined at 95% transmittance at 1 mg/mL in PBS
$^d$Measured in aqueous-SEC using an acetate buffer
$^e$no LCST was observed up to 80° C.
Nomenclature: PO$_x$H$_y$; x represents the mol fraction of OEGMA$_{475}$ of the OEGMA monomers used and y represents the theoretical mol fraction of functional monomer (hydrazide or aldehyde).
$^a$Theoretical degree of functionalization in mol %,
$^b$Experimental degree of functionalization as determined from conductometric base-into-acid titration for the hydrazide precursors or from $^1$H-NMR for the aldehyde precursors,
$^c$ Determined using aqueous GPC with a mobile phase consisting of 0.3M sodium nitrate and 0.05M phosphate buffer at pH 7,
$^d$Dispersity (Đ) as determined from aqueous GPC

TABLE 3 shows the chemical synthesis of the PHO-OLA hydrazide-functionalized polymers.

| | m [—] | OEGMA$_{475}$ [g] | OLA [g] | AA [µL] | AIBMe [mg] |
|---|---|---|---|---|---|
| POH | — | 4.0 | 0.0 | 286 | 35 |
| POH-OLA$_{4-10}$ | 4 | 2.5 | 0.37 | 181 | 35 |
| POH-OLA$_{8-10}$ | 8 | 2.5 | 0.62 | 181 | 35 |
| POH-OLA$_{8-20}$ | 8 | 2.0 | 1.20 | 171 | 35 |
| POH-OLA$_{8-30}$ | 8 | 1.2 | 1.32 | 129 | 18 |
| POH-OLA$_{16-10}$ | 16 | 2.5 | 1.12 | 181 | 35 |

TABLE 4

Compositions of the various POEGMA hydrogels studied in mixed precursor work

| | Hydrazide Barrel | | | Aldehyde Barrel | | |
|---|---|---|---|---|---|---|
| | PO$_{10}$H$_{30}$ [mg/mL] | PO$_{55}$H$_{30}$ [mg/mL] | PO$_{100}$H$_{30}$ [mg/mL] | PO$_{10}$A$_{30}$ [mg/mL] | PO$_{55}$A$_{30}$ [mg/mL] | PO$_{100}$A$_{30}$ [mg/mL] |
| PO$_{10}$ = PO(100/0) | 150.0 | — | — | 150.0 | — | — |
| PO(75/25) | 112.5 | — | 37.5 | 112.5 | — | 37.5 |
| PO(50/50) | 75.0 | — | 75.0 | 75.0 | — | 75.0 |
| PO(25/75) | 37.5 | — | 112.5 | 37.5 | — | 112.5 |

TABLE 4-continued

Compositions of the various POEGMA hydrogels studied in mixed precursor work

| | Hydrazide Barrel | | | Aldehyde Barrel | | |
|---|---|---|---|---|---|---|
| | $PO_{10}H_{30}$ [mg/mL] | $PO_{55}H_{30}$ [mg/mL] | $PO_{100}H_{30}$ [mg/mL] | $PO_{10}A_{30}$ [mg/mL] | $PO_{55}A_{30}$ [mg/mL] | $PO_{100}A_{30}$ [mg/mL] |
| $PO_{100}$ = PO(0/100) | — | — | 150.0 | — | — | 150.0 |
| PO(L/H) | 150.0 | — | — | — | — | 150.0 |
| PO(H/L) | — | — | 150.0 | 150.0 | — | — |
| $PO_{55}$ | — | 150.0 | — | — | 150.0 | — |

TABLE 5

Comparison of the equilibrium swelling ratios, shear storage moduli and transmittance values of the mixed precursor, single precursor (different LCST), and single precursor (same LCST) hydrogels prepared with the same overall $M(EO)_2MA:OEGMA_{475}$ comparison (x = 55 mol %)

| Hydrogel | $Q_m$ (22° C.) [—] | $Q_m$ (37° C.) [—] | G'(22° C.) [kPa] | Transmittance % (37° C.) |
|---|---|---|---|---|
| PO(50/50) | 9.5 ± 0.5 | 8.1 ± 0.1 | 4.9 ± 0.5 | 40.4 |
| PO(L/H) | 11.9 ± 0.4 | 8.0 ± 0.2 | 5.5 ± 0.6 | 98.0 |
| PO(H/L) | 12.3 ± 0.2 | 7.6 ± 0.1 | 5.3 ± 0.4 | 87.4 |
| $PO_{55}$ | 10.0 ± 0.4 | 7.4 ± 0.0 | 5.1 ± 0.1 | 96.8 |

REFERENCES

1. C.-C. Lin, K. S. Anseth, PEG hydrogels for the controlled release of biomolecules in regenerative medicine, Pharm. Res. 26 (2009) 631-43.
2. J. L. Drury, D. J. Mooney, Hydrogels for tissue engineering: scaffold design variables and applications, Biomaterials. 24 (2003) 4337-4351.
3. N. a. Peppas, J. Z. Hilt, a. Khademhosseini, R. Langer, Hydrogels in Biology and Medicine: From Molecular Principles to Bionanotechnology, Adv. Mater. 18 (2006) 1345-1360.
4. J. Jokerst, T. Lobovkina, R. N. Zare, S. S. Gambhir, Nanoparticle PEGylation for imaging and therapy, Nanomedicine. 6 (2011) 715-728.
5. C. R. Nuttelman, M. a Rice, A. E. Rydholm, C. N. Salinas, D. N. Shah, K. S. Anseth, Macromolecular Monomers for the Synthesis of Hydrogel Niches and Their Application in Cell Encapsulation and Tissue Engineering, Prog. Polym. Sci. 33 (2008) 167-179.
6. M. Malkoch, R. Vestberg, N. Gupta, L. Mespouille, P. Dubois, A. F. Mason, et al., Synthesis of well-defined hydrogel networks using Click chemistry, Chem. Commun. (2006) 2774.
7. J. D. McCall, K. S. Anseth, Thiol-ene photopolymerizations provide a facile method to encapsulate proteins and maintain their bioactivity, Biomacromolecules. 13 (2012) 2410-7.
8. A. a Aimetti, A. J. Machen, K. S. Anseth, Poly(ethylene glycol) hydrogels formed by thiol-ene photopolymerization for enzyme-responsive protein delivery, Biomaterials. 30 (2009) 6048-54.
9. Y. Fu, W. J. Kao, In situ forming poly(ethylene glycol)-based hydrogels via thiol-maleimide Michael-type addition, J. Biomed. Mater. Res. A. 98 (2011) 201-11.
10. M. P. Lutolf, J. a Hubbell, Synthesis and physicochemical characterization of end-linked poly(ethylene glycol)-co-peptide hydrogels formed by Michael-type addition, Biomacromolecules. 4 (2003) 713-22.
11. S. P. Zustiak, J. B. Leach, Hydrolytically degradable poly(ethylene glycol) hydrogel scaffolds with tunable degradation and mechanical properties, Biomacromolecules. 11 (2010) 1348-57.
12. B. D. Polizzotti, B. D. Fairbanks, K. S. Anseth, Three-dimensional biochemical patterning of click-based composite hydrogels via thiolene photopolymerization, Biomacromolecules. 9 (2008) 1084-7.
13. K. C. Koehler, K. S. Anseth, C. N. Bowman, Diels-Alder mediated controlled release from a poly(ethylene glycol) based hydrogel, Biomacromolecules. 14 (2013) 538-547.
14. G. N. Grover, J. Lam, T. H. Nguyen, T. Segura, H. D. Maynard, Biocompatible hydrogels by oxime Click chemistry, Biomacromolecules. 13 (2012) 3013-7.
15. H. Saito, a. S. Hoffman, H. I. Ogawa, Delivery of Doxorubicin from Biodegradable PEG Hydrogels Having Schiff Base Linkages, J. Bioact. Compat. Polym. 22 (2007) 589-601.
16. B. Farrugia, K. Kempe, U.S. Schubert, R. Hoogenboom, T. R. Dargaville, Poly(2-oxazoline) Hydrogels for Controlled Fibroblast Attachment, Biomacromolecules. (2013).
17. J.-F. Lutz, Polymerization of oligo(ethylene glycol) (meth)acrylates: Toward new generations of smart biocompatible materials, J. Polym. Sci. Part A Polym. Chem. 46 (2008) 3459-3470.
18. M. Luzon, C. Boyer, C. Peinado, T. Corrales, M. Whittaker, L. E. I. Tao, et al., Water-Soluble, Thermoresponsive, Hyperbranched Copolymers Based on PEG-Methacrylates: Synthesis, Characterization, and LCST Behavior, 48 (2010) 2783-2792.
19. A. H. Soeriyadi, G.-Z. Li, S. Slavin, M. W. Jones, C. M. Amos, C. R. Becer, et al., Synthesis and modification of thermoresponsive poly(oligo(ethylene glycol) methacrylate) via catalytic chain transfer polymerization and thiol-ene Michael addition, Polym. Chem. 2 (2011) 815-822.
20. J. K. Oh, K. Min, K. Matyjaszewski, Preparation of Poly(oligo(ethylene glycol) monomethyl ether methacrylate) by Homogeneous Aqueous AGET ATRP, Macromolecules. 39 (2006) 3161-3167.
21. J.-F. Lutz, A. Hoth, Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate, Macromolecules. 39 (2006) 893-896.
22. J.-F. Lutz, J. Andrieu, S. Uzgun, C. Rudolph, S. Agarwal, Biocompatible, Thermoresponsive, and Biodegradable: Simple Preparation of "All-in-One" Biorelevant Polymers, Macromolecules. 40 (2007) 8540-8543.
23. J. Lei, C. Mayer, V. Freger, M. Ulbricht, Synthesis and Characterization of Poly(ethylene glycol) Methacrylate Based Hydrogel Networks for Anti-Biofouling Applications, Macromol. Mater. Eng. (2012).
24. R. Paris, I. Quijada-Garrido, Swelling behaviour of thermo-sensitive hydrogels based on oligo(ethylene glycol) methacrylates, Eur. Polym. J. 45 (2009) 3418-3425.
25. J. A. Yoon, C. Gayathri, R. R. Gil, T. Kowalewski, K. Matyjaszewski, Comparison of the Thermoresponsive Deswelling Kinetics of Poly(2-(2-methoxyethoxy)ethyl methacrylate) Hydrogels Prepared by ATRP and FRP, Macromolecules. 43 (2010) 4791-4797.
26. J. A. Yoon, T. Kowalewski, K. Matyjaszewski, Comparison of Thermoresponsive Deswelling Kinetics of Poly (oligo (ethylene oxide) methacrylate)-Based Thermoresponsive Hydrogels Prepared by "Graft-from" ATRP, (2011) 2261-2268.
27. J.-F. Lutz, K. Weichenhan, O. Akdemir, A. Hoth, About the Phase Transitions in Aqueous Solutions of Thermoresponsive Copolymers and Hydrogels Based on 2-(2-methoxyethoxy)ethyl Methacrylate and Oligo(ethylene glycol) Methacrylate, Macromolecules. 40 (2007) 2503-2508.
28. N. Fechler, N. Badi, K. Schade, S. Pfeifer, J.-F. Lutz, Thermogelation of PEG-Based Macromolecules of Controlled Architecture, Macromolecules. 42 (2009) 33-36.
29. N. M. B. Smeets, E. Bakaic, M. Patenaude, T. Hoare, Injectable and tunable poly(ethylene glycol) analogue hydrogels based on poly(oligoethylene glycol methacrylate), Chem. Commun (Camb). 50 (2014) 3306-9.
30. G. Pasut, F. M. Veronese, Polymer-drug conjugation, recent achievements and general strategies, Prog. Polym. Sci. 32 (2007) 933-961.
31. N. M. B. Smeets, E. Bakaic, M. Patenaude, T. Hoare, Injectable poly(oligoethylene glycol methacrylate)-based hydrogels with tunable phase transition behaviours: Physicochemical and biological responses, Acta Biomater. (2014).
32. N. M. B. Smeets, M. Patenaude, D. Kinio, F. M. Yavitt, E. Bakaic, F.-C. Yang, et al., Injectable hydrogels with in situ-forming hydrophobic domains: oligo(d, l-lactide) modified poly(oligoethylene glycol methacrylate) hydrogels, Polym. Chem. (2014).
33. G. N. Grover, R. L. Braden, K. L. Christman, Oxime Cross-Linked Injectable Hydrogels for Catheter Delivery, Adv. Mater. (2013) 1-6.
34. D. E. Discher, D. J. Mooney, P. W. Zandstra, NIH Public Access, 324 (2010) 1673-1677.
35. S. Pasche, S. M. Paul, J. Voros, N. D. Spencer, M. Textor, Poly(l-lysine)-graft-poly(ethylene glycol) Assembled Monolayers on Niobium Oxide Surfaces: A Quantitative Study of the Influence of Polymer Interfacial Architecture on Resistance to Protein Adsorption by ToF-SIMS and in Situ OWLS, Langmuir. 22 (2003) 9216-9225.
36. Y. Chung, Protein Adsorption and Cell Alignment on Micropatterned Phosphorylcholine Surfaces, 29 (2009) 320-324.
37. K. Y. Suh, J. Seong, A. Khademhosseini, P. E. Laibinis, R. Langer, A simple soft lithographic route to fabrication of poly(ethylene glycol) microstructures for protein and cell patterning, Biomaterials. 25 (2004) 557-563.
38. E. Tziampazis, J. Kohn, P. Moghe, PEG-variant biomaterials as selectively adhesive protein templates: model surfaces for controlled cell adhesion and migration, Biomaterials. 21 (2000) 511-520.
39. A. Shimoda, S. Sawada, A. Kano, A. Maruyama, A. Moquin, F. M. Winnik, et al., Dual crosslinked hydrogel nanoparticles by nanogel bottom-up method for sustained-release delivery, Colloids Surf. B. Biointerfaces. 99 (2012) 38-44.
40. H. Du, P. Chandaroy, S. W. Hui, Grafted poly-(ethylene glycol) on lipid surfaces inhibits protein adsorption and cell adhesion, Biochim. Biophys. Acta-Biomembr. 1326 (1997) 236-248.
41. E. Ruoslahti, RGD and other recognition sequences for integrins, Annu. Rev. Cell Dev. Biol. 12 (1996) 697-715.
42. E. Ruoslahti, M. Pierschbacher, Arg-Gly-Asp: a versatile cell recognition signal, Cell. 44 (1986) 517-518.
43. M. D. Pierschbacher, E. Ruoslahti, Cell attachment activity of fibronectin can be duplicated by small synthetic fragments of the molecule, Nature. 309 (1984) 30-33.
44. U. Hersel, C. Dahmen, H. Kessler, RGD modified polymers: biomaterials for stimulated cell adhesion and beyond, Biomaterials. 24 (2003) 4385-4415.
45. H. T. T. Duong, T. L. Uyen Nguyen, M. H. Stenzel, Micelles with surface conjugated RGD peptide and cross-linked polyurea core via RAFT polymerization, Polym. Chem. 1 (2010) 171-182.
46. F. Yang, C. G. Williams, D. Wang, H. Lee, P. N. Manson, J. Elisseeff, The effect of incorporating RGD adhesive peptide in polyethylene glycol diacrylate hydrogel on osteogenesis of bone marrow stromal cells, Biomaterials. 26 (2005) 5991-5998.
47. J. A. Burdick, K. S. Anseth, Photoencapsulation of osteoblasts in injectable RGD-modified PEG hydrogels for bone tissue engineering, Biomaterials. 23 (2002) 4315-4323.
48. D. Guarnieri, A. Capua, M. Ventre, A. Borzacchiello, C. Pedone, D. Marasco, et al., Covalently immobilized RGD gradient on PEG hydrogel scaffold influences cell migration parameters, Acta Biomater. 6 (2010) 2532-2539.
49. Meid, J., Friedrich, T., Tieke, B., Lindner, P., Richtering, W. Physical Chemistry Chemical Physics. 13, 2011, 3039-3047.
50. Adachi, J., Sato, N. Journal of Organic Chemistry. 37, 1972, 221-225.
51. X.-J. Ju, L.-Y. Chu, X.-L. Zhu, L. Hu, H. Song, W.-M. Chen, Effects of internal microstructures of poly(N-isopropylacrylamide) hydrogels on thermoresponsive volume phase-transition and controlled-release characteristics, Smart Mater. Struct. 15 (2006) 1767-1774. doi: 10.1088/0964-1726/15/6/031.
52. K. Makino, J. Hiyoshi, H. Ohshima, Effects of thermosensitivity of poly (N-isopropylacrylamide) hydrogel upon the duration of a lag phase at the beginning of drug release from the hydrogel, Colloids Surf. B. Biointerfaces. 20 (2001) 341-346.
53. M. A. Cooperstein, H. E. Canavan, Biological cell detachment from poly(N-isopropyl acrylamide) and its applications, Langmuir. 26 (2010) 7695-7707. doi: 10.1021/la902587p.
54. R. M. P. da Silva, J. F. Mano, R. L. Reis, Smart thermoresponsive coatings and surfaces for tissue engineering: switching cell-material boundaries, Trends Biotechnol. 25 (2007) 577-583. doi:10.1016/j.tibtech.2007.08.014.
55. T. Okano, N. Yamada, M. Okuhara, H. Sakai, Y. Sakurai, Mechanism of cell detachment from temperature-modulated, hydrophilic-hydrophobic polymer surfaces, Biomaterials. 16 (1995) 297-303. doi:10.1016/0142-9612(95)93257-E.
56. H. G. Schild, Poly(N-isopropylacrylamide): experiment, theory and application, Prog. Polym. Sci. 17 (1992) 163-249. doi:10.1016/0079-6700(92)90023-R.
57. H. Vihola, A. Laukkanen, L. Valtola, H. Tenhu, J. Hirvonen, Cytotoxicity of thermosensitive polymers poly (N-isopropylacrylamide), poly(N-vinylcaprolactam) and amphiphilically modified poly(N-vinylcaprolactam), Biomaterials. 26 (2005) 3055-3064. doi: 10.1016/j.biomaterials.2004.09.008.
58. M. A. Cooperstein, H. E. Canavan, Assessment of cytotoxicity of (N-isopropyl acrylamide) and Poly(N-isopropyl acrylamide)-coated surfaces—Springer, Biointerphases. 8 (2013).

59. J.-F. Lutz, A. Hoth, Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate, Macromolecules. 39 (2006) 893-896. doi:10.1021/ma0517042

60. S. Sun, P. Wu, On the Thermally Reversible Dynamic Hydration Behavior of Oligo(ethylene glycol) Methacrylate-Based Polymers in Water, Macromolecules. 46 (2013) 236-246. doi:10.1021/ma3022376.

61. M. Luzon, C. Boyer, C. Peinado, T. Corrales, M. Whittaker, L. E. I. Tao, et al., Water-Soluble, Thermoresponsive, Hyperbranched Copolymers Based on PEG-Methacrylates: Synthesis, Characterization, and LCST Behavior, J. Polym. Sci. Part A Polym. Chem. 48 (2010) 2783-2792. doi:10.1002/POLA 62. A. H. Soeriyadi, G.-Z. Li, S. Slavin, M. W. Jones, C. M. Amos, C. R. Becer, et al., Synthesis and modification of thermoresponsive poly(oligo(ethylene glycol) methacrylate) via catalytic chain transfer polymerization and thiol-ene Michael addition, Polym. Chem. 2 (2011) 815-822. doi:10.1039/c0py00372g.

63. J. K. Oh, K. Min, K. Matyjaszewski, Preparation of Poly(oligo(ethylene glycol) monomethyl ether methacrylate) by Homogeneous Aqueous AGET ATRP, Macromolecules. 39 (2006) 3161-3167.

64. J.-F. Lutz, Polymerization of oligo(ethylene glycol) (meth)acrylates: Toward new generations of smart biocompatible materials, J. Polym. Sci. Part A Polym. Chem. 46 (2008) 3459-3470. doi:10.1002/pola.22706.

65. J. Lei, C. Mayer, V. Freger, M. Ulbricht, Synthesis and Characterization of Poly(ethylene glycol) Methacrylate Based Hydrogel Networks for Anti-Biofouling Applications, Macromol. Mater. Eng. 298 (2013) 967-980. doi:10.1002/mame.201200297.

66. R. París, I. Quijada-Garrido, Swelling behaviour of thermo-sensitive hydrogels based on oligo(ethylene glycol) methacrylates, Eur. Polym. J. 45 (2009) 3418-3425. doi: 10.1016/j.eurpolymj.2009.09.012.

67. J. A. Yoon, T. Kowalewski, K. Matyjaszewski, C. Gayathri, R. R. Gil, Comparison of the Thermoresponsive Deswelling Kinetics of Poly(2-(2-methoxyethoxy)ethyl methacrylate) Hydrogels Prepared by ATRP and FRP, Macromolecules. 43 (2010) 4791-4797. doi:10.1021/ma1004953.

68. J. A. Yoon, T. Kowalewski, K. Matyjaszewski, Comparison of Thermoresponsive Deswelling Kinetics of Poly (oligo(ethylene oxide) methacrylate)-Based Thermoresponsive Hydrogels Prepared by "Graft-from" ATRP, Macromolecules. 44 (2011) 2261-2268.

The invention claimed is:

1. A hydrogel composition, comprising
   a. at least one first precursor polymer which is a nucleophile-functionalized poly(oligoethylene glycol) methacrylate) copolymer, and
   b. at least one second precursor polymer which is an electrophile-functionalized poly(oligoethylene glycol) methacrylate) copolymer,
   wherein the first and second precursor polymers are crosslinked through covalent bonds by reaction of the nucleophilic and electrophilic moieties.

2. The hydrogel composition of claim 1, wherein the nucleophile-functionalized poly(oligoethylene glycol) methacrylate) copolymer comprises a nucleophilic moiety which is a hydrazide or amine derivative, a carbonyl hydrate, an alcohol, cyanohydrin or cyanohydrin derivative, a thiol or thiol derivative, or a phosphorus ylide or derivatives thereof.

3. The hydrogel composition of claim 2, wherein the nucleophilic moiety is a hydrazide moiety.

4. The hydrogel composition of claim 1, wherein the electrophile-functionalized poly(oligoethylene glycol) methacrylate) polymer comprises an electrophilic moiety which is an aldehyde, a ketone, a carboxylic acid, an ester, an amide, a maleimide, an acyl (acid) chloride, an acid anhydride or an alkene group or derivatives thereof.

5. The hydrogel composition of claim 4, wherein the electrophilic moiety is an aldehyde or ketone moiety.

6. The hydrogel composition of claim 1, wherein the composition comprises
   a. at least one first precursor polymer which is a hydrazide-functionalized poly(oligoethylene glycol) methacrylate) copolymer, and
   b. at least one second precursor polymer which is an aldehyde- and/or ketone-functionalized poly(oligoethylene glycol methacrylate) copolymer,
   wherein the first and second precursor polymers are crosslinked through hydrazone bonds.

7. The hydrogel composition of claim 6, wherein the first precursor polymer is a copolymer comprising monomeric units of:
   a. a first monomer which is oligoethylene glycol methacrylate, or a derivative thereof; and
   b. at least a second polymerizable monomer which is functionalized or is capable of being functionalized with a hydrazide moiety.

8. The hydrogel composition of claim 7, wherein the first monomer has the structure of the formula (I)

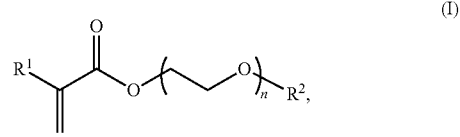

wherein $R^1$ is H, $(C_1-C_{10})$alkyl or $(C_2-C_{10})$alkynyl;

$R^2$ is H, $(C_1-C_{10})$alkyl, $(C_2-C_{10})$alkynyl, —$(C_0-C_4)$-alkylene-$(C_6-C_{10})$aryl, —$(C_0-C_4)$-alkylene-$(C_5-C_{10})$heteroaryl, —C(O)NR' or —C(O)OR', wherein R' is H or $(C_1-C_6)$alkyl, and n is any integer between 6 and 30.

9. The hydrogel composition of claim 8, wherein $R^1$ is H or $(C_1-C_4)$alkyl, and $R^2$ is H, $(C_1-C_4)$alkyl, —$(C_0-C_2)$-alkylene-phenyl, or —C(O)O—R', wherein R' is H or $(C_1-C_4)$alkyl.

10. The hydrogel composition of claim 7, wherein the second polymerizable monomer has a carboxylic acid moiety.

11. The hydrogel composition of claim 10, wherein the second polymerizable monomer is acrylic acid or a derivative thereof, methacrylic acid, itaconic acid, fumaric acid, maleic acid, or vinylacetic acid.

12. The hydrogel composition of claim 7, further comprising one or more monomers which are methacrylic acid, itaconic acid, fumaric acid, maleic acid, vinylacetic acid or tert-butyl-2-acryloylhydrazinecarboxylate (BAHC), 2-dimethylaminoethylmethacrylate (DMAEMA), 2-dimethylaminoethyacrylate (DMAEA), aminoethyl methacrylate (AEMA), allylamine, or derivatives of any of the above, or which has the structure of the formula (II)

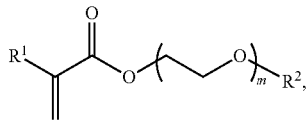

wherein
$R^1$ and $R^2$ are as defined in claim 8, and
m is any integer between 2-5.

13. The hydrogel composition of claim 6, wherein second precursor polymer is a copolymer comprising monomeric units of:
   a. a first monomer which is oligoethylene glycol methacrylate, or a derivative thereof; and
   b. at least one second polymerizable monomer which can be functionalized with a aldehyde moiety or a ketone moiety.

14. The hydrogel composition of claim 13, wherein the first monomer has the structure of the formula (I)

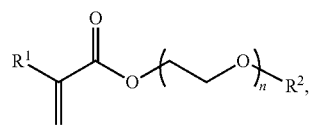

wherein
$R^1$ is H, $(C_1$-$C_{10})$alkyl or $(C_2$-$C_{10})$alkynyl;
$R^2$ is H, $(C_1$-$C_{10})$alkyl, $(C_2$-$C_{10})$alkynyl, —$(C_0$-$C_4)$-alkylene-$(C_6$-$C_{10})$aryl, —$(C_0$-$C_4)$-alkylene-$(C_5$-$C_{10})$heteroaryl, —C(O)NR' or —C(O)OR', wherein R' is H or $(C_1$-$C_6)$alkyl, and
n is any integer between 6 and 30.

15. The hydrogel composition of claim 13, wherein the second polymerizable monomer is functionalized with an acetal moiety or a ketal moiety.

16. The hydrogel composition of claim 13, wherein the second polymerizable monomer is N-(2,2-dimethoxyethyl) methacrylamide (DMEMAm) or (N-((2-methyl-1,3-dioxolan-2-yl)methyl)methacrylamide).

17. The hydrogel composition of claim 14, further comprising one or more monomers which are acrylic acid, methacrylic acid, itaconic acid, fumaric acid, maleic acid, vinylacetic acid or tert-butyl-2-acryloylhydrazinecarboxylate (BAHC), -dimethylaminoethyacrylate (DMAEA), aminoethyl methacrylate (AEMA), allylamine, or derivatives of any of the above,
or which has the structure of the formula (II)

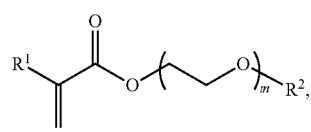

wherein
$R^1$ and $R^2$ are as defined in claim 8, and
m is any integer between 2-5.

18. The hydrogel composition of claim 6, wherein
   a. the first precursor polymer is a co-polymer of at least oligoethylene glycol methacrylate and acrylic acid;
   b. the second precursor polymer is a co-polymer of at least oligoethylene glycol methacrylate and N-(2,2-dimethoxyethyl)methacrylamide (DMEMAm),
wherein acrylic acid has carboxylic acid groups which are functionalized as hydrazide moieties, and DMEMAm has acetal groups which are functionalized as aldehyde moieties, and hydrazone bonds form between the hydrazide and aldehyde moieties.

19. A method for coating a substrate with a hydrogel composition, the method comprising,
   a. adsorbing or reacting a first or second precursor polymer as defined in claim 1 on the substrate;
   b. coating the substrate from step (a) with the alternate precursor polymer;
   c. optionally repeating steps (a) and (b),
      wherein the hydrogel composition as defined in claim 1 is formed on the substrate.

* * * * *